(12) United States Patent
Wang et al.

(10) Patent No.: US 11,408,978 B2
(45) Date of Patent: Aug. 9, 2022

(54) METHOD, APPARATUS, AND SYSTEM FOR VITAL SIGNS MONITORING USING HIGH FREQUENCY WIRELESS SIGNALS

(71) Applicants: Fengyu Wang, College Park, MD (US); Beibei Wang, Clarksville, MD (US); Chenshu Wu, Hong Kong (CN); Feng Zhang, Greenbelt, MD (US); K. J. Ray Liu, Potomac, MD (US); Oscar Chi-Lim Au, San Jose, CA (US)

(72) Inventors: Fengyu Wang, College Park, MD (US); Beibei Wang, Clarksville, MD (US); Chenshu Wu, Hong Kong (CN); Feng Zhang, Greenbelt, MD (US); K. J. Ray Liu, Potomac, MD (US); Oscar Chi-Lim Au, San Jose, CA (US)

(73) Assignee: ORIGIN WIRELESS, INC., Greenbelt, MD (US)

( * ) Notice: Subject to any disclaimer, the term of this patent is extended or adjusted under 35 U.S.C. 154(b) by 0 days.

(21) Appl. No.: 16/871,006

(22) Filed: May 10, 2020

(65) Prior Publication Data

US 2020/0300972 A1 Sep. 24, 2020

Related U.S. Application Data

(63) Continuation-in-part of application No. 15/326,112, filed as application No. PCT/US2015/041037 on Jul.
(Continued)

(51) Int. Cl.
*G01S 7/41* (2006.01)
*A61B 5/08* (2006.01)
(Continued)

(52) U.S. Cl.
CPC ............ *G01S 7/415* (2013.01); *A61B 5/0245* (2013.01); *A61B 5/02405* (2013.01);
(Continued)

(58) Field of Classification Search
CPC ........ G01S 7/415; G01S 13/003; G01S 13/50; G01S 7/006; G01S 13/56; G01S 13/88;
(Continued)

(56) References Cited

U.S. PATENT DOCUMENTS

2017/0090026 A1* 3/2017 Joshi ................. G01S 13/56
2020/0275402 A1* 8/2020 Shi .................. H04W 4/025

OTHER PUBLICATIONS

Huang et al., "Feasibility and Limits of Wi-Fi Imaging", Nov. 3, 2014, SenSys'14, ACM 978-1-4503-1169-4 (Year: 2014).*
(Continued)

*Primary Examiner* — Zhiyu Lu

(57) ABSTRACT

Methods, apparatus and systems for wireless vital signs monitoring are described. In one embodiment, a described system comprises: a transmitter, a receiver, a processor. The transmitter transmits, using N1 transmit antennas, a wireless signal through a wireless multipath channel of a venue, while a first object in the venue is having a first repetitive motion. The receiver receives, using N2 receive antennas, the wireless signal through the wireless multipath channel, and extracts a plurality of time series of channel information (TSCI) of the wireless multipath channel from the wireless signal. N1 and N2 are positive integers. Each of the plurality of TSCI is associated with a transmit antenna of the transmitter and a receive antenna of the receiver. The processor computes a first information of the first repetitive motion based on the plurality of TSCI, and monitors the first repetitive motion of the first object based on the first information.

28 Claims, 13 Drawing Sheets

Related U.S. Application Data 17, 2015, application No. 16/871,006, which is a continuation-in-part of application No. 16/127,151, filed on Sep. 10, 2018, now Pat. No. 11,012,285, which is a continuation-in-part of application No. PCT/US2017/021963, filed on Mar. 10, 2017, application No. 16/871,006, which is a continuation-in-part of application No. 16/125,748, filed on Sep. 9, 2018, now Pat. No. 10,833,912, which is a continuation-in-part of application No. PCT/US2017/015909, filed on Jan. 31, 2017, application No. 16/871,006, which is a continuation-in-part of application No. 15/861,422, filed on Jan. 3, 2018, now Pat. No. 11,025,475, and a continuation-in-part of application No. 16/200,608, filed on Nov. 26, 2018, now Pat. No. 10,735,298, and a continuation-in-part of application No. 16/446,589, filed on Jun. 19, 2019, now Pat. No. 10,742,475, and a continuation-in-part of application No. 16/667,648, filed on Oct. 29, 2019, now Pat. No. 11,035,940, and a continuation-in-part of application No. 16/667,757, filed on Oct. 29, 2019, now abandoned, and a continuation-in-part of application No. 16/790,610, filed on Feb. 13, 2020, and a continuation-in-part of application No. 16/790,627, filed on Feb. 13, 2020, and a continuation-in-part of application No. 16/798,337, filed on Feb. 22, 2020, now Pat. No. 10,845,463, which is a continuation-in-part of application No. 16/798,343, filed on Feb. 22, 2020.

(60) Provisional application No. 62/846,686, filed on May 12, 2019, provisional application No. 62/846,688, filed on May 12, 2019, provisional application No. 62/868,782, filed on Jun. 28, 2019, provisional application No. 62/849,853, filed on May 18, 2019, provisional application No. 62/873,781, filed on Jul. 12, 2019, provisional application No. 62/900,565, filed on Sep. 15, 2019, provisional application No. 62/902,357, filed on Sep. 18, 2019, provisional application No. 62/950,093, filed on Dec. 18, 2019, provisional application No. 62/977,326, filed on Feb. 16, 2020, provisional application No. 62/980,206, filed on Feb. 22, 2020, provisional application No. 62/981,387, filed on Feb. 25, 2020, provisional application No. 62/984,737, filed on Mar. 3, 2020, provisional application No. 63/001,226, filed on Mar. 27, 2020.

(51) Int. Cl.
| | | |
|---|---|---|
| *A61B 5/024* | (2006.01) | |
| *A61B 5/00* | (2006.01) | |
| *A61B 5/11* | (2006.01) | |
| *G01S 13/00* | (2006.01) | |
| *A61B 5/0245* | (2006.01) | |
| *A61B 5/05* | (2021.01) | |

(52) U.S. Cl.
CPC .......... *A61B 5/02444* (2013.01); *A61B 5/05* (2013.01); *A61B 5/0816* (2013.01); *A61B 5/1126* (2013.01); *A61B 5/7207* (2013.01); *A61B 5/7246* (2013.01); *A61B 5/746* (2013.01); *G01S 13/003* (2013.01)

(58) Field of Classification Search
CPC .......... G01S 7/417; G01S 13/04; G01S 7/412; G01S 13/42; G01S 13/86; G01S 7/411; G01S 11/02; G01S 13/284; G01S 13/34; G01S 13/343; G01S 13/44; G01S 13/46; G01S 13/52; G01S 13/582; G01S 13/584; G01S 13/765; G01S 13/886; G01S 2013/462; G01S 5/0252; G01S 5/06; G01S 7/2883; G01S 7/354; G01S 7/356; A61B 5/02405; A61B 5/02444; A61B 5/0245; A61B 5/05; A61B 5/1126; A61B 5/7207; A61B 4/746; A61B 5/0816; A61B 5/024; A61B 5/1113; A61B 5/1118; A61B 5/112; A61B 5/113; A61B 5/165; A61B 5/4809; A61B 5/4818; A61B 5/7246; A61B 5/0002; A61B 5/0004; A61B 5/0022; A61B 5/0205; A61B 5/021; A61B 5/0507; A61B 5/11; A61B 5/1112; A61B 5/1117; A61B 5/4806; A61B 5/4812; A61B 5/4815; A61B 5/6887; A61B 5/6898; A61B 5/7253; A61B 5/7282; A61B 5/746; H04L 12/44; H04L 1/0026; H04L 1/24; H04L 21/44; H04L 25/0226; H04L 45/48; H04W 40/02; H04W 48/08; H04W 56/001; H04W 84/18; H04W 24/08; H04W 4/021; H04W 24/02; H04W 4/023; H04W 4/029; H04W 24/06; H04W 4/026; H04W 4/027; H04W 48/16; H04W 52/0203; H04W 52/0277; H04W 84/12; G01N 22/00; H04B 17/309; H04B 1/713; H04B 17/21; H04B 17/23; H04B 17/24; H04B 17/318; H04B 17/391; H04B 7/0874; G06F 3/167; G06F 2203/0384; G06F 4/0346; G06F 3/03545; G06F 3/038; G06N 20/00; G08B 13/187; G08B 13/24; G08B 21/0423; G08B 21/043; G08B 21/0469; G08B 29/188; G16H 40/67; G16H 50/20; G16Y 20/10; Y02D 30/70; B60R 2325/101; B60R 2325/106; B60R 25/31

See application file for complete search history.

(56) References Cited

OTHER PUBLICATIONS

Wu et al., "Non-Invasive Detection of Moving and Stationary Human With WiFi", May 2015, IEEE Journal on Selected Areas in Communications (Year: 2015).*

Adib et al., "Smart Homes that Monitors Breathing and Heart Rate", Apr. 2015, ACM (Year: 2015).*

* cited by examiner

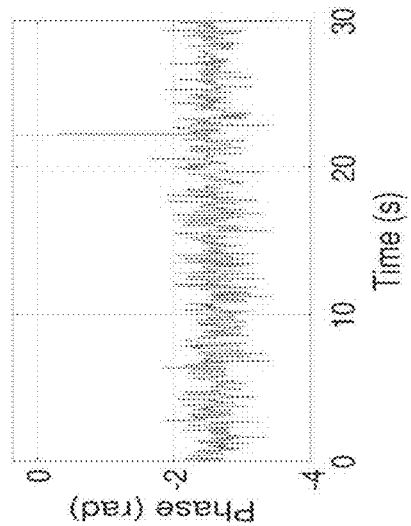
FIG. 5A
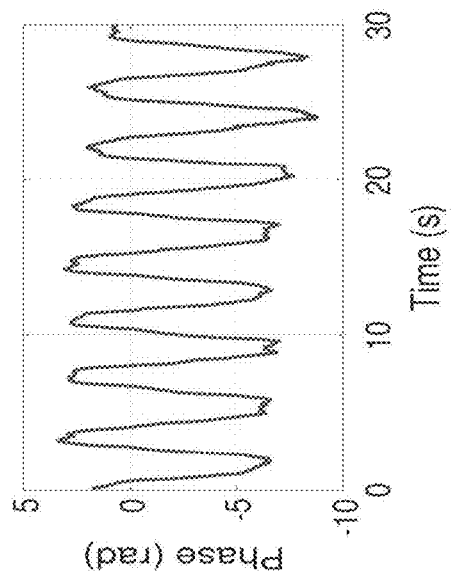
FIG. 5B
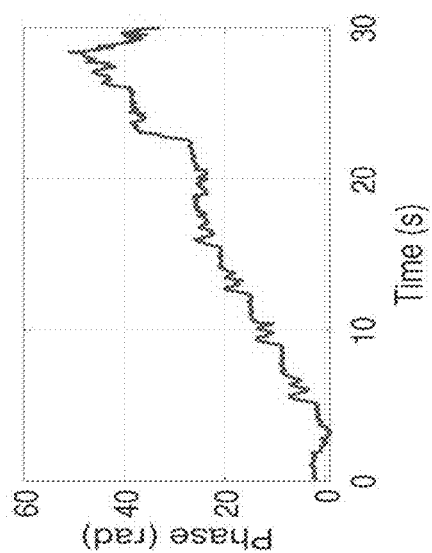
FIG. 5C
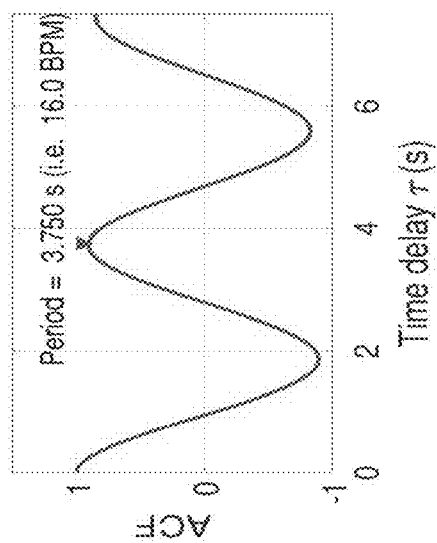
FIG. 5D
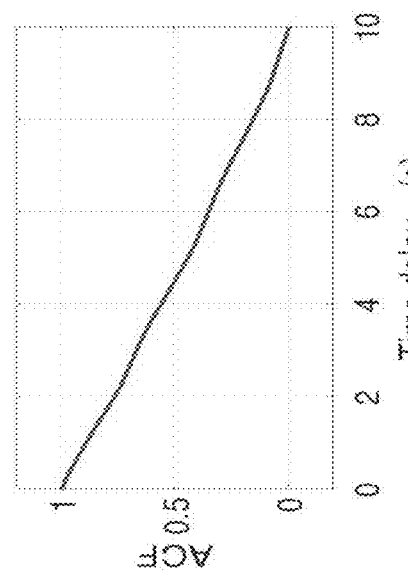
FIG. 5E
FIG. 5F

METHOD, APPARATUS, AND SYSTEM FOR VITAL SIGNS MONITORING USING HIGH FREQUENCY WIRELESS SIGNALS

CROSS-REFERENCE TO RELATED APPLICATIONS

The present application is related to U.S. patent application, entitled "METHOD, APPARATUS, AND SYSTEM FOR PEOPLE COUNTING AND RECOGNITION BASED ON RHYTHMIC MOTION MONITORING," filed on May 10, 2020, which is expressly incorporated by reference herein in its entirety.

The present application hereby incorporates by reference the entirety of the disclosures of, and claims priority to, each of the following cases:

(a) U.S. patent application Ser. No. 15/326,112, entitled "WIRELESS POSITIONING SYSTEMS", filed on Jan. 13, 2017,
  (1) which is a national stage entry of PCT patent application PCT/US2015/041037, entitled "WIRELESS POSITIONING SYSTEMS", filed on Jul. 17, 2015, published as WO 2016/011433A2 on Jan. 21, 2016,
(b) U.S. patent application Ser. No. 16/127,151, entitled "METHODS, APPARATUS, SERVERS, AND SYSTEMS FOR VITAL SIGNS DETECTION AND MONITORING", filed on Sep. 10, 2018,
  (1) which is a continuation-in-part of PCT patent application PCT/US2017/021963, entitled "METHODS, APPARATUS, SERVERS, AND SYSTEMS FOR VITAL SIGNS DETECTION AND MONITORING", filed on Mar. 10, 2017, published as WO2017/156492A1 on Sep. 14, 2017,
(c) U.S. patent application Ser. No. 16/125,748, entitled "METHODS, DEVICES, SERVERS, APPARATUS, AND SYSTEMS FOR WIRELESS INTERNET OF THINGS APPLICATIONS", filed on Sep. 9, 2018,
  (1) which is a continuation-in-part of PCT patent application PCT/US2017/015909, entitled "METHODS, DEVICES, SERVERS, APPARATUS, AND SYSTEMS FOR WIRELESS INTERNET OF THINGS APPLICATIONS", filed on Jan. 31, 2017, published as WO2017/155634A1 on Sep. 14, 2017,
(d) U.S. patent application Ser. No. 15/861,422, entitled "METHOD, APPARATUS, SERVER, AND SYSTEMS OF TIME-REVERSAL TECHNOLOGY", filed on Jan. 3, 2018,
(e) U.S. patent application Ser. No. 16/200,608, entitled "METHOD, APPARATUS, SERVER AND SYSTEM FOR VITAL SIGN DETECTION AND MONITORING", filed on Nov. 26, 2018,
(f) U.S. Provisional Patent application 62/846,686, entitled "METHOD, APPARATUS, AND SYSTEM FOR WIRELESS INERTIAL MEASUREMENT", filed on May 12, 2019,
(g) U.S. Provisional Patent application 62/846,688, entitled "Method, Apparatus, and System for Processing and Presenting Life Log based on a Wireless Signal", filed on May 12, 2019,
(h) U.S. Provisional Patent application 62/849,853, entitled "Method, Apparatus, and System for Wireless Artificial Intelligent in Smart Car", filed on May 18, 2019,
(i) U.S. patent application Ser. No. 16/446,589, entitled "METHOD, APPARATUS, AND SYSTEM FOR OBJECT TRACKING AND SENSING USING BROADCASTING", filed on Jun. 19, 2019,
(j) U.S. Provisional Patent application 62/868,782, entitled "METHOD, APPARATUS, AND SYSTEM FOR VITAL SIGNS MONITORING USING HIGH FREQUENCY WIRELESS SIGNALS", filed on Jun. 28, 2019,
(k) U.S. Provisional Patent application 62/873,781, entitled "METHOD, APPARATUS, AND SYSTEM FOR IMPROVING TOPOLOGY OF WIRELESS SENSING SYSTEMS", filed on Jul. 12, 2019,
(l) U.S. Provisional Patent application 62/900,565, entitled "QUALIFIED WIRELESS SENSING SYSTEM", filed on Sep. 15, 2019,
(m) U.S. Provisional Patent application 62/902,357, entitled "METHOD, APPARATUS, AND SYSTEM FOR AUTOMATIC AND OPTIMIZED DEVICE-TO-CLOUD CONNECTION FOR WIRELESS SENSING", filed on Sep. 18, 2019,
(n) U.S. patent application Ser. No. 16/667,648, entitled "METHOD, APPARATUS, AND SYSTEM FOR WIRELESS PROXIMITY AND PRESENCE MONITORING", filed on Oct. 29, 2019,
(o) U.S. patent application Ser. No. 16/667,757, entitled "METHOD, APPARATUS, AND SYSTEM FOR HUMAN IDENTIFICATION BASED ON HUMAN RADIO BIOMETRIC INFORMATION", filed on Oct. 29, 2019,
(p) U.S. Provisional Patent application 62/950,093, entitled "METHOD, APPARATUS, AND SYSTEM FOR TARGET POSITIONING", filed on Dec. 18, 2019,
(q) U.S. patent application Ser. No. 16/790,610, entitled "METHOD, APPARATUS, AND SYSTEM FOR WIRELESS GAIT RECOGNITION", filed Feb. 13, 2020,
(r) U.S. patent application Ser. No. 16/790,627, entitled "METHOD, APPARATUS, AND SYSTEM FOR OUTDOOR TARGET TRACKING", filed Feb. 13, 2020.
(s) U.S. Provisional Patent application 62/977,326, entitled "METHOD, APPARATUS, AND SYSTEM FOR AUTOMATIC AND ADAPTIVE WIRELESS MONITORING AND TRACKING", filed on Feb. 16, 2020,
(t) U.S. patent application Ser. No. 16/798,337, entitled "METHOD, APPARATUS, AND SYSTEM FOR WIRELESS OBJECT SCANNING", filed Feb. 22, 2020,
(u) U.S. patent application Ser. No. 16/798,343, entitled "METHOD, APPARATUS, AND SYSTEM FOR WIRELESS OBJECT TRACKING", filed Feb. 22, 2020,
(v) U.S. Provisional Patent application 62/980,206, entitled "METHOD, APPARATUS, AND SYSTEM FOR WIRELESS SENSING", filed on Feb. 22, 2020,
(w) U.S. Provisional Patent application 62/981,387, entitled "METHOD, APPARATUS, AND SYSTEM FOR VEHICLE WIRELESS MONITORING", filed on Feb. 25, 2020,
(x) U.S. Provisional Patent application 62/984,737, entitled "METHOD, APPARATUS, AND SYSTEM FOR IMPROVED WIRELESS MONITORING", filed on Mar. 3, 2020,
(y) U.S. Provisional Patent application 63/001,226, entitled "METHOD, APPARATUS, AND SYSTEM FOR IMPROVED WIRELESS MONITORING AND USER INTERFACE", filed on Mar. 27, 2020.

TECHNICAL FIELD

The present teaching generally relates to wireless vital signs monitoring system. More specifically, the present teaching relates to accurately tracking breathing/respiration rate of human being, and heart rate variability (HRV) based on wireless channel information in a rich-scattering environment.

BACKGROUND

Continuous monitoring of respiration as well as heart rate is critical for early detection and prevention of potentially fatal diseases. Current solutions usually require users to wear dedicated devices such as wrist-worn sensors or chest straps, which require to contact human body during the monitoring, making them less convenient and comfortable. With the rapid development of Internet of Things (IoT), wireless sensing has received increasing attention in recent years because of the ubiquitous deployment of wireless devices. It has been proved that the presence of human will affect wireless signal propagation, enabling the functionality of wirelessly monitoring human subjects by analyzing the electromagnetic (EM) wave.

Recent works of wireless human vital signs detection leverage the existing communication infrastructure (e.g. WiFi) to provide a pervasive, user-friendly and affordable solution for health status monitoring. Over the past decade, great efforts have been put into designing and testing different architectures for robust vital sign monitoring using off-the-shelf WiFi devices. However, due to the relative low carrier frequency of WiFi systems, the antenna number of 2.4/5 GHz WiFi is small, rendering a low spatial resolution. Besides, the narrow bandwidth of WiFi systems results in a coarse range resolution (7.5 meters with bandwidth 20 MHz). Therefore, when there are multiple users present, the received radio frequency (RF) signals are reflected by the multiple users and it is hard to extract the vital signs for each of them. Thus, most of works assume there is only one single person, or the breathing rates of different users are distinct. Moreover, since the RF signal is reflected by multiple scatters, the embedded heartbeat signal has extremely low signal-to-noise ratio (SNR). As such, it is extremely difficult, if possible, to use commodity WiFi to estimate the heart rate.

SUMMARY

The present teaching generally relates to wireless vital signs monitoring system. More specifically, the present teaching relates to accurately tracking breathing/respiration rate of human being, and heart rate variability (HRV) based on wireless channel information in a rich-scattering environment.

In one embodiment, a wireless monitoring system is described. The wireless monitoring system comprises: a transmitter, a receiver, and a processor. The transmitter is configured for transmitting, using N1 transmit antennas, a wireless signal through a wireless multipath channel of a venue, while a first object in the venue is having a first repetitive motion. The receiver is configured for: receiving, using N2 receive antennas, the wireless signal through the wireless multipath channel, and extracting a plurality of time series of channel information (TSCI) of the wireless multipath channel from the wireless signal. N1 and N2 are positive integers. Each of the plurality of TSCI is associated with a transmit antenna of the transmitter and a receive antenna of the receiver. The processor is configured for: computing a first information of the first repetitive motion based on the plurality of TSCI, and monitoring the first repetitive motion of the first object based on the first information.

In another embodiment, a method, implemented by a processor, a memory communicatively coupled with the processor, and a set of instructions stored in the memory to be executed by the processor, is described. The method comprises: transmitting, using N1 transmit antennas of a first heterogeneous wireless device, a wireless signal through a wireless multipath channel of a venue, while an object in the venue is having a repetitive motion; receiving, using N2 receive antennas of a second heterogeneous wireless device, the wireless signal through the wireless multipath channel; obtaining a plurality of time series of channel information (TSCI) of the wireless multipath channel from the wireless signal, wherein: N1 and N2 are positive integers, and each of the plurality of TSCI is associated with a transmit antenna of the first heterogeneous wireless device and a receive antenna of the second heterogeneous wireless device; computing a timing information of the repetitive motion based on the plurality of TSCI; and monitoring the repetitive motion of the object based on the timing information.

In a different embodiment, a wireless monitoring system is described. The wireless monitoring system comprises: a plurality of pairs of transmitters and receivers in a venue, and processor. For each pair of the plurality of pairs: a respective transmitter of the pair is configured for asynchronously transmitting a respective wireless signal through a wireless multipath channel, while a first object in the venue is having a first repetitive motion, and a respective receiver of the pair is configured for asynchronously receiving the respective wireless signal through the wireless multipath channel, and extracting a respective time series of channel information (TSCI) of the wireless multipath channel from the respective wireless signal. The transmitter and the receiver of a first pair of the plurality of pairs are collocated at a same location in the venue. The transmitter and the receiver of a second pair of the plurality of pairs are positioned at two different locations in the venue. A plurality of TSCI is obtained by the receivers of the plurality of pairs. The processor is configured for: computing a first information of the first repetitive motion based on the plurality of TSCI, and monitoring the first repetitive motion of the first object based on the first information.

Other concepts relate to software for implementing the present teaching on wireless monitoring in a rich-scattering environment. Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or devices described herein are further described in terms of exemplary embodiments. These exemplary embodiments are described in detail with reference to the drawings. These embodiments are nonlimiting exemplary embodiments, in which like reference numerals represent similar structures throughout the several views of the drawings.

FIGS. 5A-5F illustrate exemplary phases for target detection, according to some embodiments of the present disclosure.

DETAILED DESCRIPTION

Figure 1:
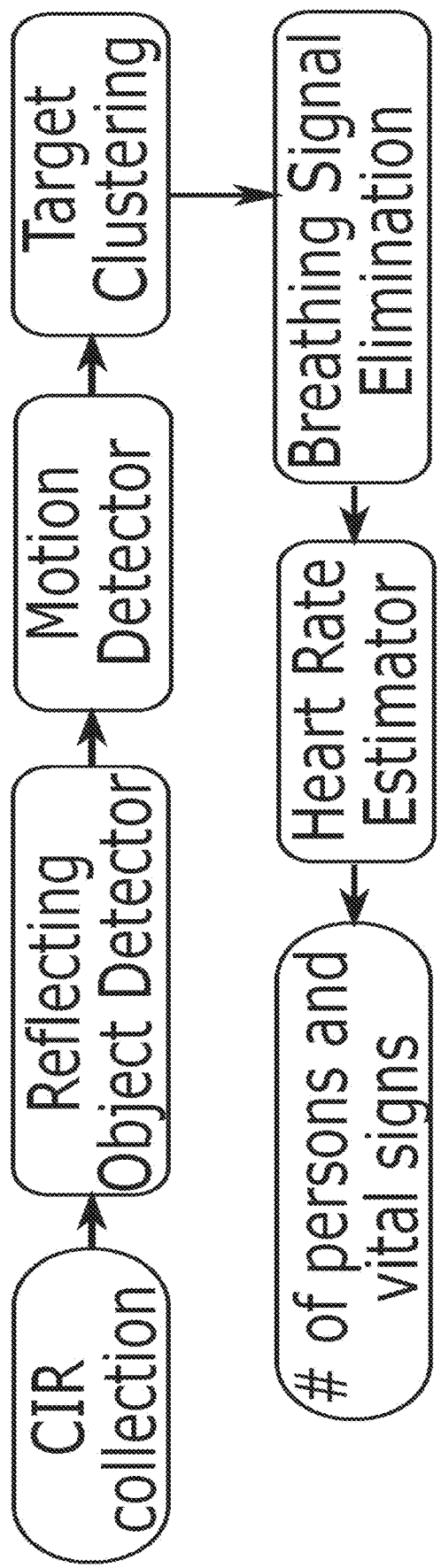
FIG. 1 illustrates a processing flow of the disclosed system, according to some embodiments of the present disclosure.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

In one embodiment, the present teaching discloses a method, apparatus, device, system, and/or software (method/apparatus/device/system/software) of a wireless monitoring system. A time series of channel information (CI) of a wireless multipath channel (channel) may be obtained (e.g. dynamically) using a processor, a memory communicatively coupled with the processor and a set of instructions stored in the memory. The time series of CI (TSCI) may be extracted from a wireless signal (signal) transmitted between a Type 1 heterogeneous wireless device (e.g. wireless transmitter, TX) and a Type 2 heterogeneous wireless device (e.g. wireless receiver, RX) in a venue through the channel. The channel may be impacted by an expression (e.g. motion, movement, expression, and/or change in position/pose/shape/expression) of an object in the venue. A characteristics and/or a spatial-temporal information (STI, e.g. motion information) of the object and/or of the motion of the object may be monitored based on the TSCI. A task may be performed based on the characteristics and/or STI. A presentation associated with the task may be generated in a user-interface (UI) on a device of a user. The TSCI may be a wireless signal stream. The TSCI or each CI may be preprocessed. A device may be a station (STA). The symbol "A/B" means "A and/or B" in the present teaching.

The expression may comprise placement, placement of moveable parts, location, position, orientation, identifiable place, region, spatial coordinate, presentation, state, static expression, size, length, width, height, angle, scale, shape, curve, surface, area, volume, pose, posture, manifestation, body language, dynamic expression, motion, motion sequence, gesture, extension, contraction, distortion, deformation, body expression (e.g. head, face, eye, mouth, tongue, hair, voice, neck, limbs, arm, hand, leg, foot, muscle, moveable parts), surface expression (e.g. shape, texture, material, color, electromagnetic (EM) characteristics, visual pattern, wetness, reflectance, translucency, flexibility), material property (e.g. living tissue, hair, fabric, metal, wood, leather, plastic, artificial material, solid, liquid, gas, temperature), movement, activity, behavior, change of expression, and/or some combination.

The wireless signal may comprise: transmitted/received signal, EM radiation, RF signal/transmission, signal in licensed/unlicensed/ISM band, bandlimited signal, baseband signal, wireless/mobile/cellular communication signal, wireless/mobile/cellular network signal, mesh signal, light signal/communication, downlink/uplink signal, unicast/multicast/broadcast signal, standard (e.g. WLAN, WWAN, WPAN, WBAN, international, national, industry, defacto, IEEE, IEEE 802, 802.11/15/16, WiFi, 802.11n/ac/ax/be, 3G/4G/LTE/5G/6G/7G/8G, 3GPP, Bluetooth, BLE, Zigbee, RFID, UWB, WiMax) compliant signal, protocol signal, standard frame, beacon/pilot/probe/enquiry/acknowledgement/handshake/synchronization signal, management/control/data frame, management/control/data signal, standardized wireless/cellular communication protocol, reference signal, source signal, motion probe/detection/sensing signal, and/or series of signals. The wireless signal may comprise a line-of-sight (LOS), and/or a non-LOS component (or path/link). Each CI may be extracted/generated/computed/sensed at a layer (e.g. PHY/MAC layer in OSI model) of Type 2 device and may be obtained by an application (e.g. software, firmware, driver, app, wireless monitoring software/system).

The wireless multipath channel may comprise: a communication channel, analog frequency channel (e.g. with analog carrier frequency near 700/800/900 MHz, 1.8/1.8/2.4/3/5/6/

27/60 GHz), coded channel (e.g. in CDMA), and/or channel of a wireless network/system (e.g. WLAN, WiFi, mesh, LTE, 4G/5G, Bluetooth, Zigbee, UWB, RFID, microwave). It may comprise multiple channel. The channels may be consecutive (e.g. with adjacent/overlapping bands) or non-consecutive channels (e.g. non-overlapping WiFi channels, one at 2.4 GHz and one at 5 GHz).

The TSCI may be extracted from the wireless signal at a layer of the Type 2 device (e.g. a layer of OSI reference model, physical layer, data link layer, logical link control layer, media access control (MAC) layer, network layer, transport layer, session layer, presentation layer, application layer, TCP/IP layer, internet layer, link layer). The TSCI may be extracted from a derived signal (e.g. baseband signal, motion detection signal, motion sensing signal) derived from the wireless signal (e.g. RF signal). It may be (wireless) measurements sensed by the communication protocol (e.g. standardized protocol) using existing mechanism (e.g. wireless/cellular communication standard/network, 3G/LTE/4G/5G/6G/7G/8G, WiFi, IEEE 802.11/15/16). The derived signal may comprise a packet with at least one of: a preamble, a header and a payload (e.g. for data/control/management in wireless links/networks). The TSCI may be extracted from a probe signal (e.g. training sequence, STF, LTF, L-STF, L-LTF, L-SIG, HE-STF, HE-LTF, HE-SIG-A, HE-SIG-B, CEF) in the packet. A motion detection/sensing signal may be recognized/identified base on the probe signal. The packet may be a standard-compliant protocol frame, management frame, control frame, data frame, sounding frame, excitation frame, illumination frame, null data frame, beacon frame, pilot frame, probe frame, request frame, response frame, association frame, reassociation frame, disassociation frame, authentication frame, action frame, report frame, poll frame, announcement frame, extension frame, enquiry frame, acknowledgement frame, RTS frame, CTS frame, QoS frame, CF-Poll frame, CF-Ack frame, block acknowledgement frame, reference frame, training frame, and/or synchronization frame.

The packet may comprise a control data and/or a motion detection probe. A data (e.g. ID/parameters/characteristics/settings/control signal/command/instruction/notification/broadcasting-related information of the Type 1 device) may be obtained from the payload. The wireless signal may be transmitted by the Type 1 device. It may be received by the Type 2 device. A database (e.g. in local server, hub device, cloud server, storage network) may be used to store the TSCI, characteristics, STI, signatures, patterns, behaviors, trends, parameters, analytics, output responses, identification information, user information, device information, channel information, venue (e.g. map, environmental model, network, proximity devices/networks) information, task information, class/category information, presentation (e.g. UI) information, and/or other information.

The Type 1/Type 2 device may comprise at least one of: electronics, circuitry, transmitter (TX)/receiver (RX)/transceiver, RF interface, "Origin Satellite"/"Tracker Bot", unicast/multicast/broadcasting device, wireless source device, source/destination device, wireless node, hub device, target device, motion detection device, sensor device, remote/wireless sensor device, wireless communication device, wireless-enabled device, standard compliant device, and/or receiver. The Type 1 (or Type 2) device may be heterogeneous because, when there are multiple instances of Type 1 (or Type 2) device, they may have different circuitry, enclosure, structure, purpose, auxiliary functionality, chip/IC, processor, memory, software, firmware, network connectivity, antenna, brand, model, appearance, form, shape, color, material, and/or specification. The Type 1/Type 2 device may comprise: access point, router, mesh router, internet-of-things (IoT) device, wireless terminal, one or more radio/RF subsystem/wireless interface (e.g. 2.4 GHz radio, 5 GHz radio, front haul radio, backhaul radio), modem, RF front end, RF/radio chip or integrated circuit (IC).

At least one of: Type 1 device, Type 2 device, a link between them, the object, the characteristics, the STI, the monitoring of the motion, and the task may be associated with an identification (ID) such as UUID. The Type 1/Type 2/another device may obtain/store/retrieve/access/preprocess/condition/process/analyze/monitor/apply the TSCI. The Type 1 and Type 2 devices may communicate network traffic in another channel (e.g. Ethernet, HDMI, USB, Bluetooth, BLE, WiFi, LTE, other network, the wireless multipath channel) in parallel to the wireless signal. The Type 2 device may passively observe/monitor/receive the wireless signal from the Type 1 device in the wireless multipath channel without establishing connection (e.g. association/authentication) with, or requesting service from, the Type 1 device.

The transmitter (i.e. Type 1 device) may function as (play role of) receiver (i.e. Type 2 device) temporarily, sporadically, continuously, repeatedly, interchangeably, alternately, simultaneously, concurrently, and/or contemporaneously; and vice versa. A device may function as Type 1 device (transmitter) and/or Type 2 device (receiver) temporarily, sporadically, continuously, repeatedly, simultaneously, concurrently, and/or contemporaneously. There may be multiple wireless nodes each being Type 1 (TX) and/or Type 2 (RX) device. A TSCI may be obtained between every two nodes when they exchange/communicate wireless signals. The characteristics and/or STI of the object may be monitored individually based on a TSCI, or jointly based on two or more (e.g. all) TSCI. The motion of the object may be monitored actively (in that Type 1 device, Type 2 device, or both, are wearable of/associated with the object) and/or passively (in that both Type 1 and Type 2 devices are not wearable of/associated with the object). It may be passive because the object may not be associated with the Type 1 device and/or the Type 2 device. The object (e.g. user, an automated guided vehicle or AGV) may not need to carry/install any wearables/fixtures (i.e. the Type 1 device and the Type 2 device are not wearable/attached devices that the object needs to carry in order perform the task). It may be active because the object may be associated with either the Type 1 device and/or the Type 2 device. The object may carry (or installed) a wearable/a fixture (e.g. the Type 1 device, the Type 2 device, a device communicatively coupled with either the Type 1 device or the Type 2 device).

The presentation may be visual, audio, image, video, animation, graphical presentation, text, etc. A computation of the task may be performed by a processor (or logic unit) of the Type 1 device, a processor (or logic unit) of an IC of the Type 1 device, a processor (or logic unit) of the Type 2 device, a processor of an IC of the Type 2 device, a local server, a cloud server, a data analysis subsystem, a signal analysis subsystem, and/or another processor. The task may be performed with/without reference to a wireless fingerprint or a baseline (e.g. collected, processed, computed, transmitted and/or stored in a training phase/survey/current survey/previous survey/recent survey/initial wireless survey, a passive fingerprint), a training, a profile, a trained profile, a static profile, a survey, an initial wireless survey, an initial setup, an installation, a retraining, an updating and a reset.

The Type 1 device (TX device) may comprise at least one heterogeneous wireless transmitter. The Type 2 device (RX device) may comprise at least one heterogeneous wireless receiver. The Type 1 device and the Type 2 device may be collocated. The Type 1 device and the Type 2 device may be the same device. Any device may have a data processing unit/apparatus, a computing unit/system, a network unit/ system, a processor (e.g. logic unit), a memory communicatively coupled with the processor, and a set of instructions stored in the memory to be executed by the processor. Some processors, memories and sets of instructions may be coordinated. There may be multiple Type 1 devices interacting (e.g. communicating, exchange signal/control/notification/ other data) with the same Type 2 device (or multiple Type 2 devices), and/or there may be multiple Type 2 devices interacting with the same Type 1 device. The multiple Type 1 devices/Type 2 devices may be synchronized and/or asynchronous, with same/different window width/size and/ or time shift, same/different synchronized start time, synchronized end time, etc. Wireless signals sent by the multiple Type 1 devices may be sporadic, temporary, continuous, repeated, synchronous, simultaneous, concurrent, and/or contemporaneous. The multiple Type 1 devices/ Type 2 devices may operate independently and/or collaboratively. A Type I and/or Type 2 device may have/comprise/ be heterogeneous hardware circuitry (e.g. a heterogeneous chip or a heterogeneous IC capable of generating/receiving the wireless signal, extracting CI from received signal, or making the CI available). They may be communicatively coupled to same or different servers (e.g. cloud server, edge server, local server, hub device).

Operation of one device may be based on operation, state, internal state, storage, processor, memory output, physical location, computing resources, network of another device. Difference devices may communicate directly, and/or via another device/server/hub device/cloud server. The devices may be associated with one or more users, with associated settings. The settings may be chosen once, pre-programmed, and/or changed (e.g. adjusted, varied, modified)/varied over time. There may be additional steps in the method. The steps and/or the additional steps of the method may be performed in the order shown or in another order. Any steps may be performed in parallel, iterated, or otherwise repeated or performed in another manner. A user may be human, adult, older adult, man, woman, juvenile, child, baby, pet, animal, creature, machine, computer module/software, etc.

In the case of one or multiple Type 1 devices interacting with one or multiple Type 2 devices, any processing (e.g. time domain, frequency domain) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/ characteristics of the devices.

The wireless receiver (e.g. Type 2 device) may receive the signal and/or another signal from the wireless transmitter (e.g. Type 1 device). The wireless receiver may receive another signal from another wireless transmitter (e.g. a second Type 1 device). The wireless transmitter may transmit the signal and/or another signal to another wireless receiver (e.g. a second Type 2 device). The wireless transmitter, wireless receiver, another wireless receiver and/or another wireless transmitter may be moving with the object and/or another object. The another object may be tracked.

The Type I and/or Type 2 device may be capable of wirelessly coupling with at least two Type 2 and/or Type 1 devices. The Type 1 device may be caused/controlled to switch/establish wireless coupling (e.g. association, authentication) from the Type 2 device to a second Type 2 device at another location in the venue. Similarly, the Type 2 device may be caused/controlled to switch/establish wireless coupling from the Type 1 device to a second Type 1 device at yet another location in the venue. The switching may be controlled by a server (or a hub device), the processor, the Type 1 device, the Type 2 device, and/or another device. The radio used before and after switching may be different. A second wireless signal (second signal) may be caused to be transmitted between the Type 1 device and the second Type 2 device (or between the Type 2 device and the second Type 1 device) through the channel. A second TSCI of the channel extracted from the second signal may be obtained. The second signal may be the first signal. The characteristics, STI and/or another quantity of the object may be monitored based on the second TSCI. The Type 1 device and the Type 2 device may be the same. The characteristics, STI and/or another quantity with different time stamps may form a waveform. The waveform may be displayed in the presentation.

The wireless signal and/or another signal may have data embedded. The wireless signal may be a series of probe signals (e.g. a repeated transmission of probe signals, a re-use of one or more probe signals). The probe signals may change/vary over time. A probe signal may be a standard compliant signal, protocol signal, standardized wireless protocol signal, control signal, data signal, wireless communication network signal, cellular network signal, WiFi signal, LTE/5G/6G/7G signal, reference signal, beacon signal, motion detection signal, and/or motion sensing signal. A probe signal may be formatted according to a wireless network standard (e.g. WiFi), a cellular network standard (e.g. LTE/5G/6G), or another standard. A probe signal may comprise a packet with a header and a payload. A probe signal may have data embedded. The payload may comprise data. A probe signal may be replaced by a data signal. The probe signal may be embedded in a data signal. The wireless receiver, wireless transmitter, another wireless receiver and/ or another wireless transmitter may be associated with at least one processor, memory communicatively coupled with respective processor, and/or respective set of instructions stored in the memory which when executed cause the processor to perform any and/or all steps needed to determine the STI (e.g. motion information), initial STI, initial time, direction, instantaneous location, instantaneous angle, and/or speed, of the object. The processor, the memory and/or the set of instructions may be associated with the Type 1 device, one of the at least one Type 2 device, the object, a device associated with the object, another device associated with the venue, a cloud server, a hub device, and/or another server.

The Type 1 device may transmit the signal in a broadcasting manner to at least one Type 2 device(s) through the channel in the venue. The signal is transmitted without the Type 1 device establishing wireless connection (e.g. association, authentication) with any Type 2 device, and without any Type 2 device requesting services from the Type 1 device. The Type 1 device may transmit to a particular media access control (MAC) address common for multiple Type 2 devices. Each Type 2 device may adjust its MAC address to the particular MAC address. The particular MAC address may be associated with the venue. The association may be recorded in an association table of an Association Server (e.g. hub device). The venue may be identified by the Type 1 device, a Type 2 device and/or another device based on the particular MAC address, the series of probe signals, and/or the at least one TSCI extracted from the probe signals. For example, a Type 2 device may be moved to a new location in the venue (e.g. from another venue). The Type 1 device may be newly set up in the venue such that the Type 1 and Type 2 devices are not aware of each other. During set up, the Type 1 device may be instructed/guided/caused/controlled (e.g. using dummy receiver, using hardware pin setting/connection, using stored setting, using local setting, using remote setting, using downloaded setting, using hub device, or using server) to send the series of probe signals to the particular MAC address. Upon power up, the Type 2 device may scan for probe signals according to a table of MAC addresses (e.g. stored in a designated source, server, hub device, cloud server) that may be used for broadcasting at different locations (e.g. different MAC address used for different venue such as house, office, enclosure, floor, multi-storey building, store, airport, mall, stadium, hall, station, subway, lot, area, zone, region, district, city, country, continent). When the Type 2 device detects the probe signals sent to the particular MAC address, the Type 2 device can use the table to identify the venue based on the MAC address. A location of a Type 2 device in the venue may be computed based on the particular MAC address, the series of probe signals, and/or the at least one TSCI obtained by the Type 2 device from the probe signals. The computing may be performed by the Type 2 device. The particular MAC address may be changed (e.g. adjusted, varied, modified) over time. It may be changed according to a time table, rule, policy, mode, condition, situation and/or change. The particular MAC address may be selected based on availability of the MAC address, a pre-selected list, collision pattern, traffic pattern, data traffic between the Type 1 device and another device, effective bandwidth, random selection, and/or a MAC address switching plan. The particular MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel. The selected channel may be changed (e.g. adjusted, varied, modified) over time. The change may be according to a time table, rule, policy, mode, condition, situation, and/or change. The selected channel may be selected based on availability of channels, random selection, a pre-selected list, co-channel interference, inter-channel interference, channel traffic pattern, data traffic between the Type 1 device and another device, effective bandwidth associated with channels, security criterion, channel switching plan, a criterion, a quality criterion, a signal quality condition, and/or consideration.

The particular MAC address and/or an information of the selected channel may be communicated between the Type 1 device and a server (e.g. hub device) through a network. The particular MAC address and/or the information of the selected channel may also be communicated between a Type 2 device and a server (e.g. hub device) through another network. The Type 2 device may communicate the particular MAC address and/or the information of the selected channel to another Type 2 device (e.g. via mesh network, Bluetooth, WiFi, NFC, ZigBee, etc.). The particular MAC address and/or selected channel may be chosen by a server (e.g. hub device). The particular MAC address and/or selected channel may be signaled in an announcement channel by the Type 1 device, the Type 2 device and/or a server (e.g. hub device). Before being communicated, any information may be pre-processed.

Wireless connection (e.g. association, authentication) between the Type 1 device and another wireless device may be established (e.g. using a signal handshake). The Type 1 device may send a first handshake signal (e.g. sounding frame, probe signal, request-to-send RTS) to the another device. The another device may reply by sending a second handshake signal (e.g. a command, or a clear-to-send CTS) to the Type 1 device, triggering the Type 1 device to transmit the signal (e.g. series of probe signals) in the broadcasting manner to multiple Type 2 devices without establishing connection with any Type 2 device. The second handshake signals may be a response or an acknowledge (e.g. ACK) to the first handshake signal. The second handshake signal may contain a data with information of the venue, and/or the Type 1 device. The another device may be a dummy device with a purpose (e.g. primary purpose, secondary purpose) to establish the wireless connection with the Type 1 device, to receive the first signal, and/or to send the second signal. The another device may be physically attached to the Type 1 device.

In another example, the another device may send a third handshake signal to the Type 1 device triggering the Type 1 device to broadcast the signal (e.g. series of probe signals) to multiple Type 2 devices without establishing connection (e.g. association, authentication) with any Type 2 device. The Type 1 device may reply to the third special signal by transmitting a fourth handshake signal to the another device. The another device may be used to trigger multiple Type 1 devices to broadcast. The triggering may be sequential, partially sequential, partially parallel, or fully parallel. The another device may have multiple wireless circuitries to trigger multiple transmitters in parallel. Parallel trigger may also be achieved using at least one yet another device to perform the triggering (similar to what as the another device does) in parallel to the another device. The another device may not communicate (or suspend communication) with the Type 1 device after establishing connection with the Type 1 device. Suspended communication may be resumed. The another device may enter an inactive mode, hibernation mode, sleep mode, stand-by mode, low-power mode, OFF mode and/or power-down mode, after establishing the connection with the Type 1 device. The another device may have the particular MAC address so that the Type 1 device sends the signal to the particular MAC address. The Type 1 device and/or the another device may be controlled and/or coordinated by a first processor associated with the Type 1 device, a second processor associated with the another device, a third processor associated with a designated source and/or a fourth processor associated with another device. The first and second processors may coordinate with each other.

A first series of probe signals may be transmitted by a first antenna of the Type 1 device to at least one first Type 2 device through a first channel in a first venue. A second series of probe signals may be transmitted by a second antenna of the Type 1 device to at least one second Type 2 device through a second channel in a second venue. The first series and the second series may/may not be different. The at least one first Type 2 device may/may not be different from the at least one second Type 2 device. The first and/or second series of probe signals may be broadcasted without connection (e.g. association, authentication) established between the Type 1 device and any Type 2 device. The first and second antennas may be same/different. The two venues may have different sizes, shape, multipath characteristics. The first and second venues may overlap. The respective immediate areas around the first and second antennas may overlap. The first and second channels may be same/different. For example, the first one may be WiFi while the second may be LTE. Or, both may be WiFi, but the first one may be 2.4 GHz WiFi and the second may be 5 GHz WiFi. Or, both may be 2.4 GHz WiFi, but have different channel numbers, SSID names, and/or WiFi settings.

Each Type 2 device may obtain at least one TSCI from the respective series of probe signals, the CI being of the respective channel between the Type 2 device and the Type 1 device. Some first Type 2 device(s) and some second Type 2 device(s) may be the same. The first and second series of probe signals may be synchronous/asynchronous. A probe signal may be transmitted with data or replaced by a data signal. The first and second antennas may be the same. The first series of probe signals may be transmitted at a first rate (e.g. 30 Hz). The second series of probe signals may be transmitted at a second rate (e.g. 200 Hz). The first and second rates may be same/different. The first and/or second rate may be changed (e.g. adjusted, varied, modified) over time. The change may be according to a time table, rule, policy, mode, condition, situation, and/or change. Any rate may be changed (e.g. adjusted, varied, modified) over time. The first and/or second series of probe signals may be transmitted to a first MAC address and/or second MAC address respectively. The two MAC addresses may be same/different. The first series of probe signals may be transmitted in a first channel. The second series of probe signals may be transmitted in a second channel. The two channels may be same/different. The first or second MAC address, first or second channel may be changed over time. Any change may be according to a time table, rule, policy, mode, condition, situation, and/or change.

The Type 1 device and another device may be controlled and/or coordinated, physically attached, or may be of/in/of a common device. They may be controlled by/connected to a common data processor, or may be connected to a common bus interconnect/network/LAN/Bluetooth network/NFC network/BLE network/wired network/wireless network/mesh network/mobile network/cloud. They may share a common memory, or be associated with a common user, user device, profile, account, identity (ID), identifier, household, house, physical address, location, geographic coordinate, IP subnet, SSID, home device, office device, and/or manufacturing device. Each Type 1 device may be a signal source of a set of respective Type 2 devices (i.e. it sends a respective signal (e.g. respective series of probe signals) to the set of respective Type 2 devices). Each respective Type 2 device chooses the Type 1 device from among all Type 1 devices as its signal source. Each Type 2 device may choose asynchronously. At least one TSCI may be obtained by each respective Type 2 device from the respective series of probe signals from the Type 1 device, the CI being of the channel between the Type 2 device and the Type 1 device. The respective Type 2 device chooses the Type 1 device from among all Type 1 devices as its signal source based on identity (ID) or identifier of Type 1/Type 2 device, task to be performed, past signal source, history (e.g. of past signal source, Type 1 device, another Type 1 device, respective Type 2 receiver, and/or another Type 2 receiver), threshold for switching signal source, and/or information of a user, account, access info, parameter, characteristics, and/or signal strength (e.g. associated with the Type 1 device and/or the respective Type 2 receiver). Initially, the Type 1 device may be signal source of a set of initial respective Type 2 devices (i.e. the Type 1 device sends a respective signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed (e.g. adjusted, varied, modified) when (1) time interval between two adjacent probe signals (e.g. between current probe signal and immediate past probe signal, or between next probe signal and current probe signal) received from current signal source of the Type 2 device exceeds a first threshold; (2) signal strength associated with current signal source of the Type 2 device is below a second threshold; (3) a processed signal strength associated with current signal source of the Type 2 device is below a third threshold, the signal strength processed with low pass filter, band pass filter, median filter, moving average filter, weighted averaging filter, linear filter and/or non-linear filter; and/or (4) signal strength (or processed signal strength) associated with current signal source of the Type 2 device is below a fourth threshold for a significant percentage of a recent time window (e.g. 70%, 800/%, 90%). The percentage may exceed a fifth threshold. The first, second, third, fourth and/or fifth thresholds may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the Type 2 device may not change if other Type 1 devices have signal strength weaker than a factor (e.g. 1, 1.1, 1.2, or 1.5) of the current signal source. If the signal source is changed (e.g. adjusted, varied, modified), the new signal source may take effect at a near future time (e.g. the respective next time). The new signal source may be the Type 1 device with strongest signal strength, and/or processed signal strength. The current and new signal source may be same/different.

A list of available Type 1 devices may be initialized and maintained by each Type 2 device. The list may be updated by examining signal strength and/or processed signal strength associated with the respective set of Type 1 devices. A Type 2 device may choose between a first series of probe signals from a first Type 1 device and a second series of probe signals from a second Type 1 device based on: respective probe signal rate, MAC addresses, channels, characteristics/properties/states, task to be performed by the Type 2 device, signal strength of first and second series, and/or another consideration.

The series of probe signals may be transmitted at a regular rate (e.g. 100 Hz). The series of probe signals may be scheduled at a regular interval (e.g. 0.01 s for 100 Hz), but each probe signal may experience small time perturbation, perhaps due to timing requirement, timing control, network control, handshaking, message passing, collision avoidance, carrier sensing, congestion, availability of resources, and/or another consideration. The rate may be changed (e.g. adjusted, varied, modified). The change may be according to a time table (e.g. changed once every hour), rule, policy, mode, condition and/or change (e.g. changed whenever some event occur). For example, the rate may normally be 100 Hz, but changed to 1000 Hz in demanding situations, and to 1 Hz in low power/standby situation. The probe signals may be sent in burst.

The probe signal rate may change based on a task performed by the Type 1 device or Type 2 device (e.g. a task may need 100 Hz normally and 1000 Hz momentarily for 20 seconds). In one example, the transmitters (Type 1 devices), receivers (Type 2 device), and associated tasks may be associated adaptively (and/or dynamically) to classes (e.g. classes that are: low-priority, high-priority, emergency, critical, regular, privileged, non-subscription, subscription, paying, and/or non-paying). A rate (of a transmitter) may be adjusted for the sake of some class (e.g. high priority class). When the need of that class changes, the rate may be changed (e.g. adjusted, varied, modified). When a receiver has critically low power, the rate may be reduced to reduce power consumption of the receiver to respond to the probe signals. In one example, probe signals may be used to transfer power wirelessly to a receiver (Type 2 device), and the rate may be adjusted to control the amount of power transferred to the receiver.

The rate may be changed by (or based on): a server (e.g. hub device), the Type 1 device and/or the Type 2 device. Control signals may be communicated between them. The server may monitor, track, forecast and/or anticipate the needs of the Type 2 device and/or the tasks performed by the Type 2 device, and may control the Type 1 device to change the rate. The server may make scheduled changes to the rate according to a time table. The server may detect an emergency situation and change the rate immediately. The server may detect a developing condition and adjust the rate gradually. The characteristics and/or STI (e.g. motion information) may be monitored individually based on a TSCI associated with a particular Type 1 device and a particular Type 2 device, and/or monitored jointly based on any TSCI associated with the particular Type 1 device and any Type 2 device, and/or monitored jointly based on any TSCI associated with the particular Type 2 device and any Type 1 device, and/or monitored globally based on any TSCI associated with any Type 1 device and any Type 2 device. Any joint monitoring may be associated with: a user, user account, profile, household, map of venue, environmental model of the venue, and/or user history, etc.

A first channel between a Type 1 device and a Type 2 device may be different from a second channel between another Type 1 device and another Type 2 device. The two channels may be associated with different frequency bands, bandwidth, carrier frequency, modulation, wireless standards, coding, encryption, payload characteristics, networks, network ID, SSID, network characteristics, network settings, and/or network parameters, etc. The two channels may be associated with different kinds of wireless system (e.g. two of the following: WiFi, LTE, LTE-A, LTE-U, 2.5G, 3G, 3.5G, 4G, beyond 4G, 5G, 6G, 7G, a cellular network standard, UMTS, 3GPP, GSM, EDGE, TDMA, FDMA, CDMA, WCDMA, TD-SCDMA, 802.11 system, 802.15 system, 802.16 system, mesh network, Zigbee, NFC, WiMax, Bluetooth, BLE, RFID, UWB, microwave system, radar like system). For example, one is WiFi and the other is LTE. The two channels may be associated with similar kinds of wireless system, but in different network. For example, the first channel may be associated with a WiFi network named "Pizza and Pizza" in the 2.4 GHz band with a bandwidth of 20 MHz while the second may be associated with a WiFi network with SSID of "StarBud hotspot" in the 5 GHz band with a bandwidth of 40 MHz. The two channels may be different channels in same network (e.g. the "Star-Bud hotspot" network).

In one embodiment, a wireless monitoring system may comprise training a classifier of multiple events in a venue based on training TSCI associated with the multiple events. A CI or TSCI associated with an event may be considered/ may comprise a wireless sample/characteristics/fingerprint associated with the event (and/or the venue, the environment, the object, the motion of the object, a state/emotional state/mental state/condition/stage/gesture/gait/action/movement/activity/daily activity/history/event of the object, etc.). For each of the multiple known events happening in the venue in a respective training (e.g. surveying, wireless survey, initial wireless survey) time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training TSCI) may be obtained asynchronously by each of the at least one first Type 2 device from the (respective) training signal. The CI may be CI of the channel between the first Type 2 device and the first Type 1 device in the training time period associated with the known event. The at least one training TSCI may be preprocessed. The training may be a wireless survey (e.g. during installation of Type 1 device and/or Type 2 device).

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the channel in the venue in the current time period associated with the current event. At least one time series of current CI (current TSCI) may be obtained asynchronously by each of the at least one second Type 2 device from the current signal (e.g. the series of current probe signals). The CI may be CI of the channel between the second Type 2 device and the second Type 1 device in the current time period associated with the current event. The at least one current TSCI may be preprocessed.

The classifier may be applied to classify at least one current TSCI obtained from the series of current probe signals by the at least one second Type 2 device, to classify at least one portion of a particular current TSCI, and/or to classify a combination of the at least one portion of the particular current TSCI and another portion of another TSCI. The classifier may partition TSCI (or the characteristics/STI or other analytics or output responses) into clusters and associate the clusters to specific events/objects/subjects/locations/movements/activities. Labels/tags may be generated for the clusters. The clusters may be stored and retrieved. The classifier may be applied to associate the current TSCI (or characteristics/STI or the other analytics/output response, perhaps associated with a current event) with: a cluster, a known/specific event, a class/category/group/grouping/list/cluster/set of known events/subjects/locations/movements/activities, an unknown event, a class/category/group/grouping/list/cluster/set of unknown events/subjects/locations/movements/activities, and/or another event/subject/location/movement/activity/class/category/group/grouping/list/cluster/set. Each TSCI may comprise at least one CI each associated with a respective timestamp. Two TSCI associated with two Type 2 devices may be different with different: starting time, duration, stopping time, amount of CI, sampling frequency, sampling period. Their CI may have different features. The first and second Type 1 devices may be at same location in the venue. They may be the same device. The at least one second Type device (or their locations) may be a permutation of the at least one first Type 2 device (or their locations). A particular second Type 2 device and a particular first Type 2 device may be the same device. A subset of the first Type 2 device and a subset of the second Type 2 device may be the same. The at least one second Type 2 device and/or a subset of the at least one second Type 2 device may be a subset of the at least one first Type 2 device. The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device. The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first TSCI and a second section of a second time duration of the second section of the second TSCI may be aligned. A map between items of the first section and items of the second section may be computed. The first section may comprise a first segment (e.g. subset) of the first TSCI with a first starting/ending time, and/or another segment (e.g. subset) of a processed first TSCI. The processed first TSCI may be the first TSCI processed by a first operation. The second section may comprise a second segment (e.g. subset) of the second TSCI with a second starting time and a second ending time, and another segment (e.g. subset) of a processed second TSCI. The processed second TSCI may be the second TSCI processed by a second operation. The first operation and/or the second operation may comprise: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many. At least one function of at least one of: the first item of the first section of the first TSCI, another item of the first TSCI, timestamp of the first item, time difference of the first item, time differential of the first item, neighboring timestamp of the first item, another timestamp associated with the first item, the second item of the second section of the second TSCI, another item of the second TSCI, timestamp of the second item, time difference of the second item, time differential of the second item, neighboring timestamp of the second item, and another timestamp associated with the second item, may satisfy at least one constraint.

One constraint may be that a difference between the timestamp of the first item and the timestamp of the second item may be upper-bounded by an adaptive (and/or dynamically adjusted) upper threshold and lower-bounded by an adaptive lower threshold.

The first section may be the entire first TSCI. The second section may be the entire second TSCI. The first time duration may be equal to the second time duration. A section of a time duration of a TSCI may be determined adaptively (and/or dynamically). A tentative section of the TSCI may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing timestamp may be considered as a current item, one item at a time.

In each iteration, at least one activity measure/index may be computed and/or considered. The at least one activity measure may be associated with at least one of: the current item associated with a current timestamp, past items of the tentative section with timestamps not larger than the current timestamp, and/or future items of the tentative section with timestamps not smaller than the current timestamp. The current item may be added to the beginning portion of the tentative section if at least one criterion (e.g. quality criterion, signal quality condition) associated with the at least one activity measure is satisfied.

The at least one criterion associated with the activity measure may comprise at least one of: (a) the activity measure is smaller than an adaptive (e.g. dynamically adjusted) upper threshold, (b) the activity measure is larger than an adaptive lower threshold, (c) the activity measure is smaller than an adaptive upper threshold consecutively for at least a predetermined amount of consecutive timestamps, (d) the activity measure is larger than an adaptive lower threshold consecutively for at least another predetermined amount of consecutive timestamps, (e) the activity measure is smaller than an adaptive upper threshold consecutively for at least a predetermined percentage of the predetermined amount of consecutive timestamps, (f) the activity measure is larger than an adaptive lower threshold consecutively for at least another predetermined percentage of the another predetermined amount of consecutive timestamps, (g) another activity measure associated with another timestamp associated with the current timestamp is smaller than another adaptive upper threshold and larger than another adaptive lower threshold, (h) at least one activity measure associated with at least one respective timestamp associated with the current timestamp is smaller than respective upper threshold and larger than respective lower threshold, (i) percentage of timestamps with associated activity measure smaller than respective upper threshold and larger than respective lower threshold in a set of timestamps associated with the current timestamp exceeds a threshold, and (j) another criterion (e.g. a quality criterion, signal quality condition).

An activity measure/index associated with an item at time T1 may comprise at least one of: (1) a first function of the item at time T1 and an item at time T1−D1, wherein D1 is a pre-determined positive quantity (e.g. a constant time offset), (2) a second function of the item at time T1 and an item at time T1+D1, (3) a third function of the item at time T1 and an item at time T2, wherein T2 is a pre-determined quantity (e.g. a fixed initial reference time; T2 may be changed (e.g. adjusted, varied, modified) over time; T2 may be updated periodically; T2 may be the beginning of a time period and T1 may be a sliding time in the time period), and (4) a fourth function of the item at time T1 and another item.

At least one of: the first function, the second function, the third function, and/or the fourth function may be a function (e.g. $F(X, Y, \ldots)$) with at least two arguments: X and Y. The two arguments may be scalars. The function (e.g. F) may be a function of at least one of: X, Y, (X−Y), (Y−X), abs(X−Y), $X^a$, $Y^B$, abs($X^a$−$Y^B$), $(X-Y)^a$, (X/Y), (X+a)/(Y+b), $(X^a/Y^b)$, and $((X/Y)^a$−b), wherein a and b are may be some predetermined quantities. For example, the function may simply be abs(X−Y), or $(X-Y)^2$, $(X-Y)^4$. The function may be a robust function. For example, the function may be $(X-Y)^2$ when abs (X−Y) is less than a threshold T, and (X−Y)+a when abs(X−Y) is larger than T. Alternatively, the function may be a constant when abs(X−Y) is larger than T. The function may also be bounded by a slowly increasing function when abs(X−y) is larger than T, so that outliers cannot severely affect the result. Another example of the function may be (abs(X/Y)−a), where a=1. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative. In another example, both arguments X and Y may be n-tuples such that X=($x\_1$, $x\_2 \ldots, x\_n$) and Y=($y\_1, y\_2, \ldots, y\_n$). The function may be a function of at least one of: $x\_i, y\_i$, ($x\_i$−$y\_i$), ($y\_i$−$x\_i$), abs($x\_i$−$y\_i$), $x\_i^a$, $y\_i^b$, abs($x\_i^$−$y\_i^b$), ($x\_i$−$y\_i)^a$, ($x\_i$/$y\_i$), ($x\_i$+a)/($y\_i$+b), ($x\_i^a$/l $y\_i^b$), and (($x\_i$/$y\_i)^a$−b), wherein i is a component index of the n-tuple X and Y, and 1<=i<=n. E.g. component index of $x\_1$ is i=1, component index of $x\_2$ is i=2. The function may comprise a component-by-component summation of another function of at least one of the following: $x\_i, y\_i$, ($x\_i$−$y\_i$), ($y\_i$−$x\_i$), abs($x\_i$−$y\_i$), $x\_i^a$, $y\_i^b$, abs($x\_i^a$−$y\_i^b$), ($x\_i$−$y\_i)^a$, ($x\_i$/$y\_i$), ($x\_i$+a)/($y\_i$+b), ($x\_i^a$/$y\_i^b$), and (($x\_i$/$y\_i)^a$−b), wherein i is the component index of the n-tuple X and Y. For example, the function may be in a form of $\text{sum}\_\{i=1\}^n$ (abs($x\_i$/$y\_i$)−1)/n, or $\text{sum}\_\{i=1\}^n$ $w\_i$*(abs($x\_i$/$y\_i$)−1), where $w\_i$ is some weight for component i.

The map may be computed using dynamic time warping (DTW). The DTW may comprise a constraint on at least one of: the map, the items of the first TSCI, the items of the second TSCI, the first time duration, the second time duration, the first section, and/or the second section. Suppose in the map, the $i^\{th\}$ domain item is mapped to the $j^\{th\}$ range item. The constraint may be on admissible combination of i and j (constraint on relationship between i and j). Mismatch cost between a first section of a first time duration of a first TSCI and a second section of a second time duration of a second TSCI may be computed.

The first section and the second section may be aligned such that a map comprising multiple links may be established between first items of the first TSCI and second items of the second TSCI. With each link, one of the first items with a first timestamp may be associated with one of the second items with a second timestamp. A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, inner-product-like quantity, quantity based on correlation, correlation indicator, quantity based on covariance, discriminating score, distance, Euclidean distance, absolute distance, Lk distance (e.g. L1, L2, . . . ), weighted distance, distance-like quantity and/or another similarity value, between the first vector and the second vector. The mismatch cost may be normalized by the respective vector length.

A parameter derived from the mismatch cost between the first section of the first time duration of the first TSCI and the second section of the second time duration of the second TSCI may be modeled with a statistical distribution. At least one of: a scale parameter, location parameter and/or another parameter, of the statistical distribution may be estimated. The first section of the first time duration of the first TSCI may be a sliding section of the first TSCI. The second section of the second time duration of the second TSCI may be a sliding section of the second TSCI. A first sliding window may be applied to the first TSCI and a corresponding second sliding window may be applied to the second TSCI. The first sliding window of the first TSCI and the corresponding second sliding window of the second TSCI may be aligned.

Mismatch cost between the aligned first sliding window of the first TSCI and the corresponding aligned second sliding window of the second TSCI may be computed. The current event may be associated with at least one of: the known event, the unknown event and/or the another event, based on the mismatch cost.

The classifier may be applied to at least one of: each first section of the first time duration of the first TSCI, and/or each second section of the second time duration of the second TSCI, to obtain at least one tentative classification results. Each tentative classification result may be associated with a respective first section and a respective second section.

The current event may be associated with at least one of: the known event, the unknown event, a class/category/group/grouping/list/set of unknown events, and/or the another event, based on the mismatch cost. The current event may be associated with at least one of: the known event, the unknown event and/or the another event, based on a largest number of tentative classification results in multiple sections of the first TSCI and corresponding more than sections of the second TSCI. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%). In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost. The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2. The current event may be associated with at least one of: the known event, the unknown event and/or the another event, based on the mismatch cost and additional mismatch cost associated with at least one additional section of the first TSCI and at least one additional section of the second TSCI. The known events may comprise at least one of: a door closed event, door open event, window closed event, window open event, multi-state event, on-state event, off-state event, intermediate state event, continuous state event, discrete state event, human-present event, human-absent event, sign-of-life-present event, and/or a sign-of-life-absent event.

A projection for each CI may be trained using a dimension reduction method based on the training TSCI. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training TSCI associated with the at least one event, and/or the current TSCI, for the classifier. The classifier of the at least one event may be trained based on the projection and the training TSCI associated with the at least one event. The at least one current TSCI may be classified/categorized based on the projection and the current TSCI. The projection may be re-trained using at least one of: the dimension reduction method, and another dimension reduction method, based on at least one of: the training TSCI, at least one current TSCI before retraining the projection, and/or additional training TSCI. The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method. The classifier of the at least one event may be re-trained based on at least one of: the re-trained projection, the training TSCI associated with the at least one events, and/or at least one current TSCI. The at least one current TSCI may be classified based on: the re-trained projection, the re-trained classifier, and/or the current TSCI.

Each CI may comprise a vector of complex values. Each complex value may be preprocessed to give the magnitude of the complex value. Each CI may be preprocessed to give a vector of non-negative real numbers comprising the magnitude of corresponding complex values. Each training TSCI may be weighted in the training of the projection. The projection may comprise multiple projected components. The projection may comprise at least one most significant projected component. The projection may comprise at least one projected component that may be beneficial for the classifier.

The channel information (CI) may be associated with/may comprise signal strength, signal amplitude, signal phase, spectral power measurement, modem parameters (e.g. used in relation to modulation/demodulation in digital communication systems such as WiFi, 4G/LTE), dynamic beamforming information, transfer function components, radio state (e.g. used in digital communication systems to decode digital data, baseband processing state, RF processing state, etc.), measurable variables, sensed data, coarse-grained/fine-grained information of a layer (e.g. physical layer, data link layer, MAC layer, etc.), digital setting, gain setting, RF filter setting, RF front end switch setting, DC offset setting, DC correction setting, IQ compensation setting, effect(s) on the wireless signal by the environment (e.g. venue) during propagation, transformation of an input signal (the wireless signal transmitted by the Type 1 device) to an output signal (the wireless signal received by the Type 2 device), a stable behavior of the environment, a state profile, wireless channel measurements, received signal strength indicator (RSSI), channel state information (CSI), channel impulse response (CIR), channel frequency response (CFR), characteristics of frequency components (e.g. subcarriers) in a bandwidth, channel characteristics, channel filter response, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another channel information. Each CI may be associated with a time stamp, and/or an arrival time. A CSI can be used to equalize/undo/minimize/reduce the multipath channel effect (of the transmission channel) to demodulate a signal similar to the one transmitted by the transmitter through the multipath channel. The CI may be associated with information associated with a frequency band, frequency signature, frequency phase, frequency amplitude, frequency trend, frequency characteristics, frequency-like characteristics, time domain element, frequency domain element, time-frequency domain element, orthogonal decomposition characteristics, and/or non-orthogonal decomposition characteristics of the signal through the channel. The TSCI may be a stream of wireless signals (e.g. CI).

The CI may be preprocessed, processed, postprocessed, stored (e.g. in local memory, portable/mobile memory, removable memory, storage network, cloud memory, in a volatile manner, in a non-volatile manner), retrieved, transmitted and/or received. One or more modem parameters and/or radio state parameters may be held constant. The modem parameters may be applied to a radio subsystem. The modem parameters may represent a radio state. A motion detection signal (e.g. baseband signal, and/or packet decoded/demodulated from the baseband signal, etc.) may be obtained by processing (e.g. down-converting) the first wireless signal (e.g. RF/WiFi/LTE/5G signal) by the radio subsystem using the radio state represented by the stored modem parameters. The modem parameters/radio state may be updated (e.g. using previous modem parameters or previous radio state). Both the previous and updated modem parameters/radio states may be applied in the radio subsystem in the digital communication system. Both the previous and updated modem parameters/radio states may be compared/analyzed/processed/monitored in the task.

The channel information may also be modem parameters (e.g. stored or freshly computed) used to process the wireless signal. The wireless signal may comprise a plurality of probe signals. The same modem parameters may be used to process multiple probe signals. The same modem parameters may also be used to process multiple wireless signals. The modem parameters may comprise parameters that indicate settings or an overall configuration for the operation of a radio subsystem or a baseband subsystem of a wireless sensor device (or both). The modem parameters may include one or more of: a gain setting, an RF filter setting, an RF front end switch setting, a DC offset setting, or an IQ compensation setting for a radio subsystem, or a digital DC correction setting, a digital gain setting, and/or a digital filtering setting (e.g. for a baseband subsystem). The CI may also be associated with information associated with a time period, time signature, timestamp, time amplitude, time phase, time trend, and/or time characteristics of the signal. The CI may be associated with information associated with a time-frequency partition, signature, amplitude, phase, trend, and/or characteristics of the signal. The CI may be associated with a decomposition of the signal. The CI may be associated with information associated with a direction, angle of arrival (AoA), angle of a directional antenna, and/or a phase of the signal through the channel. The CI may be associated with attenuation patterns of the signal through the channel. Each CI may be associated with a Type 1 device and a Type 2 device. Each CI may be associated with an antenna of the Type 1 device and an antenna of the Type 2 device.

The CI may be obtained from a communication hardware (e.g. of Type 2 device, or Type 1 device) that is capable of providing the CI. The communication hardware may be a WiFi-capable chip/IC (integrated circuit), chip compliant with a 802.11 or 802.16 or another wireless/radio standard, next generation WiFi-capable chip, LTE-capable chip, 5G-capable chip, 6G/7G/8G-capable chip, Bluetooth-enabled chip, NFC (near field communication)-enabled chip, BLE (Bluetooth low power)-enabled chip, UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc. The channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc. Each CI may be associated with a timestamp. Each CI may comprise N1 components (e.g. N1 frequency domain components in CFR, N1 time domain components in CIR, or N1 decomposition components). Each component may be associated with a component index. Each component may be a real, imaginary, or complex quantity, magnitude, phase, flag, and/or set. Each CI may comprise a vector or matrix of complex numbers, a set of mixed quantities, and/or a multi-dimensional collection of at least one complex numbers.

Components of a TSCI associated with a particular component index may form a respective component time series associated with the respective index. A TSCI may be divided into N1 component time series. Each respective component time series is associated with a respective component index. The characteristics/STI of the motion of the object may be monitored based on the component time series. In one example, one or more ranges of CI components (e.g. one range being from component 11 to component 23, a second range being from component 44 to component 50, and a third range having only one component) may be selected based on some criteria/cost function/signal quality metric (e.g. based on signal-to-noise ratio, and/or interference level) for further processing.

A component-wise characteristic of a component-feature time series of a TSCI may be computed. The component-wise characteristics may be a scalar (e.g. energy) or a function with a domain and a range (e.g. an autocorrelation function, transform, inverse transform). The characteristics/STI of the motion of the object may be monitored based on the component-wise characteristics. A total characteristics (e.g. aggregate characteristics) of the TSCI may be computed based on the component-wise characteristics of each component time series of the TSCI. The total characteristics may be a weighted average of the component-wise characteristics. The characteristics/STI of the motion of the object may be monitored based on the total characteristics. An aggregate quantity may be a weighted average of individual quantities.

The Type 1 device and Type 2 device may support WiFi, WiMax, 3G/beyond 3G, 4G/beyond 4G, LTE, LTE-A, 5G, 6G, 7G, Bluetooth, NFC, BLE, Zigbee, UWB, UMTS, 3GPP, GSM, EDGE, TDMA, FDMA, CDMA, WCDMA, TD-SCDMA, mesh network, proprietary wireless system, IEEE 802.11 standard, 802.15 standard, 802.16 standard, 3GPP standard, and/or another wireless system.

A common wireless system and/or a common wireless channel may be shared by the Type 1 transceiver and/or the at least one Type 2 transceiver. The at least one Type 2 transceiver may transmit respective signal contemporaneously (or: asynchronously, synchronously, sporadically, continuously, repeatedly, concurrently, simultaneously and/or temporarily) using the common wireless system and/or the common wireless channel. The Type 1 transceiver may transmit a signal to the at least one Type 2 transceiver using the common wireless system and/or the common wireless channel.

Each Type 1 device and Type 2 device may have at least one transmitting/receiving antenna. Each CI may be associated with one of the transmitting antenna of the Type 1 device and one of the receiving antenna of the Type 2 device. Each pair of a transmitting antenna and a receiving antenna may be associated with a link, a path, a communication path, signal hardware path, etc. For example, if the Type 1 device has M (e.g. 3) transmitting antennas, and the Type 2 device has N (e.g. 2) receiving antennas, there may be M×N (e.g. 3×2=6) links or paths. Each link or path may be associated with a TSCI.

The at least one TSCI may correspond to various antenna pairs between the Type 1 device and the Type 2 device. The Type 1 device may have at least one antenna. The Type 2 device may also have at least one antenna. Each TSCI may be associated with an antenna of the Type 1 device and an antenna of the Type 2 device. Averaging or weighted averaging over antenna links may be performed. The averaging or weighted averaging may be over the at least one TSCI. The averaging may optionally be performed on a subset of the at least one TSCI corresponding to a subset of the antenna pairs.

Timestamps of CI of a portion of a TSCI may be irregular and may be corrected so that corrected timestamps of time-corrected CI may be uniformly spaced in time. In the case of multiple Type 1 devices and/or multiple Type 2 devices, the corrected timestamp may be with respect to the same or different clock. An original timestamp associated with each of the CI may be determined. The original timestamp may not be uniformly spaced in time. Original timestamps of all CI of the particular portion of the particular TSCI in the current sliding time window may be corrected so that corrected timestamps of time-corrected CI may be uniformly spaced in time.

The characteristics and/or STI (e.g. motion information) may comprise: location, location coordinate, change in location, position (e.g. initial position, new position), position on map, height, horizontal location, vertical location, distance, displacement, speed, acceleration, rotational speed, rotational acceleration, direction, angle of motion, azimuth, direction of motion, rotation, path, deformation, transformation, shrinking, expanding, gait, gait cycle, head motion, repeated motion, periodic motion, pseudo-periodic motion, impulsive motion, sudden motion, fall-down motion, transient motion, behavior, transient behavior, period of motion, frequency of motion, time trend, temporal profile, temporal characteristics, occurrence, change, temporal change, change of CL change in frequency, change in timing, change of gait cycle, timing, starting time, initiating time, ending time, duration, history of motion, motion type, motion classification, frequency, frequency spectrum, frequency characteristics, presence, absence, proximity, approaching, receding, identity/identifier of the object, composition of the object, head motion rate, head motion direction, mouth-related rate, eye-related rate, breathing rate, heart rate, tidal volume, depth of breath, inhale time, exhale time, inhale time to exhale time ratio, airflow rate, heart heat-to-beat interval, heart rate variability, hand motion rate, hand motion direction, leg motion, body motion, walking rate, hand motion rate, positional characteristics, characteristics associated with movement (e.g. change in position/location) of the object, tool motion, machine motion, complex motion, and/or combination of multiple motions, event, signal statistics, signal dynamics, anomaly, motion statistics, motion parameter, indication of motion detection, motion magnitude, motion phase, similarity score, distance score, Euclidean distance, weighted distance, L_1 norm, L_2 norm, L_k norm for k>2, statistical distance, correlation, correlation indicator, auto-correlation, covariance, auto-covariance, cross-covariance, inner product, outer product, motion signal transformation, motion feature, presence of motion, absence of motion, motion localization, motion identification, motion recognition, presence of object, absence of object, entrance of object, exit of object, a change of object, motion cycle, motion count, gait cycle, motion rhythm, deformation motion, gesture, handwriting, head motion, mouth motion, heart motion, internal organ motion, motion trend, size, length, area, volume, capacity, shape, form, tag, starting/initiating location, ending location, starting/initiating quantity, ending quantity, event, fall-down event, security event, accident event, home event, office event, factory event, warehouse event, manufacturing event, assembly line event, maintenance event, car-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and/or another information. The characteristics and/or STI may be computed/monitored based on a feature computed from a CI or a TSCI (e.g. feature computation/extraction). A static segment or profile (and/or a dynamic segment/profile) may be identified/computed/analyzed/monitored/extracted/obtained/marked/presented/indicated/highlighted/stored/communicated based on an analysis of the feature. The analysis may comprise a motion detection/movement assessment/presence detection. Computational workload may be shared among the Type 1 device, the Type 2 device and another processor.

The Type 1 device and/or Type 2 device may be a local device. The local device may be: a smart phone, smart device, TV, sound bar, set-top box, access point, router, repeater, wireless signal repeater/extender, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, home device, vehicle device, office device, building device, manufacturing device, watch, glasses, clock, television, oven, air-conditioner, accessory, utility, appliance, smart machine, smart vehicle, internet-of-thing (IoT) device, internet-enabled device, computer, portable computer, tablet, smart house, smart office, smart building, smart parking lot, smart system, and/or another device.

Each Type 1 device may be associated with a respective identifier (e.g. ID). Each Type 2 device may also be associated with a respective identify (ID). The ID may comprise: numeral, combination of text and numbers, name, password, account, account ID, web link, web address, index to some information, and/or another ID. The ID may be assigned. The ID may be assigned by hardware (e.g. hardwired, via dongle and/or other hardware), software and/or firmware. The ID may be stored (e.g. in database, in memory, in server (e.g. hub device), in the cloud, stored locally, stored remotely, stored permanently, stored temporarily) and may be retrieved. The ID may be associated with at least one record, account, user, household, address, phone number, social security number, customer number, another ID, another identifier, timestamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be person, user, subject, passenger, child, older person, baby, sleeping baby, baby in vehicle, patient, worker, high-value worker, expert, specialist, waiter, customer in mall, traveler in airport/train station/bus terminal/shipping terminals, staff/worker/customer service personnel in factory/mall/supermarket/office/workplace, serviceman in sewage/air ventilation system/lift well, lifts in lift wells, elevator, inmate, people to be tracked/monitored, animal, plant, living object, pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in warehouse/store/supermarket/distribution center, boat, bicycle, airplane, drone, remote control car/plane/boat, robot, manufacturing device, assembly line, material/unfinished part/robot/wagon/transports on factory floor, object to be tracked in airport/shopping mart/supermarket, non-object, absence of an object, presence of an object, object with form, object with changing form, object with no form, mass of fluid, mass of liquid, mass of gas/smoke, fire, flame, electromagnetic (EM) source, EM medium, and/or another object. The object itself may be communicatively coupled with some network, such as WiFi, MiFi, 3G/4G/LTE/5G/6G/7G, Bluetooth, NFC, BLE, WiMax, Zigbee, UMTS, 3GPP, GSM, EDGE, TDMA, FDMA, CDMA, WCDMA, TD-SCDMA, mesh network, adhoc network, and/or other network. The object itself may be bulky with AC power supply, but is moved during installation, cleaning, maintenance, renovation, etc. It may also be installed in moveable platform such as lift, pad, movable, platform, elevator, conveyor belt, robot, drone, forklift, car, boat, vehicle, etc. The object may have multiple parts, each part with different movement (e.g. change in position/location). For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit TSCI and/or information associated with the TSCI to the nearby device, and/or each other. They may be with the nearby device. The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, local server (e.g. hub device) and/or other server via internet, wired internet connection and/or wireless internet connection. The nearby device may be portable. The portable device, the nearby device, a local server (e.g. hub device) and/or a cloud server may share the computation and/or storage for a task (e.g. obtain TSCI, determine characteristics/STI of the object associated with the movement (e.g. change in position/location) of the object, computation of time series of power (e.g. signal strength) information, determining/computing the particular function, searching for local extremum, classification, identifying particular value of time offset, denoising, processing, simplification, cleaning, wireless smart sensing task, extract CI from signal, switching, segmentation, estimate trajectory/path/track, process the map, processing trajectory/path/track based on environment models/constraints/limitations, correction, corrective adjustment, adjustment, map-based (or model-based) correction, detecting error, checking for boundary hitting, thresholding) and information (e.g. TSCI). The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, network enabled device, device with connection to WiFi/3G/4G/5G/6G/Zigbee/Bluetooth/NFC/UMTS/3GPP/GSM/EDGE/TDMA/FDMA/CDMA/WCDMA/TD-SCDMA/adhoc network/other network, smart speaker, smart watch, smart clock, smart appliance, smart machine, smart equipment, smart tool, smart vehicle, internet-of-thing (IoT) device, internet-enabled device, computer, portable computer, tablet, and another device. The nearby device and/or at least one processor associated with the wireless receiver, the wireless transmitter, the another wireless receiver, the another wireless transmitter and/or a cloud server (in the cloud) may determine the initial STI of the object. Two or more of them may determine the initial spatial-temporal info jointly. Two or more of them may share intermediate information in the determination of the initial STI (e.g. initial position).

In one example, the wireless transmitter (e.g. Type 1 device, or Tracker Bot) may move with the object. The wireless transmitter may send the signal to the wireless receiver (e.g. Type 2 device, or Origin Register) or determining the initial STI (e.g. initial position) of the object. The wireless transmitter may also send the signal and/or another signal to another wireless receiver (e.g. another Type 2 device, or another Origin Register) for the monitoring of the motion (spatial-temporal info) of the object. The wireless receiver may also receive the signal and/or another signal from the wireless transmitter and/or the another wireless transmitter for monitoring the motion of the object. The location of the wireless receiver and/or the another wireless receiver may be known. In another example, the wireless receiver (e.g. Type 2 device, or Tracker Bot) may move with the object. The wireless receiver may receive the signal transmitted from the wireless transmitter (e.g. Type 1 device, or Origin Register) for determining the initial spatial-temporal info (e.g. initial position) of the object. The wireless receiver may also receive the signal and/or another signal from another wireless transmitter (e.g. another Type 1 device, or another Origin Register) for the monitoring of the current motion (e.g. spatial-temporal info) of the object. The wireless transmitter may also transmit the signal and/or another signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a sensing area, room, house, office, property, workplace, hallway, walkway, lift, lift well, escalator, elevator, sewage system, air ventilations system, staircase, gathering area, duct, air duct, pipe, tube, enclosed space, enclosed structure, semi-enclosed structure, enclosed area, area with at least one wall, plant, machine, engine, structure with wood, structure with glass, structure with metal, structure with walls, structure with doors, structure with gaps, structure with reflection surface, structure with fluid, building, rooftop, store, factory, assembly line, hotel room, museum, classroom, school, university, government building, warehouse, garage, mall, airport, train station, bus terminal, hub, transportation hub, shipping terminal, government facility, public facility, school, university, entertainment facility, recreational facility, hospital, pediatric/neonatal wards, seniors home, elderly care facility, geriatric facility, community center, stadium, playground, park, field, sports facility, swimming facility, track and/or field, basketball court, tennis court, soccer stadium, baseball stadium, gymnasium, hall, garage, shopping mart, mall, supermarket, manufacturing facility, parking facility, construction site, mining facility, transportation facility, highway, road, valley, forest, wood, terrain, landscape, den, patio, land, path, amusement park, urban area, rural area, suburban area, metropolitan area, garden, square, plaza, music hall, downtown facility, over-air facility, semi-open facility, closed area, train platform, train station, distribution center, warehouse, store, distribution center, storage facility, underground facility, space (e.g. above ground, outer-space) facility, floating facility, cavern, tunnel facility, indoor facility, open-air facility, outdoor facility with some walls/doors/reflective barriers, open facility, semi-open facility, car, truck, bus, van, container, ship/boat, submersible, train, tram, airplane, vehicle, mobile home, cave, tunnel, pipe, channel, metropolitan area, downtown area with relatively tall buildings, valley, well, duct, pathway, gas line, oil line, water pipe, network of interconnecting pathways/alleys/roads/tubes/cavities/caves/pipe-like structure/air space/fluid space, human body, animal body, body cavity, organ, bone, teeth, soft tissue, hard tissue, rigid tissue, non-rigid tissue, blood/body fluid vessel, windpipe, air duct, den, etc. The venue may be indoor space, outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a connection (e.g. Bluetooth, Bluetooth Low Energy (BLE), WiFi, LTE, NFC, ZigBee). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, access point, mobile WiFi (MiFi), dongle with USB/micro USB/Firewire/other connector, smartphone, portable computer, computer, tablet, smart device, internet-of-thing (IoT) device, WiFi-enabled device, LTE-enabled device, a smart watch, smart glass, smart mirror, smart antenna, smart battery, smart light, smart pen, smart ring, smart door, smart window, smart clock, small battery, smart wallet, smart belt, smart handbag, smart clothing/garment, smart ornament, smart packaging, smart paper/book/magazine/poster/printed matter/signage/display/lighted system/lighting system, smart key/tool, smart bracelet/chain/necklace/wearable/accessory, smart pad/cushion, smart tile/block/brick/building material/other material, smart garbage can/waste container, smart food carriage/storage, smart ball/racket, smart chair/sofa/bed, smart shoe/footwear/carpet/mat/shoe rack, smart glove/hand wear/ring/hand ware, smart hat/headwear/makeup/sticker/tattoo, smart mirror, smart toy, smart pill, smart utensil, smart bottle/food container, smart tool, smart device, IoT device, WiFi enabled device, network enabled device, 3G/4G/5G/6G enabled device, UMTS devices, 3GPP devices, GSM devices, EDGE devices, TDMA devices, FDMA devices, CDMA devices, WCDMA devices, TD-SCDMA devices, embeddable device, implantable device, air conditioner, refrigerator, heater, furnace, furniture, oven, cooking device, television/set-top box (STB)/DVD player/audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools/garbage can/container, 20-ft/40-ft container, storage container, factory/manufacturing/production device, repair tools, fluid container, machine, machinery to be installed, vehicle, cart, wagon, warehouse vehicle, car, bicycle, motorcycle, boat, vessel, airplane, basket/box/bag/bucket/container, smart plate/cup/bowl/pot/mat/utensils/kitchen tools/kitchen devices/kitchen accessories/cabinets/tables/chairs/tiles/lights/water pipes/taps/gas range/oven/dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID)/identifier as described above.

An event may be monitored based on the TSCI. The event may be an object related event, such as fall-down of the object (e.g. an person and/or a sick person), rotation, hesitation, pause, impact (e.g. a person hitting a sandbag, door, window, bed, chair, table, desk, cabinet, box, another person, animal, bird, fly, table, chair, ball, bowling ball, tennis ball, football, soccer ball, baseball, basketball, volley ball), two-body action (e.g. a person letting go a balloon, catching a fish, molding a clay, writing a paper, person typing on a computer), car moving in a garage, person carrying a smart phone and walking around an airport/mall/government building/office/etc., autonomous moveable object/machine moving around (e.g. vacuum cleaner, utility vehicle, car, drone, self-driving car). The task or the wireless smart sensing task may comprise: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, human breathing detection, human breathing recognition, human breathing estimation, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/correction, irregularity detection, locationing, room sensing, tracking, multiple object tracking, indoor tracking, indoor position, indoor navigation, energy management, power transfer, wireless power transfer, object counting, car tracking in parking garage, activating a device/system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server (e.g. hub device), edge server, a cloud server, and/or another device. The task may be based on TSCI between any pair of Type 1 device and Type 2 device. A Type 2 device may be a Type 1 device, and vice versa. A Type 2 device may play/perform the role (e.g. functionality) of Type 1 device temporarily, continuously, sporadically, simultaneously, and/or contemporaneously, and vice versa. A first part of the task may comprise at least one of: preprocessing, processing, signal conditioning, signal processing, post-processing, processing sporadically/continuously/simultaneously/contemporaneously/dynamically/adaptive/on-demand/as-needed, calibrating, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, repeated motion detection/estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder (and/or illegal action) detection, baby detection, baby monitoring, patient monitoring, object recognition, wireless power transfer, and/or wireless charging.

A second part of the task may comprise at least one of: a smart home task, smart office task, smart building task, smart factory task (e.g. manufacturing using a machine or an assembly line), smart internet-of-thing (IoT) task, smart system task, smart home operation, smart office operation, smart building operation, smart manufacturing operation (e.g. moving supplies/parts/raw material to a machine/an assembly line), IoT operation, smart system operation, turning on a light, turning off the light, controlling the light in at least one of: a room, region, and/or the venue, playing a sound clip, playing the sound clip in at least one of: the room, the region, and/or the venue, playing the sound clip of at least one of: a welcome, greeting, farewell, first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, heating system, ventilation system, lighting system, heating device, stove, entertainment system, door, fence, window, garage, computer system, networked device, networked system, home appliance, office equipment, lighting device, robot (e.g. robotic arm), smart vehicle, smart machine, assembly line, smart device, internet-of-thing (IoT) device, smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room), monitor/detect location of a user/pet, do something (e.g. send a message, notify/report to someone) automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/ speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/appliance/material/furniture/fixture, using web tool/server/hub device/cloud server/fog server/edge server/home network/mesh network, using messaging tool/notification tool/communication tool/scheduling tool/email, using user interface/GUI, using scent/smell/fragrance/taste, using neural tool/nervous system tool, using a combination) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc. Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, resting motion, non-moving motion, movement, change in position/location, deterministic motion, transient motion, fall-down motion, repeating motion, periodic motion, pseudo-periodic motion, periodic/repeated motion associated with breathing, periodic/repeated motion associated with heartbeat, periodic/repeated motion associated with living object, periodic/repeated motion associated with machine, periodic/repeated motion associated with man-made object, periodic/repeated motion associated with nature, complex motion with transient element and periodic element, repetitive motion, non-deterministic motion, probabilistic motion, chaotic motion, random motion, complex motion with non-deterministic element and deterministic element, stationary random motion, pseudo-stationary random motion, cyclo-stationary random motion, non-stationary random motion, stationary random motion with periodic autocorrelation function (ACF), random motion with periodic ACF for period of time, random motion that is pseudo-stationary for a period of time, random motion of which an instantaneous ACF has a pseudo-periodic/repeating element for a period of time, machine motion, mechanical motion, vehicle motion, drone motion, air-related motion, wind-related motion, weather-related motion, water-related motion, fluid-related motion, ground-related motion, change in electro-magnetic characteristics, subsurface motion, seismic motion, plant motion, animal motion, human motion, normal motion, abnormal motion, dangerous motion, warning motion, suspicious motion, rain, fire, flood, tsunami, explosion, collision, imminent collision, human body motion, head motion, facial motion, eye motion, mouth motion, tongue motion, neck motion, finger motion, hand motion, arm motion, shoulder motion, body motion, chest motion, abdominal motion, hip motion, leg motion, foot motion, body joint motion, knee motion, elbow motion, upper body motion, lower body motion, skin motion, below-skin motion, subcutaneous tissue motion, blood vessel motion, intravenous motion, organ motion, heart motion, lung motion, stomach motion, intestine motion, bowel motion, eating motion, breathing motion, facial expression, eye expression, mouth expression, talking motion, singing motion, eating motion, gesture, hand gesture, arm gesture, keystroke, typing stroke, user-interface gesture, man-machine interaction, gait, dancing movement, coordinated movement, and/or coordinated body movement.

The heterogeneous IC of the Type 1 device and/or any Type 2 receiver may comprise low-noise amplifier (LNA), power amplifier, transmit-receive switch, media access controller, baseband radio, 2.4 GHz radio, 3.65 GHz radio, 4.9 GHz radio, 5 GHz radio, 5.9 GHz radio, below 6 GHz radio, below 60 GHz radio and/or another radio. The heterogeneous IC may comprise a processor, a memory communicatively coupled with the processor, and a set of instructions stored in the memory to be executed by the processor. The IC and/or any processor may comprise at least one of: general purpose processor, special purpose processor, microprocessor, multi-processor, multi-core processor, parallel processor, CISC processor, RISC processor, microcontroller, central processing unit (CPU), graphical processor unit (GPU), digital signal processor (DSP), application specific integrated circuit (ASIC), field programmable gate array (FPGA), embedded processor (e.g. ARM), logic circuit, other programmable logic device, discrete logic, and/or a combination. The heterogeneous IC may support broadband network, wireless network, mobile network, mesh network, cellular network, wireless local area network (WLAN), wide area network (WAN), and metropolitan area network (MAN), WLAN standard, WiFi, LTE, LTE-A, LTE-U, 802.11 standard, 802.11a, 802.11b, 802.11g, 802.11n, 802.11ac, 802.11ad, 802.11af, 802.11ah, 802.11ax, 802.11ay, mesh network standard, 802.15 standard, 802.16 standard, cellular network standard, 3G, 3.5G, 4G, beyond 4G, 4.5G, 5G, 6G, 7G, 8G, 9G, UMTS, 3GPP, GSM, EDGE, TDMA, FDMA, CDMA, WCDMA, TD-SCDMA, Bluetooth, Bluetooth Low-Energy (BLE), NFC, Zigbee, WiMax, and/or another wireless network protocol.

The processor may comprise general purpose processor, special purpose processor, microprocessor, microcontroller, embedded processor, digital signal processor, central processing unit (CPU), graphical processing unit (GPU), multiprocessor, multi-core processor, and/or processor with graphics capability, and/or a combination. The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, magnetic storage, optical storage, organic storage, storage system, storage network, network storage, cloud storage, edge storage, local storage, external storage, internal storage, or other form of non-transitory storage medium known in the art. The set of instructions (machine executable code) corresponding to the method steps may be embodied directly in hardware, in software, in firmware, or in combinations thereof. The set of instructions may be embedded, pre-loaded, loaded upon boot up, loaded on the fly, loaded on demand, pre-installed, installed, and/or downloaded.

The presentation may be a presentation in an audio-visual way (e.g. using combination of visual, graphics, text, symbols, color, shades, video, animation, sound, speech, audio, etc.), graphical way (e.g. using GUI, animation, video), textual way (e.g. webpage with text, message, animated text), symbolic way (e.g. emoticon, signs, hand gesture), or mechanical way (e.g. vibration, actuator movement, haptics, etc.).

Computational workload associated with the method is shared among the processor, the Type 1 heterogeneous wireless device, the Type 2 heterogeneous wireless device, a local server (e.g. hub device), a cloud server, and another processor.

An operation, pre-processing, processing and/or postprocessing may be applied to data (e.g. TSCI, autocorrelation, features of TSCI). An operation may be preprocessing, processing and/or postprocessing. The preprocessing, processing and/or postprocessing may be an operation. An operation may comprise preprocessing, processing, post-processing, scaling, computing a confidence factor, computing a line-of-sight (LOS) quantity, computing a non-LOS (NLOS) quantity, a quantity comprising LOS and NLOS, computing a single link (e.g. path, communication path, link between a transmitting antenna and a receiving antenna) quantity, computing a quantity comprising multiple links, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, inverse transform, frequency transform, inverse frequency transform, Fourier transform (FT), discrete time FT (DTFT), discrete FT (DFT), fast FT (FFT), wavelet transform, Laplace transform, Hilbert transform, Hadamard transform, trigonometric transform, sine transform, cosine transform, DCT, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another TSCI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and/or another operation. The operation may be the preprocessing, processing, and/or post-processing. Operations may be applied jointly on multiple time series or functions.

The function (e.g. function of operands) may comprise: scalar function, vector function, discrete function, continuous function, polynomial function, characteristics, feature, magnitude, phase, exponential function, logarithmic function, trigonometric function, transcendental function, logical function, linear function, algebraic function, nonlinear function, piecewise linear function, real function, complex function, vector-valued function, inverse function, derivative of function, integration of function, circular function, function of another function, one-to-one function, one-to-many function, many-to-one function, many-to-many function, zero crossing, absolute function, indicator function, mean, mode, median, range, statistics, histogram, variance, standard deviation, measure of variation, spread, dispersion, deviation, divergence, range, interquartile range, total variation, absolute deviation, total deviation, arithmetic mean, geometric mean, harmonic mean, trimmed mean, percentile, square, cube, root, power, sine, cosine, tangent, cotangent, secant, cosecant, elliptical function, parabolic function, hyperbolic function, game function, zeta function, absolute value, thresholding, limiting function, floor function, rounding function, sign function, quantization, piecewise constant function, composite function, function of function, time function processed with an operation (e.g. filtering), probabilistic function, stochastic function, random function, ergodic function, stationary function, deterministic function, periodic function, repeated function, transformation, frequency transform, inverse frequency transform, discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, moving function, function of moving window of neighboring items of time series, filtering function, convolution, mean function, histogram, variance/standard deviation function, statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, identifying a class/group/category, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, down-converting, upsampling, up-converting, interpolation, extrapolation, importance sampling, Monte Carlo sampling, compressive sensing, statistics, short term statistics, long term statistics, autocorrelation function, cross correlation, moment generating function, time averaging, weighted averaging, special function, Bessel function, error function, complementary error function, Beta function, Gamma function, integral function, Gaussian function, Poisson function, etc. Machine learning, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

A quantity/feature from a TSCI may be computed. The quantity may comprise statistic of at least one of: motion, location, map coordinate, height, speed, acceleration, movement angle, rotation, size, volume, time trend, pattern, one-time pattern, repeating pattern, evolving pattern, time pattern, mutually excluding patterns, related/correlated patterns, cause-and-effect, correlation, short-term/long-term correlation, tendency, inclination, statistics, typical behavior, atypical behavior, time trend, time profile, periodic motion, repeated motion, repetition, tendency, change, abrupt change, gradual change, frequency, transient, breathing, gait, action, event, suspicious event, dangerous event, alarming event, warning, belief, proximity, collision, power, signal, signal power, signal strength, signal intensity, received signal strength indicator (RSSI), signal amplitude, signal phase, signal frequency component, signal frequency band component, channel state information (CSI), map, time, frequency, time-frequency, decomposition, orthogonal decomposition, non-orthogonal decomposition, tracking, breathing, heart beat, statistical parameters, cardiopulmonary statistics/analytics (e.g. output responses), daily activity statistics/analytics, chronic disease statistics/analytics, medical statistics/analytics, an early (or instantaneous or contemporaneous or delayed) indication/suggestion/sign/indicator/verifier/detection/symptom of a disease/condition/situation, biometric, baby, patient, machine, device, temperature, vehicle, parking lot, venue, lift, elevator, spatial, road, fluid flow, home, room, office, house, building, warehouse, storage, system, ventilation, fan, pipe, duct, people, human, car, boat, truck, airplane, drone, downtown, crowd, impulsive event, cyclo-stationary, environment, vibration, material, surface, 3-dimensional, 2-dimensional, local, global, presence, and/or another measurable quantity/variable.

Sliding time window may have time varying window width. It may be smaller at the beginning to enable fast acquisition and may increase over time to a steady-state size. The steady-state size may be related to the frequency, repeated motion, transient motion, and/or STI to be monitored. Even in steady state, the window size may be adaptively (and/or dynamically) changed (e.g. adjusted, varied, modified) based on battery life, power consumption, available computing power, change in amount of targets, the nature of motion to be monitored, etc.

The time shift between two sliding time windows at adjacent time instance may be constant/variable/locally adaptive/dynamically adjusted over time. When shorter time shift is used, the update of any monitoring may be more frequent which may be used for fast changing situations, object motions, and/or objects. Longer time shift may be used for slower situations, object motions, and/or objects. The window width/size and/or time shift may be changed (e.g. adjusted, varied, modified) upon a user request/choice. The time shift may be changed automatically (e.g. as controlled by processor/computer/server/hub device/cloud server) and/or adaptively (and/or dynamically).

At least one characteristics (e.g. characteristic value, or characteristic point) of a function (e.g. auto-correlation function, auto-covariance function, cross-correlation function, cross-covariance function, power spectral density, time function, frequency domain function, frequency transform) may be determined (e.g. by an object tracking server, the processor, the Type I heterogeneous device, the Type 2 heterogeneous device, and/or another device). The at least one characteristics of the function may include: a maximum, minimum, extremum, local maximum, local minimum, local extremum, local extremum with positive time offset, first local extremum with positive time offset, n^th local extremum with positive time offset, local extremum with negative time offset, first local extremum with negative time offset, n^th local extremum with negative time offset, constrained maximum, constrained minimum, constrained extremum, significant maximum, significant minimum, significant extremum, slope, derivative, higher order derivative, maximum slope, minimum slope, local maximum slope, local maximum slope with positive time offset, local minimum slope, constrained maximum slope, constrained minimum slope, maximum higher order derivative, minimum higher order derivative, constrained higher order derivative, zero-crossing, zero crossing with positive time offset, n^th zero crossing with positive time offset, zero crossing with negative time offset, n^th zero crossing with negative time offset, constrained zero-crossing, zero-crossing of slope, zero-crossing of higher order derivative, and/or another characteristics. At least one argument of the function associated with the at least one characteristics of the function may be identified. Some quantity (e.g. spatial-temporal information of the object) may be determined based on the at least one argument of the function.

A characteristics (e.g. characteristics of motion of an object in the venue) may comprise at least one of: an instantaneous characteristics, short-term characteristics, repetitive characteristics, recurring characteristics, history, incremental characteristics, changing characteristics, deviational characteristics, phase, magnitude, degree, time characteristics, frequency characteristics, time-frequency characteristics, decomposition characteristics, orthogonal decomposition characteristics, non-orthogonal decomposition characteristics, deterministic characteristics, probabilistic characteristics, stochastic characteristics, autocorrelation function (ACF), mean, variance, standard deviation, measure of variation, spread, dispersion, deviation, divergence, range, interquartile range, total variation, absolute deviation, total deviation, statistics, duration, timing, trend, periodic characteristics, repetition characteristics, long-term characteristics, historical characteristics, average characteristics, current characteristics, past characteristics, future characteristics, predicted characteristics, location, distance, height, speed, direction, velocity, acceleration, change of the acceleration, angle, angular speed, angular velocity, angular acceleration of the object, change of the angular acceleration, orientation of the object, angular of rotation, deformation of the object, shape of the object, change of shape of the object, change of size of the object, change of structure of the object, and/or change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, monotonic function) of a fraction of a quantity (e.g. power, magnitude) of the local maximum over the same quantity of the local minimum. It may also be the function of a difference between the quantity of the local maximum and the same quantity of the local minimum. Significant local peaks may be identified or selected. Each significant local peak may be a local maximum with SNR-like parameter greater than a threshold T1 and/or a local maximum with amplitude greater than a threshold T2. The at least one local minimum and the at least one local minimum in the frequency domain may be identified/computed using a persistence-based approach.

A set of selected significant local peaks may be selected from the set of identified significant local peaks based on a selection criterion (e.g. a quality criterion, a signal quality condition). The characteristics/STI of the object may be computed based on the set of selected significant local peaks and frequency values associated with the set of selected significant local peaks. In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time. For example, if a finite state machine (FSM) is used, it may select the peak(s) based on the state of the FSM. Decision thresholds may be computed adaptively (and/or dynamically) based on the state of the FSM.

A similarity score and/or component similarity score may be computed (e.g. by a server (e.g. hub device), the processor, the Type 1 device, the Type 2 device, a local server, a cloud server, and/or another device) based on a pair of temporally adjacent CI of a TSCI. The pair may come from the same sliding window or two different sliding windows. The similarity score may also be based on a pair of, temporally adjacent or not so adjacent, CI from two different TSCI. The similarity score and/or component similar score may be/comprise: time reversal resonating strength (TRRS), correlation, cross-correlation, auto-correlation, correlation indicator, covariance, cross-covariance, auto-covariance, inner product of two vectors, distance score, norm, metric, quality metric, signal quality condition, statistical characteristics, discrimination score, neural network, deep learning network, machine learning, training, discrimination, weighted averaging, preprocessing, denoising, signal conditioning, filtering, time correction, timing compensation, phase offset compensation, transformation, component-wise operation, feature extraction, finite state machine, and/or another score. The characteristics and/or STI may be determined/computed based on the similarity score.

Any threshold may be pre-determined, adaptively (and/or dynamically) determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI), power parameter) may be collected under A and/or under B in a training situation. The test statistics may be computed based on the data. Distributions of the test statistics under A may be compared with distributions of the test statistics under B (reference distribution), and the threshold may be chosen according to some criteria. The criteria may comprise: maximum likelihood (ML), maximum aposterior probability (MAP), discriminative training, minimum Type 1 error for a given Type 2 error, minimum Type 2 error for a given Type 1 error, and/or other criteria (e.g. a quality criterion, signal quality condition).

The threshold may be adjusted to achieve different sensitivity to the A, B and/or another event/condition/situation/state.

The threshold adjustment may be automatic, semi-automatic and/or manual. The threshold adjustment may be applied once, sometimes, often, periodically, repeatedly, occasionally, sporadically, and/or on demand. The threshold adjustment may be adaptive (and/or dynamically adjusted). The threshold adjustment may depend on the object, object movement/location/direction/action, object characteristics/STI/size/property/trait/habit/behavior, the venue, feature/fixture/furniture/barrier/material/machine/living thing/thing/object/boundary/surface/medium that is in/at/of the venue, map, constraint of the map (or environmental model), the event/state/situation/condition, time, timing, duration, current state, past history, user, and/or a personal preference, etc.

A stopping criterion (or skipping or bypassing or blocking or pausing or passing or rejecting criterion) of an iterative algorithm may be that change of a current parameter (e.g. offset value) in the updating in an iteration is less than a threshold. The threshold may be 0.5, 1, 1.5, 2, or another number. The threshold may be adaptive (and/or dynamically adjusted). It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise robust search, minimization, maximization, optimization, statistical optimization, dual optimization, constraint optimization, convex optimization, global optimization, local optimization an energy minimization, linear regression, quadratic regression, higher order regression, linear programming, nonlinear programming, stochastic programming, combinatorial optimization, constraint programming, constraint satisfaction, calculus of variations, optimal control, dynamic programming, mathematical programming, multi-objective optimization, multi-modal optimization, disjunctive programming, space mapping, infinite-dimensional optimization, heuristics, metaheuristics, convex programming, semidefinite programming, conic programming, cone programming, integer programming, quadratic programming, fractional programming, numerical analysis, simplex algorithm, iterative method, gradient descent, subgradient method, coordinate descent, conjugate gradient method, Newton's algorithm, sequential quadratic programming, interior point method, ellipsoid method, reduced gradient method, quasi-Newton method, simultaneous perturbation stochastic approximation, interpolation method, pattern search method, line search, non-differentiable optimization, genetic algorithm, evolutionary algorithm, dynamic relaxation, hill climbing, particle swarm optimization, gravitation search algorithm, simulated annealing, memetic algorithm, differential evolution, dynamic relaxation, stochastic tunneling, Tabu search, reactive search optimization, curve fitting, least square, simulation based optimization, variational calculus, and/or variant. The search for local extremum may be associated with an objective function, loss function, cost function, utility function, fitness function, energy function, and/or an energy function.

Regression may be performed using regression function to fit sampled data (e.g. CI, feature of CI, component of CI) or another function (e.g. autocorrelation function) in a regression window. In at least one iteration, a length of the regression window and/or a location of the regression window may change. The regression function may be linear function, quadratic function, cubic function, polynomial function, and/or another function. The regression analysis may minimize at least one of: error, aggregate error, component error, error in projection domain, error in selected axes, error in selected orthogonal axes, absolute error, square error, absolute deviation, square deviation, higher order error (e.g. third order, fourth order), robust error (e.g. square error for smaller error magnitude and absolute error for larger error magnitude, or first kind of error for smaller error magnitude and second kind of error for larger error magnitude), another error, weighted sum (or weighted mean) of absolute/square error (e.g. for wireless transmitter with multiple antennas and wireless receiver with multiple antennas, each pair of transmitter antenna and receiver antenna form a link), mean absolute error, mean square error, mean absolute deviation, and/or mean square deviation. Error associated with different links may have different weights. One possibility is that some links and/or some components with larger noise or lower signal quality metric may have smaller or bigger weight), weighted sum of square error, weighted sum of higher order error, weighted sum of robust error, weighted sum of the another error, absolute cost, square cost, higher order cost, robust cost, another cost, weighted sum of absolute cost, weighted sum of square cost, weighted sum of higher order cost, weighted sum of robust cost, and/or weighted sum of another cost. The regression error determined may be an absolute error, square error, higher order error, robust error, yet another error, weighted sum of absolute error, weighted sum of square error, weighted sum of higher order error, weighted sum of robust error, and/or weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, square error, higher order error, robust error, another error, weighted sum of absolute error, weighted sum of square error, weighted sum of higher order error, weighted sum of robust error, and/or weighted sum of the another error.

The quantity may be compared with a reference data or a reference distribution, such as an F-distribution, central F-distribution, another statistical distribution, threshold, threshold associated with probability/histogram, threshold associated with probability/histogram of finding false peak, threshold associated with the F-distribution, threshold associated the central F-distribution, and/or threshold associated with the another statistical distribution.

The regression window may be determined based on at least one of: the movement (e.g. change in position/location) of the object, quantity associated with the object, the at least one characteristics and/or STI of the object associated with the movement of the object, estimated location of the local extremum, noise characteristics, estimated noise characteristics, signal quality metric, F-distribution, central F-distribution, another statistical distribution, threshold, preset threshold, threshold associated with probability/histogram, threshold associated with desired probability, threshold associated with probability of finding false peak, threshold associated with the F-distribution, threshold associated the central F-distribution, threshold associated with the another statistical distribution, condition that quantity at the window center is largest within the regression window, condition that the quantity at the window center is largest within the regression window, condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, target profile, trend, past trend, current trend, target speed, speed profile, target speed profile, past speed trend, the motion or movement (e.g. change in position/location) of the object, at least one characteristics and/or STI of the object associated with the movement of object, positional quantity of the object, initial speed of the object associated with the movement of the object, predefined value, initial width of the regression window, time duration, value based on carrier frequency of the signal, value based on subcarrier frequency of the signal, bandwidth of the signal, amount of antennas associated with the channel, noise characteristics, signal h metric, and/or an adaptive (and/or dynamically adjusted) value. The current time offset may be at the center, on the left side, on the right side, and/or at another fixed relative location, of the regression window.

In the presentation, information may be displayed with a map (or environmental model) of the venue. The information may comprise: location, zone, region, area, coverage area, corrected location, approximate location, location with respect to (w.r.t.) a map of the venue, location w.r.t. a segmentation of the venue, direction, path, path w.r.t. the map and/or the segmentation, trace (e.g. location within a time window such as the past 5 seconds, or past 10 seconds; the time window duration may be adjusted adaptively (and/or dynamically); the time window duration may be adaptively (and/or dynamically) adjusted w.r.t. speed, acceleration, etc.), history of a path, approximate regions/zones along a path, history/summary of past locations, history of past locations of interest, frequently-visited areas, customer traffic, crowd distribution, crowd behavior, crowd control information, speed, acceleration, motion statistics, breathing rate, heart rate, presence/absence of motion, presence/absence of people or pets or object, presence/absence of vital sign, gesture, gesture control (control of devices using gesture), location-based gesture control, information of a location-based operation, identity (ID) or identifier of the respect object (e.g. pet, person, self-guided machine/device, vehicle, drone, car, boat, bicycle, self-guided vehicle, machine with fan, air-conditioner, TV, machine with movable part), identification of a user (e.g. person), information of the user, location/speed/acceleration/direction/motion/gesture/gesture control/motion trace of the user, ID or identifier of the user, activity of the user, state of the user, sleeping/resting characteristics of the user, emotional state of the user, vital sign of the user, environment information of the venue, weather information of the venue, earthquake, explosion, storm, rain, fire, temperature, collision, impact, vibration, event, door-open event, door-close event, window-open event, window-close event, fall-down event, burning event, freezing event, water-related event, wind-related event, air-movement event, accident event, pseudo-periodic event (e.g. running on treadmill, jumping up and down, skipping rope, somersault, etc.), repeated event, crowd event, vehicle event, gesture of the user (e.g. hand gesture, arm gesture, foot gesture, leg gesture, body gesture, head gesture, face gesture, mouth gesture, eye gesture, etc.). The location may be 2-dimensional (e.g. with 2D coordinates), 3-dimensional (e.g. with 3D coordinates). The location may be relative (e.g. w.r.t. a map or environmental model) or relational (e.g. halfway between point A and point B, around a corner, up the stairs, on top of table, at the ceiling, on the floor, on a sofa, close to point A, a distance R from point A, within a radius of R from point A, etc.). The location may be expressed in rectangular coordinate, polar coordinate, and/or another representation.

The information (e.g. location) may be marked with at least one symbol. The symbol may be time varying. The symbol may be flashing and/or pulsating with or without changing color/intensity. The size may change over time. The orientation of the symbol may change over time. The symbol may be a number that reflects an instantaneous quantity (e.g. vital sign/breathing rate/heart rate/gesture/state/status/action/motion of a user, temperature, network traffic, network connectivity, status of a device/machine, remaining power of a device, status of the device, etc.). The rate of change, the size, the orientation, the color, the intensity and/or the symbol may reflect the respective motion. The information may be presented visually and/or described verbally (e.g. using pre-recorded voice, or voice synthesis). The information may be described in text. The information may also be presented in a mechanical way (e.g. an animated gadget, a movement of a movable part).

The user-interface (UI) device may be a smart phone (e.g. iPhone, Android phone), tablet (e.g. iPad), laptop (e.g. notebook computer), personal computer (PC), device with graphical user interface (GUI), smart speaker, device with voice/audio/speaker capability, virtual reality (VR) device, augmented reality (AR) device, smart car, display in the car, voice assistant, voice assistant in a car, etc. The map (or environmental model) may be 2-dimensional, 3-dimensional and/or higher-dimensional. (e.g. a time varying 2D/3D map/environmental model) Walls, windows, doors, entrances, exits, forbidden areas may be marked on the map or the model.

The map may comprise floor plan of a facility. The map or model may have one or more layers (overlays). The map/model may be a maintenance map/model comprising water pipes, gas pipes, wiring, cabling, air ducts, crawl-space, ceiling layout, and/or underground layout. The venue may be segmented/subdivided/zoned/grouped into multiple zones/regions/geographic regions/sectors/sections/territories/districts/precincts/localities/neighborhoods/areas/stretches/expanse such as bedroom, living room, storage room, walkway, kitchen, dining room, foyer, garage, first floor, second floor, rest room, offices, conference room, reception area, various office areas, various warehouse regions, various facility areas, etc. The segments/regions/areas may be presented in a map/model. Different regions may be color-coded. Different regions may be presented with a characteristic (e.g. color, brightness, color intensity, texture, animation, flashing, flashing rate, etc.). Logical segmentation of the venue may be done using the at least one heterogeneous Type 2 device, or a server (e.g. hub device), or a cloud server, etc.

Here is an example of the disclosed system, apparatus, and method. Stephen and his family want to install the disclosed wireless motion detection system to detect motion in their 2000 sqft two-storey town house in Seattle, Wash. Because his house has two storeys, Stephen decided to use one Type 2 device (named A) and two Type 1 devices (named B and C) in the ground floor. His ground floor has predominantly three rooms: kitchen, dining room and living room arranged in a straight line, with the dining room in the middle. The kitchen and the living rooms are on opposite end of the house. He put the Type 2 device (A) in the dining room, and put one Type 1 device (B) in the kitchen and the other Type 1 device (C) in the living room. With this placement of the devices, he is practically partitioning the ground floor into 3 zones (dining room, living room and kitchen) using the motion detection system. When motion is detected by the AB pair and the AC pair, the system would analyze the motion information and associate the motion with one of the 3 zones.

When Stephen and his family go out on weekends (e.g. to go for a camp during a long weekend), Stephen would use a mobile phone app (e.g. Android phone app or iPhone app) to turn on the motion detection system. When the system detects motion, a warning signal is sent to Stephen (e.g. an SMS text message, an email, a push message to the mobile phone app, etc.). If Stephen pays a monthly fee (e.g. $10/month), a service company (e.g. security company) will receive the warning signal through wired network (e.g. broadband) or wireless network (e.g. home WiFi, LTE, 3G, 2.5G, etc.) and perform a security procedure for Stephen (e.g. call him to verify any problem, send someone to check on the house, contact the police on behalf of Stephen, etc.). Stephen loves his aging mother and cares about her well-being when she is alone in the house. When the mother is alone in the house while the rest of the family is out (e.g. go to work, or shopping, or go on vacation), Stephen would turn on the motion detection system using his mobile app to ensure the mother is ok. He then uses the mobile app to monitor his mother's movement in the house. When Stephen uses the mobile app to see that the mother is moving around the house among the 3 regions, according to her daily routine, Stephen knows that his mother is doing ok. Stephen is thankful that the motion detection system can help him monitor his mother's well-being while he is away from the house.

On a typical day, the mother would wake up at around 7 AM. She would cook her breakfast in the kitchen for about 20 minutes. Then she would eat the breakfast in the dining room for about 30 minutes. Then she would do her daily exercise in the living room, before sitting down on the sofa in the living room to watch her favorite TV show. The motion detection system enables Stephen to see the timing of the movement in each of the 3 regions of the house. When the motion agrees with the daily routine, Stephen knows roughly that the mother should be doing fine. But when the motion pattern appears abnormal (e.g. there is no motion until 10 AM, or she stayed in the kitchen for too long, or she remains motionless for too long, etc.), Stephen suspects something is wrong and would call the mother to check on her. Stephen may even get someone (e.g. a family member, a neighbor, a paid personnel, a friend, a social worker, a service provider) to check on his mother.

At some time, Stephen feels like repositioning the Type 2 device. He simply unplugs the device from the original AC power plug and plug it into another AC power plug. He is happy that the wireless motion detection system is plug-and-play and the repositioning does not affect the operation of the system. Upon powering up, it works right away. Sometime later, Stephen is convinced that the disclosed wireless motion detection system can really detect motion with very high accuracy and very low alarm, and he really can use the mobile app to monitor the motion in the ground floor. He decides to install a similar setup (i.e. one Type 2 device and two Type 1 devices) in the second floor to monitor the bedrooms in the second floor. Once again, he finds that the system set up is extremely easy as he simply needs to plug the Type 2 device and the Type 1 devices into the AC power plug in the second floor. No special installation is needed. And he can use the same mobile app to monitor motion in the ground floor and the second floor. Each Type 2 device in the ground floor/second floor can interact with all the Type 1 devices in both the ground floor and the second floor. Stephen is happy to see that, as he doubles his investment in the Type 1 and Type 2 devices, he has more than double the capability of the combined systems.

According to various embodiments, each CI (CI) may comprise at least one of: channel state information (CSI), frequency domain CSI, frequency representation of CSI, frequency domain CSI associated with at least one sub-band, time domain CSI, CSI in domain, channel response, estimated channel response, channel impulse response (CIR), channel frequency response (CFR), channel characteristics, channel filter response, CSI of the wireless multipath channel, information of the wireless multipath channel, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another CI. In one embodiment, the disclosed system has hardware components (e.g. wireless transmitter/receiver with antenna, analog circuitry, power supply, processor, memory) and corresponding software components. According to various embodiments of the present teaching, the disclosed system includes Bot (referred to as a Type 1 device) and Origin (referred to as a Type 2 device) for vital sign detection and monitoring. Each device comprises a transceiver, a processor and a memory.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug. etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, UMTS devices, 3GPP devices, GSM devices, EDGE devices, TDMA devices, FDMA devices, CDMA devices, WCDMA devices, TD-SCDMA devices, gaming devices, eyeglasses, glass panels, VR goggles, necklace, watch, waist band, belt, wallet, pen, hat, wearables, implantable device, tags, parking tickets, smart phones, etc.

The summary may comprise: analytics, output response, selected time window, subsampling, transform, and/or projection. The presenting may comprise presenting at least one of: monthly/weekly/daily view, simplified/detailed view, cross-sectional view, small/large form-factor view, color-coded view, comparative view, summary view, animation, web view, voice announcement, and another presentation related to the periodic/repetition characteristics of the repeating motion.

A Type 1/Type 2 device may be an antenna, a device with antenna, a device with a housing (e.g. for radio, antenna, data/signal processing unit, wireless IC, circuits), device that has interface to attach/connect to/link antenna, device that is interfaced to/attached to/connected to/linked to another device/system/computer/phone/network/data aggregator, device with a user interface (UI)/graphical UI/display, device with wireless transceiver, device with wireless transmitter, device with wireless receiver, internet-of-thing (IoT) device, device with wireless network, device with both wired networking and wireless networking capability, device with wireless integrated circuit (IC), Wi-Fi device, device with Wi-Fi chip (e.g. 802.11a/b/g/n/ac/ax standard compliant), Wi-Fi access point (AP), Wi-Fi client, Wi-Fi router, Wi-Fi repeater, Wi-Fi hub, Wi-Fi mesh network router/hub/AP, wireless mesh network router, adhoc network device, wireless mesh network device, mobile device (e.g. 2G/2.5G/3G/3.5G/4G/LTE/5G/6G/7G, UMTS, 3GPP, GSM, EDGE, TDMA, FDMA, CDMA, WCDMA, TD-SCDMA), cellular device, base station, mobile network base station, mobile network hub, mobile network compatible device, LTE device, device with LTE module, mobile module (e.g. circuit board with mobile-enabling chip (IC) such as Wi-Fi chip, LTE chip, BLE chip), Wi-Fi chip (IC), LTE chip, BLE chip, device with mobile module, smart phone, companion device (e.g. dongle, attachment, plugin) for smart phones, dedicated device, plug-in device, AC-powered device, battery-powered device, device with processor/memory/set of instructions, smart device/gadget/items: clock, stationary, pen, user-interface, paper, mat, camera, television (TV), set-top-box, microphone, speaker, refrigerator, oven, machine, phone, wallet, furniture, door, window, ceiling, floor, wall, table, chair, bed, night-stand, air-conditioner, heater, pipe, duct, cable, carpet, decoration, gadget, USB device, plug, dongle, lamp/light, tile, ornament, bottle, vehicle, car, AGV, drone, robot, laptop, tablet, computer, harddisk, network card, instrument, racket, ball, shoe, wearable, clothing, glasses, hat, necklace, food, pill, small device that moves in the body of creature (e.g. in blood vessels, in lymph fluid, digestive system), and/or another device. The Type 1 device and/or Type 2 device may be communicatively coupled with: the internet, another device with access to internet (e.g. smart phone), cloud server (e.g. hub device), edge server, local server, and/or storage. The Type 1 device and/or the Type 2 device may operate with local control, can be controlled by another device via a wired/wireless connection, can operate automatically, or can be controlled by a central system that is remote (e.g. away from home).

In one embodiment, a Type B device may be a transceiver that may perform as both Origin (a Type 2 device, a Rx device) and Bot (a Type 1 device, a Tx device), i.e., a Type B device may be both Type 1 (Tx) and Type 2 (Rx) devices (e.g. simultaneously or alternately), for example, mesh devices, a mesh router, etc. In one embodiment, a Type A device may be a transceiver that may only function as Bot (a Tx device), i.e., Type 1 device only or Tx only, e.g., simple IoT devices. It may have the capability of Origin (Type 2 device, Rx device), but somehow it is functioning only as Bot in the embodiment. All the Type A and Type B devices form a tree structure. The root may be a Type B device with network (e.g. internet) access. For example, it may be connected to broadband service through a wired connection (e.g. Ethernet, cable modem, ADSL/HDSL modem) connection or a wireless connection (e.g. LTE, 3G/4G/5G, WiFi, Bluetooth, microwave link, satellite link, etc.). In one embodiment, all the Type A devices are leaf node. Each Type B device may be the root node, non-leaf node, or leaf node.

The continuous development of 802.1 lad technology provides new opportunities in wireless sensing. The present teaching discloses ViMo, a calibration-free remote Vital sign Monitoring system that can detect stationary/non-stationary users and estimate the respiration rates (RRs) as well as heart rates (HRs) built upon a commercial 60 GHz WiFi. The design of ViMo includes two key components. First, one can design an adaptive object detector that can identify static objects, stationary human subjects and human in motion without any calibration. Second, one can devise a robust HR estimator, which eliminates the respiration signal from the phase of the channel impulse response (CIR) to remove the interference of the harmonics from breathing and adopts dynamic programming (DP) to resist the random measurement noise. The influence of different settings, including the distance between human and the device, user orientation and incidental angle, blockage material, body movement and conditions of multi-user separation are investigated by extensive experiments. Experimental results show that ViMo monitors user's vital signs accurately, with a median error of 0.19 breath per minute (BPM) and 0.92 BPM, respectively, for RR and HR estimation.

In this system, one can break down the limitation of 2.4 GHz/5 GHz WiFi by leveraging an opportunity in the emerging 60 GHz WiFi (e.g., 802.1 lad), which is already available in commercial routers. The disclosed ViMo is a first system that achieves multi-person stationary/non-stationary detection and vital signs monitoring using impulse-based commodity 60 GHz millimeter wave (mmWave) device. Different from 2.4 GHz/5 GHz radios, 60 GHz WiFi offers high directionality with large phased arrays in small size thanks to millimeter-wavelength and precise time-of-flight measurements brought by the large bandwidth. The advance in 60 GHz radios allows higher spatial resolution and range resolution, making it possible to monitor respiration as well as heart rate for multiple persons simultaneously.

However, enabling multi-person vital signs monitoring using 60 GHz WiFi is not an easy task. To achieve this goal, one may need to deal with multiple challenges. First, it is non-trivial to locate human subjects before vital sign estimation. Due to the high carrier frequency, signals attenuate rapidly over the propagation distance, making it difficult to locate distant targets. Furthermore, the automatic gain control (AGC) module on the chip changes the amplitude of the CIRs over different measurements. To address this challenge, for each measurement, one can employ two constant false alarm detectors in range and angle dimension to adaptively estimate the noise level in 3D space, and thus provide an adaptive threshold for target detection.

Second, given the reflections from multiple users and surrounding objects, it is still difficult to differentiate static reflecting objects and stationary/non-stationary users. To overcome this challenge, one can devise a novel motion detector by leveraging the sensitivity of CIR phase to the change of travelling distance of EM waves, which can identify the large random body motion (RBM) as well as periodic breathing motion from human subjects and measurement noises from static reflecting objects (e.g., wall, door and furniture).

Third, human chest motions are induced by both respiration and heartbeat, and the distance change caused by heartbeat is magnitude weaker than the respiration signal. Although heart rate is usually higher than respiration rate, it is hard to distinguish the true heart rate from harmonics of the breathing signal. To address this challenge, one can first estimate the waveform of the breathing signal and then eliminate it in time domain. To further tackle the problem that the heartbeat signal can easily submerge in random measurement noises, one can leverage the stationary property of the heart rate and apply dynamic programming (DP) algorithm in spectrogram to obtain an accurate estimation of the heart rate.

We have built a prototype of ViMo by reusing commercial off-the-shelf (COTS) 60 GHz WiFi radio as a radar-like device and conducted extensive experiments to evaluate the performance under different settings, including single-person and multi-person scenarios, LOS and NLOS conditions, etc. Experimental results show that ViMo achieves accurate estimations, with a median error of 0.19 BPM and 0.92 BPM, respectively, for RR and HR estimation. In addition, ViMo detects multiple users precisely, with a detection rate of 97.86%. The ViMo system takes an important step towards practical multi-person vital sign monitoring via 802.1 lad radios.

ViMo is a wireless system that can accurately detect human subjects and estimate their vital signs by using purely the reflections of RF signals off the users' bodies. The processing flow of ViMo is shown in FIG. 1, according to one embodiment of the present teaching.

Enabling multi-person contactless vital sign monitoring using 60 GHz WiFi faces several challenges. First, due to the fast attenuation of 60 GHz RF signal, the strength of signal reflected at a large distance is much smaller than that at a short distance. Therefore, it is hard to detect human subjects without prior calibration, let alone detecting the stationary/non-stationary status of human subjects. Second, the minute heartbeat signals are easily corrupted by measurement noises and concealed by the large scale respiration signals. Thus, dedicated systems should be designed to resist the interference from respiration and measurement noises when estimating the heart rate.

In order to detect human subjects at various distances, one can apply a reflecting object detector that adaptively estimates the noise level at various distances and thus detects the presence of reflecting objects. To further differentiate the human subjects from static objects, one can design a motion detector that identifies static objects, stationary human subjects and human with large body motion. A target clustering module is implemented to further identify the number of human subjects and their respective locations. Moreover, to make a robust estimate of the heart rate, one can first devise a breathing signal eliminator to reduce the interference from the respiration signal after the breathing rate is estimated. The eliminator can remove the harmonics of the breathing signal, as well as deal with the spread of the breathing frequency component when the breathing period slightly changes. To tackle with the random measurement noise, one can leverage the stationary property of the heart rate and apply dynamic programming to estimate the heart rate utilizing both the frequency and time diversity.

CIR Modeling with Vital Sign Impact

Figure 2B:
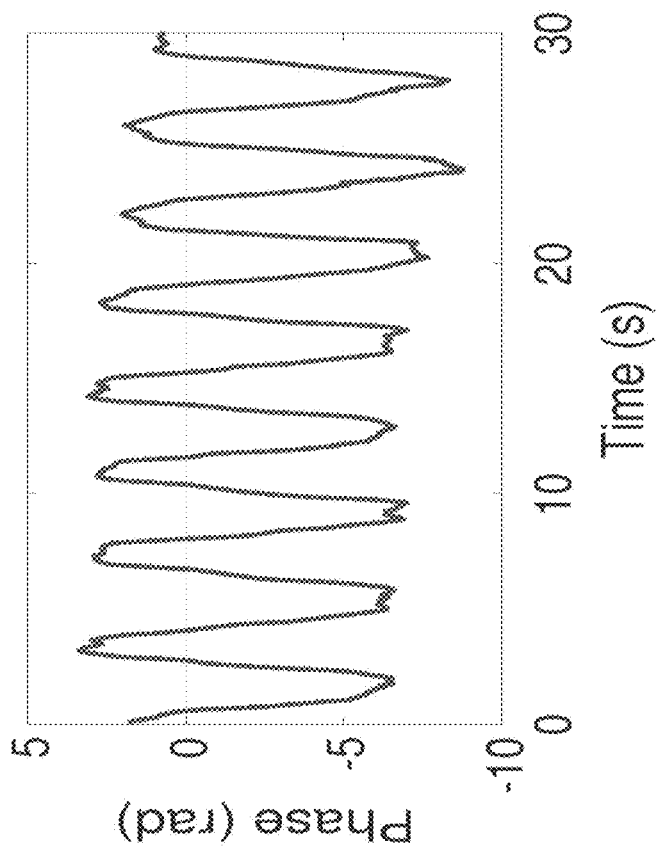
FIG. 2B illustrates a typical phase signal for the tap containing vital signs, according to some embodiments of the present disclosure.
Figure 2A:
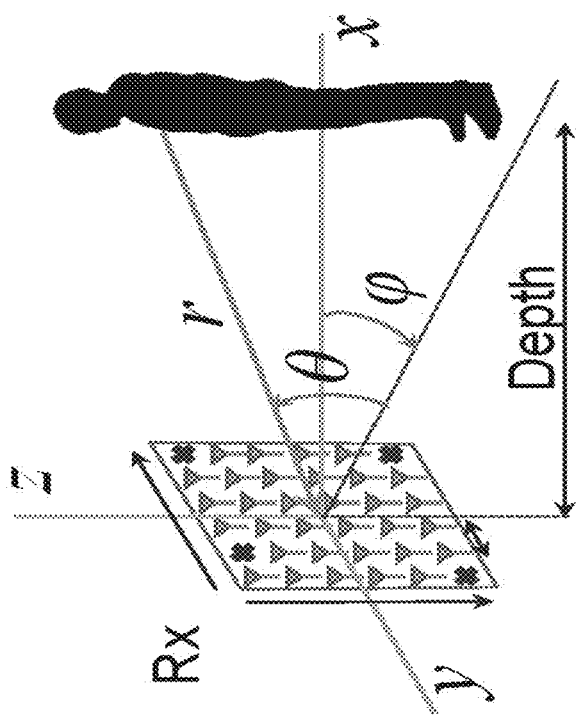
FIG. 2A illustrates the coordinate of the disclosed system, according to some embodiments of the present disclosure.

Assume the travelling distance of the EM wave reflected by human chest is d(t), then the CIR between Tx antenna m and Rx antenna n can be expressed as $$h_{m,n}(t) = a_{m,n}(t)\exp\left(-j2\pi\frac{d_{m,n}(t)}{\lambda_c}\right), \quad (1)$$

where $a_{m,n}(t)$ is the complex channel gain, $\lambda_c$ denotes the wavelength of the carrier. Due to the modulation of the vital signs, i.e., respiration and heartbeat, $d_{m,n}(t)$ appears to be a combination of two periodic signals, which can be further expressed as $$d_{m,n}(t) = d_0(m,n) + s_r(t) + s_h(t), \quad (2)$$

where $s_r(t)$ and $s_h(t)$ denotes the distance change due to respiration and heartbeat. Besides, denote $d_0(m, n) = lT_s c +$ Δd(m, n), where $T_s=1/B$ denotes the fast time resolution and B stands for the system bandwidth. Here one can assume the reflected signal falls into the l-th tap of the measured CIR with residual Δd(m, n), then the l-th tap of the CIR, $h_l(t)=[h_{1,1}(t), h_{1,2}(t), \ldots, h_{M,N}(t)]^T$ can be expressed as $$h_l(t) = a(t)e\exp\left(-j2\pi\frac{d_0+s_r(t)+s_h(t)}{\lambda_c}\right) = \tilde{a}\exp\left(-j2\pi\frac{s_r(t)+s_h(t)}{\lambda_c}\right), \quad (3)$$

where $d_0=[d_0(1,1), d_0(1,2), \ldots, d_0(M, N)]^T$, $a(t)=[a_{1,1}(t), a_{1,2}(t), \ldots, a_{M,N}(t)]^T$, and e denotes elementwise product. One can assume a(t) is time-invariant due to the tiny movement of the subject, and the common phase shift is absorbed in the term ã. The CIR after performing beamforming can be expressed as $$h_{\theta,\phi,l}(t)=s^H(\theta,\phi)h_l(t)+\varepsilon(t), \quad (4)$$

where $s(\theta, \phi)$ is the steering vector pointing to the direction $(\theta, \phi)$ as shown in FIG. 2A and $\varepsilon(t)$ stands for additive white Gaussian noise which are independent and identically distributed (I.I.D) for different links. It is apparent that the phase of the CIR measurement changes periodically in slow time due to the periodic motions of respiration and heartbeat, as shown in Eqn. (3). FIG. 2B shows a typical phase signal containing vital signs collected by the disclosed system.

Target Detection

Since various indoor objects (e.g., wall, desk, etc.) reflect the EM wave, before starting monitoring vital signs, one may first need to detect human subjects in the vicinity of the Tx and the Rx. The human subjects may have body motion and thus will change his/her location in the long run, ViMo divides the duration of measurements into multiple blocks, where each block includes CIR measurements of W seconds. Two adjacent blocks overlap by $W-W_s$ seconds, where $W_s$ is the sliding window length.

Detecting Reflecting Objects

Since the RF signal at 60 GHz attenuates severely with distance, the reflected energy from a same object varies with distance. To locate the human subject, one may first need to identify which spatial cell has reflecting objects.

The CIR measurement for the case when there is no reflecting object and the case when there is a static reflecting object at cell $(\theta, \phi, l)$ can be expressed as $$h_{\theta,\phi,l}^{empty}(t) = \varepsilon(t), \quad (5)$$

and $$h_{\theta,\phi,l}^{static}(t) = s^H(\theta, \phi)\left[a e \exp\left(-j2\pi\frac{d_0}{\lambda_c}\right)\right] + \varepsilon(t), \quad (6)$$

respectively. It is obvious that the power response when there is a reflecting object is much larger than the empty tap. However, it is impossible to find a universal predefined threshold for target detection. According to the propagation laws of EM wave, for the same reflecting object, a shorter distance corresponds to a larger reflecting energy. Furthermore, due to the automatic gain control (AGC) module, the amplitude of the CIRs will change for different measurements.

In order to find the adaptive power threshold for each block, ViMo utilizes a constant false alarm rate (CFAR) algorithm for target detection. The power of the noise level for the cell under test (CUT) is estimated by averaging the power of neighboring cells. Furthermore, the guard cell is used to avoid corrupting estimates with power from the CUT itself.

Figure 3A:
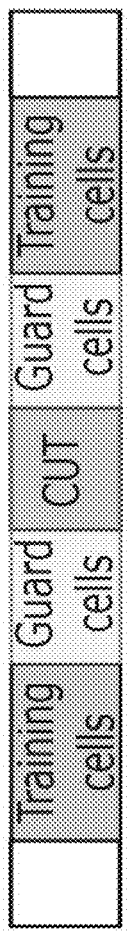
FIG. 3A illustrates a one-dimension (1D) constant false alarm rate (CFAR) window used in range dimension for reflecting subject detection, according to some embodiments of the present disclosure.
Figure 3B:
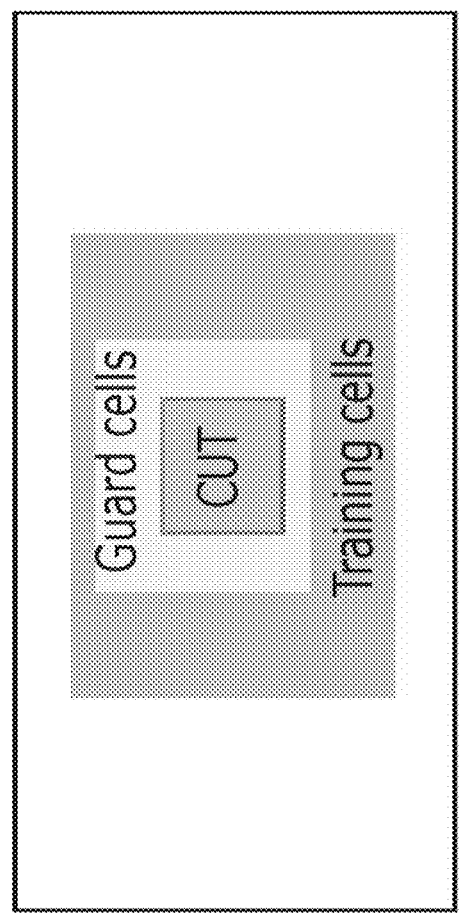
FIG. 3B illustrates a two-dimension (2D) constant false alarm rate (CFAR) window used in angle dimension for reflecting subject detection, according to some embodiments of the present disclosure.
Figure 4:
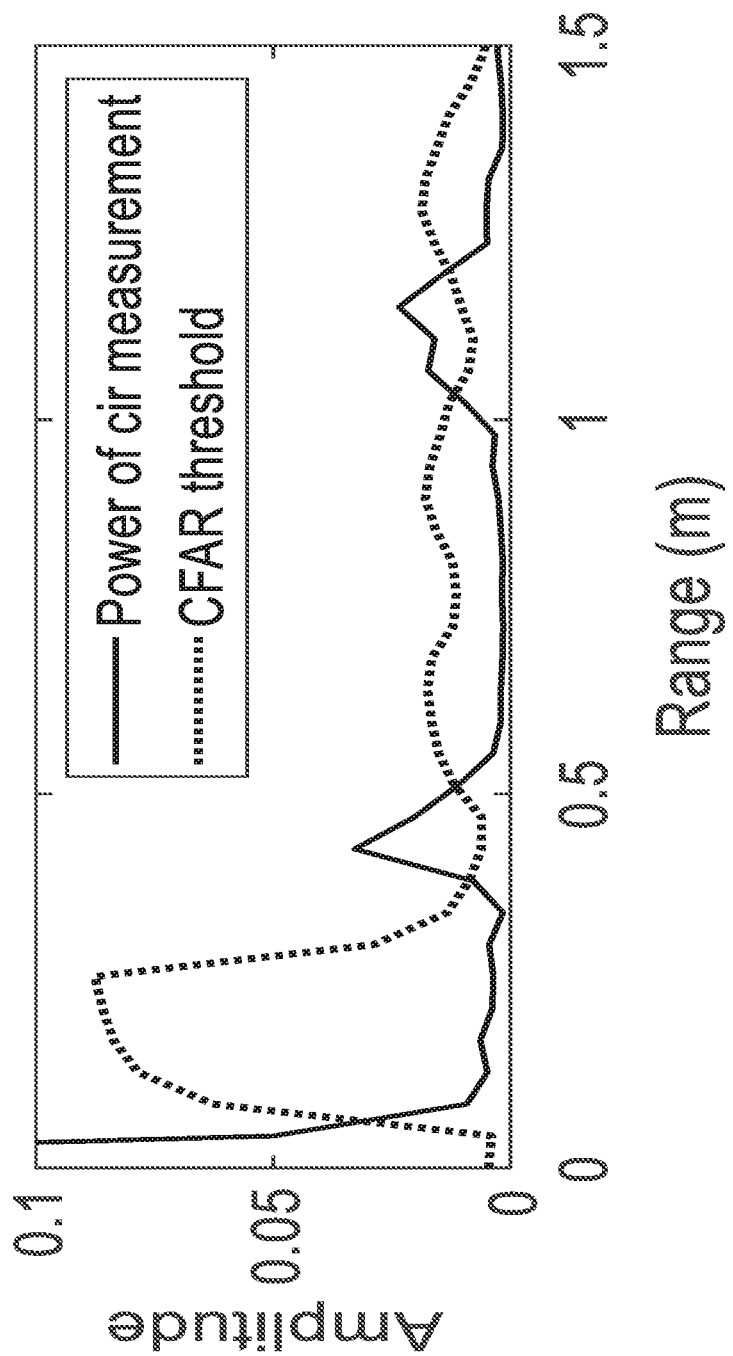
FIG. 4 illustrates an example of 1D-CFAR for reflecting object detection, according to some embodiments of the present disclosure.

In specific, for each block, the input of CFAR detector is the time-averaging amplitude of all the CIR measurements, i.e.

$$h(\theta, \phi, l) = \frac{1}{WF_s}\sum_t |h_{\theta,\phi,l}(t)|,$$

where $F_s$ is the sampling rate. Considering the attenuation property of EM wave, where the reflected signal strength at different distance of the same object will be different, to determine the range of the reflecting objects, 1D-CFAR is adopted, as shown in FIG. 3A. For each sector $(\theta, \phi)$, ViMo convolves CIR measurements $h_{\theta,\phi}(l)$ with the CFAR window to get the estimation of noise level $\hat{n}_{\theta,\phi}(l)$. A scaling factor α is applied to scale the estimated noise level. The detection threshold is thus set to be $\alpha\hat{n}_{\theta,\phi}(l)$, and the taps with reflecting objects should be those whose amplitude are above the detection threshold, as shown in FIG. 4. To determine the noise level at direction $(\theta, \phi)$, one can further employ 2D-CFAR for tap l, where the noise level $\hat{n}_l(\theta, \phi)$ is estimated by convolving CIR measurements $h_l(\theta, \phi)$ with the 2D-CFAR window as shown in FIG. 3B. Scaling factor β is applied to scale the estimated noise level. The reflecting object should be in the cell $(l, \theta, \phi)$ whose CIR measurement $h(\theta, \phi, l)$ is above detection threshold $\alpha\hat{n}_{\theta,\phi}(l)$ and $\beta\hat{n}_l(\theta, \phi)$ simultaneously. Here, one can define the indicator of reflecting object $1_R(l, \theta, \phi)$ as $$1_R(l,\theta,\phi)=1\{h(\theta,\phi,l)>\max(\alpha\hat{n}_{\theta,\phi}(l),\beta\hat{n}_l(\theta,\phi))\}, \quad (7)$$

where $1\{\cdot\}$ is the indicator function.

Although CFAR detector can identify which cell is occupied by reflecting objects, it cannot differentiate whether the reflection comes from human or not. Human subjects always accompany motion (either from breathing or RBM), which is a specific characteristic different from static objects, one can design a motion detector to identify human subjects. Furthermore, most of the wireless vital sign monitoring systems assume there is only one human subject and no RBM during the measurement, and thus the procedure of finding the human subjects is omitted, which is neither natural nor realistic for practical deployment. So in this part, one can design a motion detector, which enables ViMo to identify static reflecting objects, stationary human subjects and human with RBM.

Static Reflecting Objects Detection

Even stationary human subjects can introduce motion due to respiration and heartbeat, and the distance change caused by respiration can be discerned by phase change according to Eqn. (3), one can calculate the variation of the phase of the CIR measurement $V_r(\theta, \phi, l)$ for each candidate cell $(\theta, \phi, l)$ selected by reflecting objects detector, which is defined as $$V_r(l,\theta,\phi)=\text{Var}_t[\phi h_{\theta,\phi,l}(t)], \quad (8)$$

where $\text{Var}_t[\cdot]$ denotes the variance over parameter t and ∠ denotes the phase of a complex value. As shown in Eqn. (6), for a static reflecting objects, $V_r(\theta, \phi, l)$ would be small, but for the cell with human subjects, either respiration or RBM will contribute a large $V_r(\theta, \phi, l)$. ViMo utilizes a predefined threshold $\eta_{min}$ to identify a static reflecting objects if $V_r(\theta, \phi, l) < \eta_{min}$. The phase signal and its variance are shown in FIG. 5A and FIG. 5D respectively.

FIGS. 5A-5F illustrate exemplary phases for target detection, where the reference RR of the stationary human subject is 16 BPM according to some embodiments of the present disclosure. FIGS. 5A-5C show the phase signals corresponding to static object, stationary subject, and human in motion, respectively; FIG. 5D shows the phase variance of signals in FIGS. 5A-5C; FIGS. 5E-5F show the ACF of FIG. 5B and FIG. 5C respectively.

Stationary Human Subjects Detection

For a stationary human subject, periodic breathing signal can be observed in the phase measurement according to Eqn. (1), and FIG. 5B gives an example of phase with stationary subject. A bin with stationary subject would have $V_t(\theta, \phi, l) > \eta_{min}$ and a periodic phase signal whose frequency within $[b_{min}, b_{max}]$.

The frequency resolution is $$\Delta f = \frac{60}{W}$$

breath per minute (BPM), where W is the window length in seconds. Therefore, to get an acceptable estimation accuracy of respiration rate, the window length should be long enough, which will cause a large delay. In the disclosed system, one can adopt a statistical approach by examining the auto-correlation function (ACF) of the candidate CIR phase to evaluate the periodicity.

Here one can denote the time-variant part of CIR phase measurement as $$y(t) = s_r(t) + s_h(t) + n(t), \quad (9)$$

where n(t) is the random phase offset introduced by noise, and is also a random variable independent in time instances. Thus the ACF of y(t) can be calculated as $$\rho(\tau) = \frac{\text{Cov}[y(t), y(t+\tau)]}{\text{Cov}[y(t), y(t)]}, \quad (10)$$

where $\tau$ denotes the time lag, and $\text{Cov}[\cdot]$ denotes the con-variance operator. Assume that the distance change caused by heartbeat $s_h(t)$ is uncorrelated with the distance change caused by respiration $s_r(t)$, then $\rho(\tau)$ can be expressed as $$\rho(\tau) = \frac{\text{Var}[s_r(t)]}{\text{Var}[y(t)]}\rho_r(\tau) + \frac{\text{Var}[s_h(t)]}{\text{Var}[y(t)]}\rho_h(\tau) + \frac{\text{Var}[n(t)]}{\text{Var}[y(t)]}\rho_n(\tau), \quad (11)$$

where $\text{Var}[y(t)] = \text{Var}[s_r(t)] + \text{Var}[s_h(t)] + \text{Var}[n(t)]$. $\rho_r(\tau)$, $\rho_h(\tau)$ and $\rho_n(\tau)$ denote the ACF of respiration, heartbeat and noise respectively. Since one can have $\text{Var}[s_r(t)] \gg \text{Var}[s_h(t)]$ and $\text{Var}[s_r(t)] \gg \text{Var}[n(t)]$, then one can have the approximation that $\rho(\tau) \approx \rho_r(\tau)$. The ACF will have a definite peak at a certain delay which corresponds to the breathing cycle as shown in FIG. 5E.

Motion Detection

Random body motion (RBM) has been one of the most difficult technical challenges to wireless vital sign monitoring. Compared with the millimeter-scale chest movement caused by heartbeats, the scale of RBM can be tens of centimeters. The time-variant part of CIR phase measurement with RBM can be modeled as $$y(t) = s_m(t) + s_r(t) + s_h(t) + n(t), \quad (12)$$

where $s_m(t)$ is the distance change caused by motion. FIG. 5C shows an example of phase with motion. When the scale of RBM is much larger than the respiration signal, the variation $\text{Var}[s_m(t)] \gg \text{Var}[s_r(t)] \gg \text{Var}[s_h(t)]$, and thus $V_t(l, \theta, \phi) > \eta_{max}$, where $\eta_{max}$ is a predefined threshold. When the subjects have moderate RBM, the variance of phase may be within the threshold, however, since RBM lacks periodicity in most case, one cannot observe a peak in $\rho(\tau)$ as the stationary case as shown in FIG. 5F. Therefore, one can have the motion indicator $1_M(\cdot)$ defined as $$1_M(\theta, \phi, l) = 1(V_t(\theta, \phi, l) > \eta_{max} \cup \rho(\tau_b) < \Gamma), \quad (13)$$

where $1(\cdot)$ is the indicator function, $\tau_b$ is the first peak of ACF $\rho(\tau)$, and $\Gamma$ is a predefined threshold.

Cell Merging/Clustering

Due to the fact that multiple cells have the RF signals reflected off a single human subject, a target clustering method should be employed before determining target number and vital sign monitoring. Considering the size of human body, one can merge them into a cluster if the spatial distance between these cells is within the threshold $d_{min}$. The cluster center of stationary cells is the cell with the largest ACF peak, corresponding to the cell with human chest. The center of the RBM cells for each cluster is the cell with the largest $V_t(\theta, \phi, l)$, corresponding to the cell with the largest body motion. Even for a stationary person, he/she can have body motion from the body part away from chest. So when the distance between stationary cells and RBM cells is smaller than the threshold $d_{min}$, then these cells belong to the same person, and the center of cluster should be the representative of stationary cells.

Figure 6:
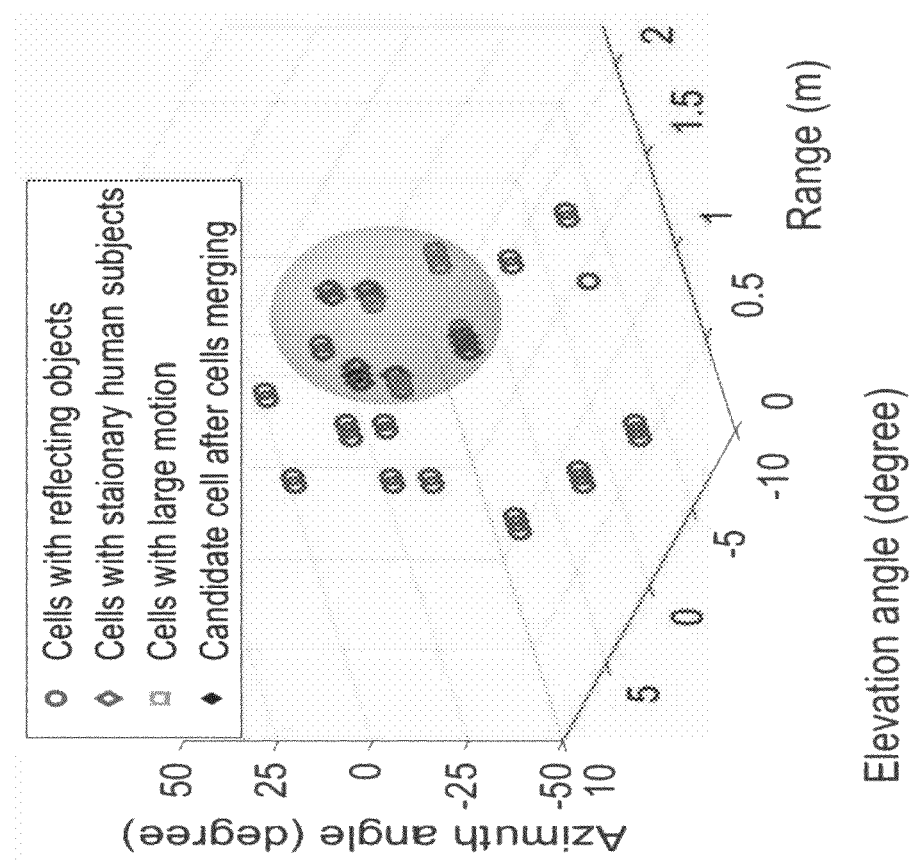
FIG. 6 illustrates an example of cell merging, according to some embodiments of the present disclosure.

FIG. 6 shows an example for cells merging, where the ground truth is that a human subject sits at 1 m away from the device in a typical indoor office. The reflecting objects detected by CFAR detector is shown in blue circles. The motion detector further differentiates cells with stationary subjects and RBM, shown as red diamonds and green squares respectively. The representative of the target is shown in solid black diamond.

Heart Rate Estimation

The ViMo enables the heart rate estimation module once a stationary subject has been detected. Since one can check periodicity using ACF to determine whether the cell contains a stationary respiration signal, one can easily determine the breathing cycle by finding the peak location $\tau_r$ of $\rho(\tau)$, and the breathing rate should be $$f_r = \frac{60}{\tau_r}, \quad (14)$$

breath per minute (BPM).

Figures 7A, 7B, 7C:
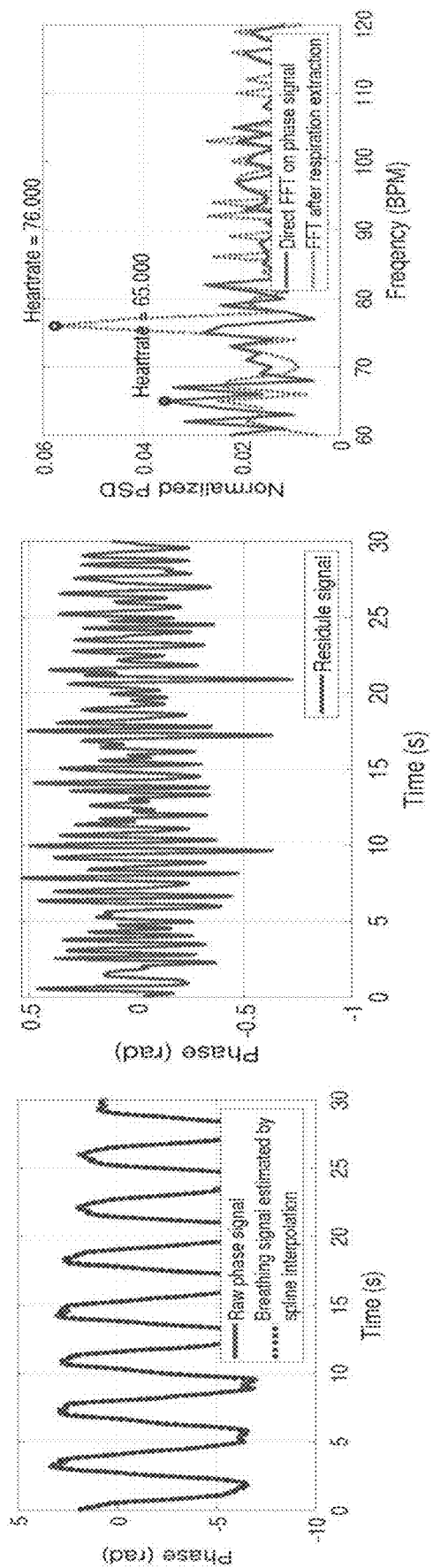
FIGS. 7A-7C illustrate exemplary effects of breathing interference elimination, according to some embodiments of the present disclosure.

FIGS. 7A-7C illustrate exemplary effects of breathing interference elimination, where the ground truth of heart rate is 76 BPM, according to some embodiments of the present disclosure. FIG. 7A shows the smoothing spline estimate of breathing signal; FIG. 7B shows the residual after breathing signal elimination; and FIG. 7C shows the power spectrum density (PSD) of original phase and residual signal.

Heartbeats can introduce minute movements of the chest, which can be detected as small peaks in the unwrapped phase as shown in FIG. 7A. Past works try to directly utilize frequency analysis and bandpass filter (BPF) to estimate the heart rate. However, due to the harmonics introduced by respiration, it is easy to pick up the wrong peak for estimation as shown in blue line in FIG. 7C. Thus, in order to get a higher estimation accuracy, one can first eliminate breathing signal before heart rate estimation. Thus, in order to get a higher estimation accuracy, one can first eliminate breathing signal before heart rate estimation.

Breathing Interference Elimination

Eliminating the breathing signal can improve signal-to-interference-plus-noise ratio (SINR) of the heartbeat signal, and thus improve the estimation accuracy. The polynomial fitting has been used to remove respiration motion. However, one of the main drawbacks of the polynomial fitting is the order selection. If the order is selected by empirical experience, under-fitting or over-fitting can be easily triggered when the experimental setting is changed (e.g., change of sampling rate or window length). Besides, the elimination effect is also related with the breathing rate. In other words, in order to achieve the similar elimination effect, the polynomial order should adapt to user's breathing rate, which is not practical for robust daily deployment. To avoid this effect, ViMo adopts smoothing spline to estimate the breathing signal.

Let $\{t_i, y(t_i): i=t_0, t_0+T_s, \ldots, t_0+W\}$ to be a set of observation in the current window, where $$T_s = \frac{1}{F_s}$$

is the time interval between two adjacent samples, $t_0$ is the initial time of the observation window, and W is the window length. Compared to the heartbeat signal, the respiration signals have larger distance change and lower frequency, thus, the estimate of the breathing signal $s_r(t)$ should be the solution of $$\min_{\hat{f}} \sum_{i=t_0}^{t_0+W} \{y(t_i) - \hat{f}(t_i)\}^2 + \lambda \int \hat{f}''(t)^2 dt, \qquad (15)$$

where $\lambda \geq 0$ is a smoothing parameter. The second term evaluates the smoothness of a function. The smoothing parameter controls the trade-off between fidelity to the data and smoothness of the function estimate. $\hat{f}$ is the estimate of $s_r(t)$, defined as $$\hat{f}(t) = \sum_{i=t_0}^{t_0+W} \hat{f}(t_i) f_i(t), \qquad (16)$$

where $f_i(t)$ are a set of spline basis function. In this work, one can use B-spline as the spline basis.

To get the optimum solution of Eqn. (15), one can first define the vector $\hat{m} = [\hat{f}(t_0), \ldots, \hat{f}(t_0+W)]^T$, and the roughness penalty has the form $$\int \hat{f}''(t)^2 dt = \hat{m}^T A \hat{m}, \qquad (17)$$

where the elements of A are $\int f_i''(t) f_j''(t) dt$. Therefore, the penalized sum-of-squares can be written as $$\min_{\hat{m}} \{y - \hat{m}\}^T \{y - \hat{m}\} + \lambda \hat{m}^T A \hat{m}, \qquad (18)$$

where $y=(y(t_0), \ldots y(t_0+W))^T$. The minimizer of Eqn. (18) is thus $$\hat{m}^* = (I + \lambda A)^{-1} y. \qquad (19)$$

The heartbeat after elimination of the breathing signal is thus $$\hat{s}_h(t) = y(t) - \hat{m}^{*T} f(t), \qquad (20)$$

where f(t) is the vector form of spline basis functions.

The dashed line in FIG. 7A shows the estimation of the breathing signal. After breathing signal elimination, the spectrum of the residual signal after applying a band-pass filter (BPF) with passing band $[h_{min}, h_{max}]$ is shown in yellow dashed line in FIG. 7C. The spectrum of the phase without eliminating respiration signal using the same BPF is shown in blue solid line. It is obvious that the signal-to-interference-plus-noise ratio (SINR) of the heartbeat signal after breathing elimination is boosted. Specifically, the SINR is boosted from 1.65 dB to 5.65 dB by eliminating the respiration signal.

Heart Rate Estimation using Spectrogram

Breathing signal elimination can enhance the SINR of heartbeat signal, and thus, increase the accuracy of heart rate estimation. However, the random measurement noises can still corrupt the estimation at some time instances. To further increase the estimation accuracy, in ViMo, one can leverage the stationary property of heart rate and utilize the diversity in both frequency and time domains for reliable estimation.

Figure 8:
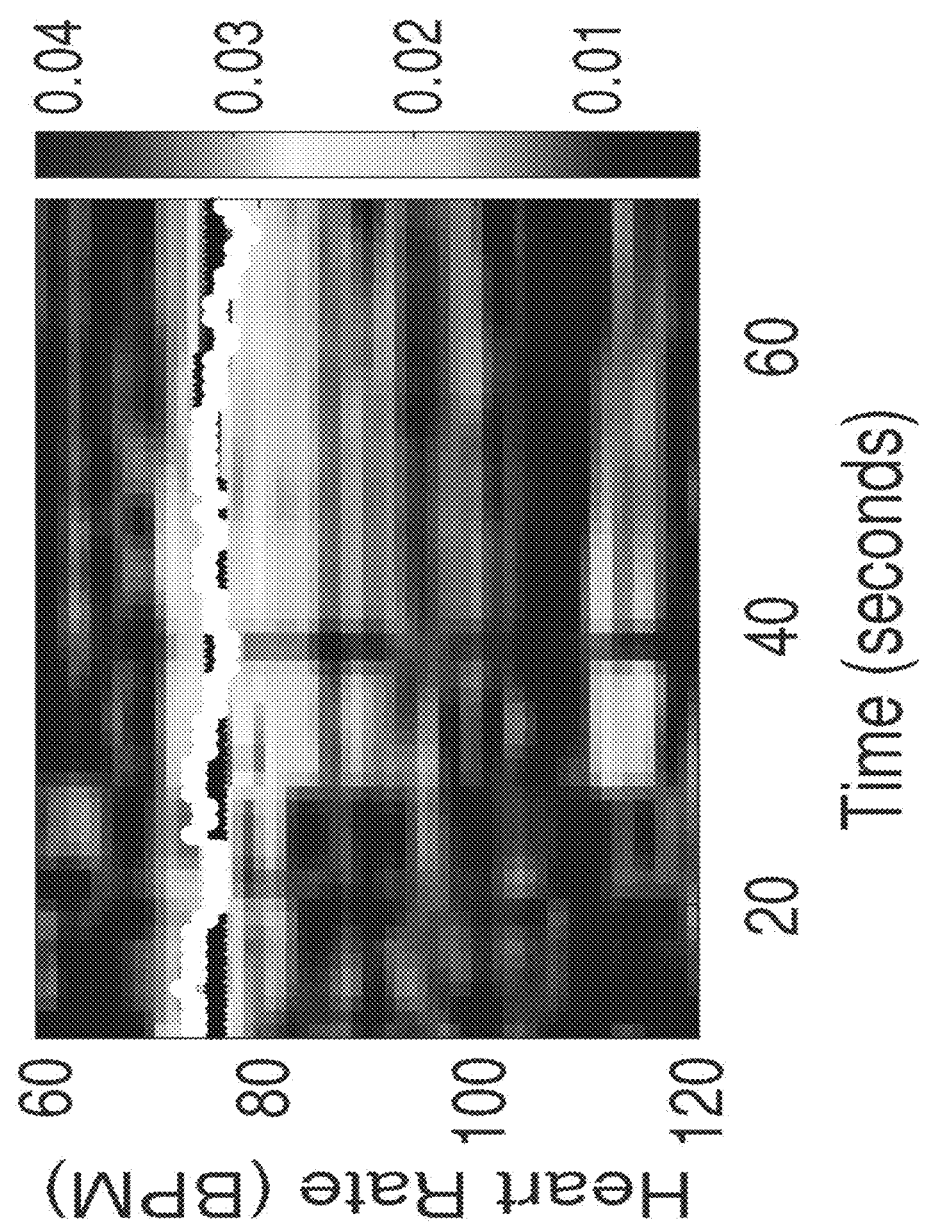
FIG. 8 illustrates estimated results by dynamic programming, according to some embodiments of the present disclosure.

The heart rate can smoothly change over time, one can model the heart rate as a Markov process, where the variation of heart rate between two adjacent time bins follows a normal distribution $\mathcal{N}(0, \sigma^2)$, and the probability density function (PDF) is denoted as p(f). After breathing signal elimination, one can perform Fast Fourier Transform (FFT) on the residual and concatenate the PSD of each window to get a spectrogram as shown in FIG. 8, where the white line shows the ground truth measured by an ECG sensor, and the black is the estimation result.

Since the operation of FFT automatically discretizes the continuous frequency in the range of $[h_{min}, h_{max}]$ into $|Q|$ frequency components, where $|Q|$ means the cardinality of set $Q$, the heart rate can be modeled as a Markov chain, and the transition probability matrix is denoted as $P \in \mathbb{R}^{|Q| \times |Q|}$, which is defined as $$P(q, q') = P(g(n) = q' | g(n-1) = q) \qquad (21)$$
$$= \int_{(q'-q-\frac{1}{2}) * \Delta f}^{(q'-q+\frac{1}{2}) * \Delta f} p(f) df,$$

where $\forall q, q' \in Q$. Here, $g: [1, N] \to Q$ is a mapping indicating the frequency component at the $Q$ given time, and N is the total time instances of a given spectrogram.

In principle, the heart beat signal is more periodic than noise and other motion interference. Thus, it is more likely to be observed as peaks in most of the time. Moreover, considering that one's heart rate will not fluctuate a lot within a short period, estimations of heart rates should form a trace that achieves a good balance between frequency power and temporal smoothness.

The most probable heart rate trace can be found by solving $$g^* = \underset{g}{\operatorname{argmax}} E(g) - \kappa C(g), \quad (22)$$

where $\kappa$ is a regularization factor. g is denoted as a trace, where $$g = (n, g(n))_{n=1}^N. \quad (23)$$

E(g) is the power of trace g, defined as $$E(g) = \Sigma_{n=1}^N \varepsilon(n, g(n)), \quad (24)$$

where $\varepsilon(n, q)$ denotes the energy at time bin n and frequency component q. The smoothness of the trace can be evaluated by a cost function C(g), defined as $$C(g) \triangleq -\log P(g(1)) - \Sigma_{n=2}^N \log P(g(n-1), g(n)), \quad (25)$$

where the frequency transition probability $P(g(n-1), g(n))$ can be calculated by Eqn. (21). Without loss of generality, one can assume a uniform prior distribution, i.e., $$P(g(1)) = \frac{1}{|Q|}.$$

This problem can be solved by dynamic programming. For clarity, one can first define the score at bin (n, q) as the maximum achievable regularized energy, i.e., $$S(n, q) = \varepsilon(n, q) + \max_{\forall q' \in Q} \{S(n-1, q') + \lambda \log P(q', q)\}, \quad (26)$$
$$n = 2, 3, \ldots, N, \forall q, q' \in Q,$$

where $S(1, q) = \varepsilon(1, q) + \lambda \log P(g(1) = q)$. Furthermore, since S(n, q) consider both the smoothness and regularized energy of the previous trace, the process of calculating the score also determines the optimal trace passing through bin (n, q). The entire optimal heart rate trace can be found by backtracking the bins (N, g*(N)) that contribute to the maximum score of the last timestamp. For the rest of the heart rate trace in the observation window, i.e., $\forall n = N-1, N-2, \ldots, 1$, one can have $$g^*(n) = \underset{\forall q \in Q}{\operatorname{argmax}} S(i, q) + \lambda \log P(q, g^*(n+1)). \quad (27)$$

The backtracking procedure in Eqn. (27) gives the optimal trace g* for a given spectrum, which is the optimal solution for Eqn. (22). The result of heart rate trace estimation is shown as black line in FIG. 8, where the reference measured by a gold standard electrocardiogram (ECG) sensor is marked as the white line.

Experiment Evaluation

One can evaluate ViMo in practical settings using a commodity 802.11ad chipset in a typical office. The chipset operates at 60 GHz center frequency with 3.52 GHz bandwidth, providing a range resolution of 4.26 cm. The Tx transmits a known pulse sequence for channel impulse response (CIR) estimation. There are 8 participants enrolled for testing. The ground truth is provided by a commercial ECG sensor with a chest strap.

To further evaluate the disclosed system, one can compare it with the mmVital, which is the state-of-art wireless vital sign monitoring system using impulse-based mmWave radio. mmVital leverages the RSS from a pair of horn antenna and finds the highest magnitude peak as well as its adjacent bins in the frequency domain to form a custom narrow BPF, and then counts peaks of the time-domain filtered signal to determine the breathing rates as well as heart rate. In order to make fair comparison, same as ViMo, phases of CIRs from the detected cells are used as the input of mmVital algorithm, rather than the coarse information of RSS. To estimate both respiration and heart rate, the adaptive narrow BPF and IFFT are implemented as illustrated in mmVital. The window length for both mmVital and ViMo are set to be 60 seconds, and systems give output every second. The mmVital estimates vital signs according to the number of peaks in a time window (i.e., the estimation is integer), the resolution of its breathing rate as well as heart rate estimation is 1 beat/breath per minute (BPM).

Overall performance in the measurement of respiration rate (RR) and heart rate (HR): The detection rate of the system is 97.86% and the overall median error of RR and HR evaluated by ViMo is 0.19 BPM and 0.92 BPM respectively. mmVital achieves similar performance w.r.t. RR, but its median error of HR is 1.6 BPM, 73.91% worse than ViMo. Experimental results show that ViMo can provide more accurate estimation especially in the relative low SNR setting (e.g., longer distance, NLOS, etc.) due to the fact that the breathing signal elimination and DP for HR estimation can increase the SINR of heartbeat signal.

Moreover, experimental results show that ViMo can effectively detect stationary/non-stationary state of human subjects, and can make accurate estimates of both RR and HR when slight user motion incurs (e.g., shaking head). Comparing with mmVital, which does not take users' motion into consideration, ViMo makes an important improvement towards practical deployment. The details will be discussed below.

Impact of Distance

Figure 9C:
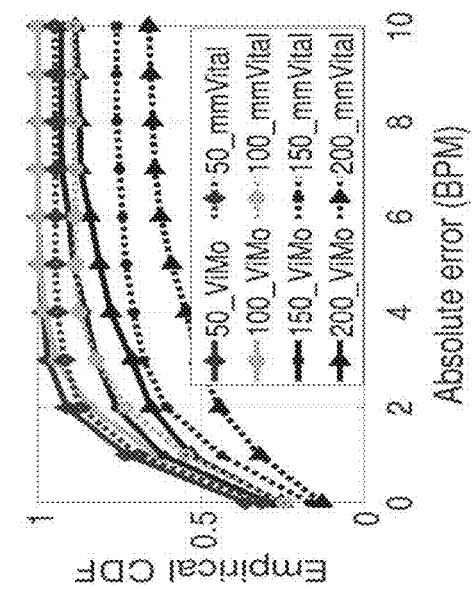
FIGS. 9A-9C illustrate an experiment setup and result for the impact of distance, according to some embodiments of the present disclosure.
Figure 9B:
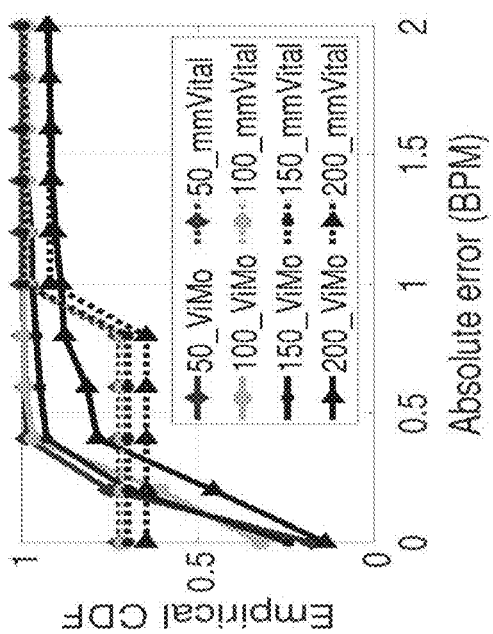
Figure 9A:
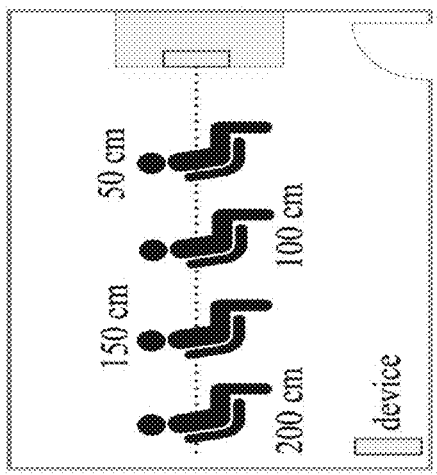

One can investigate the effect of the distance between the device and human subject on the estimation accuracy. FIGS. 9A-9C illustrate an experiment setup and result for the impact of distance, according to some embodiments of the present disclosure. FIG. 9A illustrates the experiment setup; FIG. 9B illustrates the CDF of absolute estimation error for respiration rate; FIG. 9C illustrates the CDF of absolute estimation error for heart rate.

Participants sit at different distances facing the device as shown in FIG. 9A. The empirical cumulative distribution function (CDF) of the absolute error of RR and HR estimation are shown in FIG. 9B and FIG. 9C respectively, where the performance of ViMo and mmVital are shown in solid lines and dash lines respectively. To account for the misdetection, one can set the estimation to be 0 BPM when the target is missed.

As expected, the performance degrades with distance due to the signal-to-noise ratio (SNR) degradation. The median error for RR of ViMo is within 0.15 BPM when the distance is within 1.5 m and it increases to 0.22 BPM when the distance increases to 2 m. For HR estimation, the median error of ViMo increases from 0.42 BPM to 0.9 BPM when the distance increases from 0.5 m to 2 m. Furthermore, one can see that the degradation of RR estimation is less than the HR estimation due to the higher SNR of breathing signal.

The CDF of RR estimation using mmVital algorithm is stepwise since the resolution of both ground truth and estimation is 1 BPM. It is obvious that both algorithms achieve similar performance as for RR estimation, but ViMo achieves a higher resolution. Moreover, for HR estimation, ViMo outperforms mmVital for all the 4 settings, and the performance gap becomes larger with the increment of distance. The main reason is that the breathing signal elimination helps to improve the SINR of heart rate signal. Besides, DP algorithm in ViMo also leverages the time diversity besides the frequency diversity to make estimation, which can further alleviate the impact of the measurement noises.

Impact of Orientation

Figures 10A, 10B, 10C:
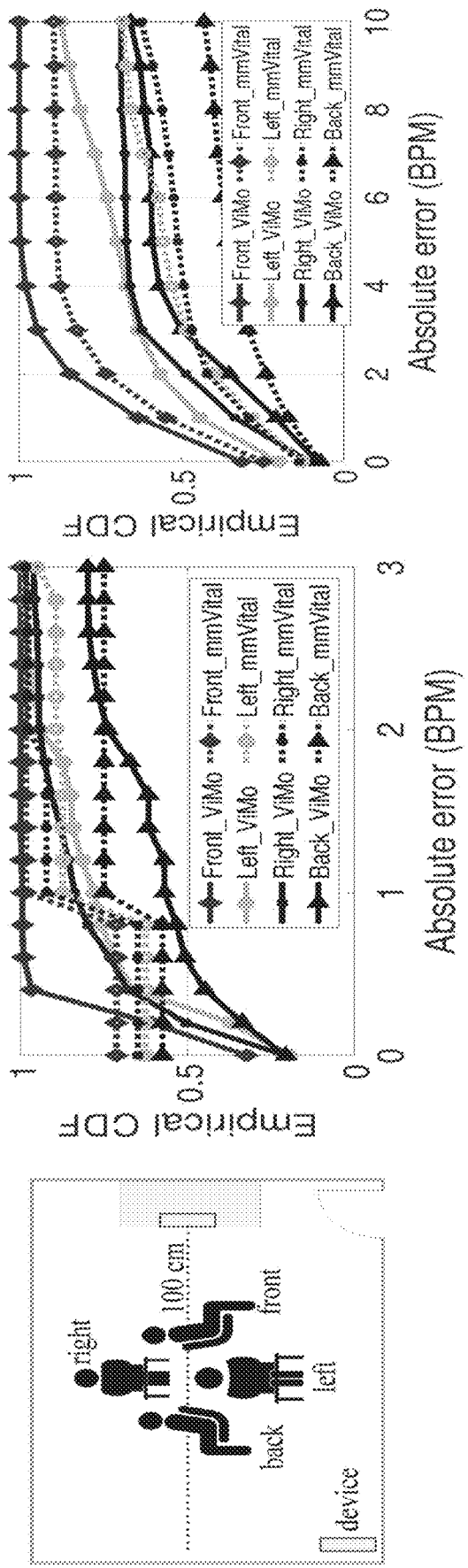
FIGS. 10A-10C illustrate an experiment setup and result for the impact of orientation, according to some embodiments of the present disclosure.

One can also investigate the impact of human orientation on estimation accuracy. FIGS. 10A-10C illustrate an experiment setup and result for the impact of orientation, according to some embodiments of the present disclosure. FIG. 10A illustrates the experiment setup; FIG. 10B illustrates the CDF of absolute estimation error for respiration rate; FIG. 10C illustrates the CDF of absolute estimation error for heart rate.

The orientation corresponds to the closest part of the user w.r.t. the device as shown in FIG. 10A. The distance from the user to device is set to be 1 m. FIG. 10B and FIG. 10C show the estimation performance of RR and HR respectively.

It is shown that the "front" setting achieves the best performance, whereas, the "back" setting has the worst performance, for both RR and HR estimation. This result is due to the distinct displacement of reflecting part caused by respiration in different orientation. Since smaller displacement means lower SNR of breathing signal, when the displacement is too small, mis-detection occurs. The detection rate when subject sit facing the device is 100%, and it degrades to 99.06% and 99.37% when the left and right side of chest facing the device. The detection rate drops to 83.83% when human subjects sit back to the device. It is worth noting that even similar detection rates are achieved when participants sitting at the left and right orientation, the HR estimation performance is distinct, where the "left" setting outperforms the "right" setting. This is due to the physiological structure of human beings, where the vibration caused by the heartbeat is larger on the left side of the chest. Similarly, ViMo has equivalent performance in terms of RR estimation compared with mmVital, however, it has much better performance of HR estimation for all the 4 settings, as shown in FIG. 10C.

Impact of Incident Angle

Figure 11C:
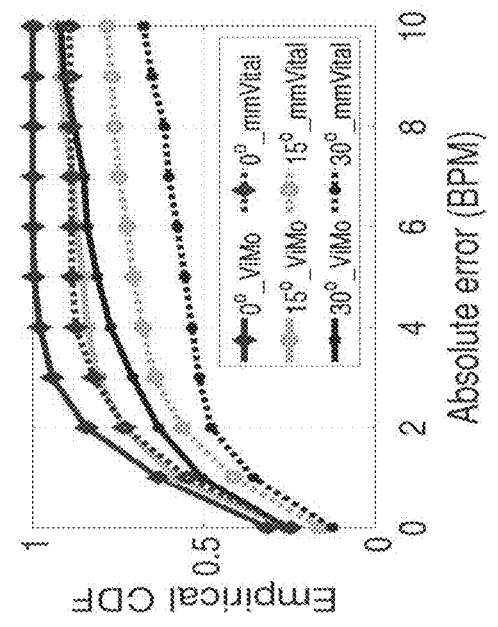
FIGS. 11A-11C illustrate an experiment setup and result for the impact of incident angle, according to some embodiments of the present disclosure.
Figure 11B:
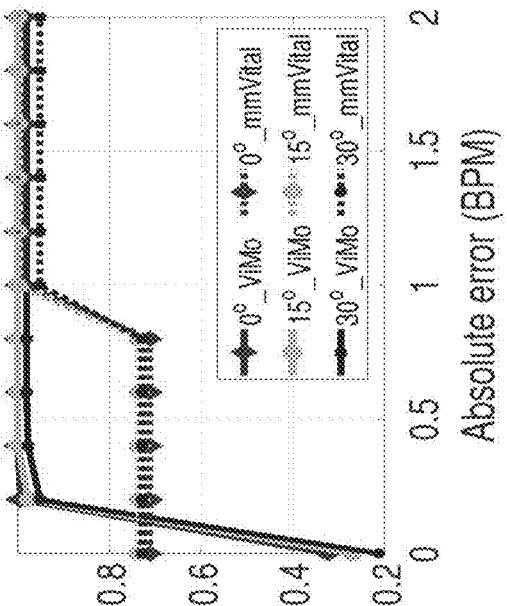
Figure 11A:
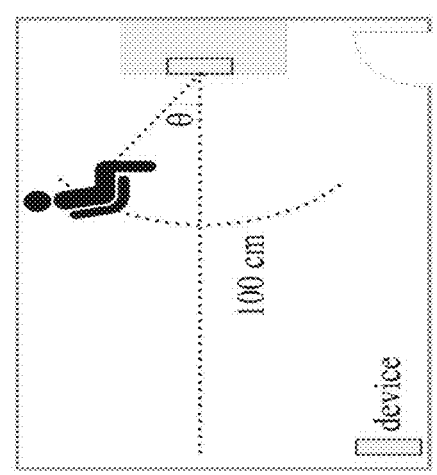

One can also investigate the impact of the incident angle on the estimation performance, where human subjects are asked to sit at angles [00, 15°, 30° ], and the distance between human and device is 1 m, as shown in FIG. 11A. The CDF of absolute estimation error of RR and HR with different incident angles are shown in FIG. 11B and FIG. 11C respectively.

We can see that for both RR and HR estimation, the accuracy decreases with the increment of the incident angle. The reason is that the reflection loss is dependent on the incident angle, and increment in incident angle increases the reflection loss, rendering lower SNR of reflected signal. However, since the SNR of breathing signal is much higher than the heart beat signal, the performance degradation of RR estimation is not as severe as HR estimation. Furthermore, one can see that the performance of ViMo is much better compared with mmVital in terms of HR estimation, especially in the case of large incident angle.

NLOS Case

Figure 12C:
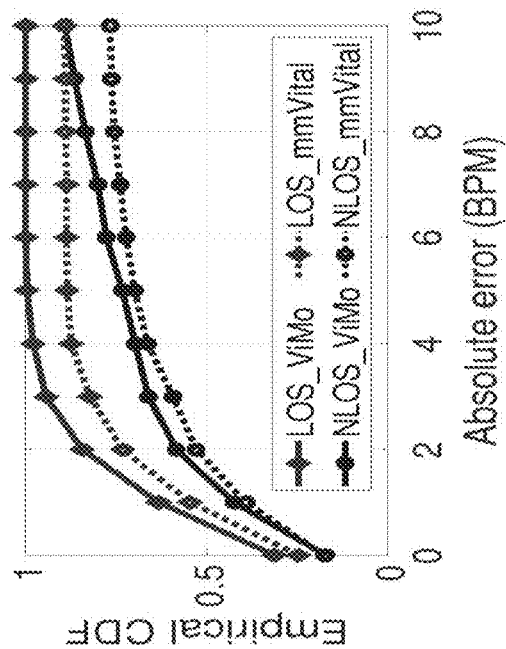
FIGS. 12A-12C illustrate an experiment setup and result for the impact of blockage, according to some embodiments of the present disclosure.
Figure 12B:
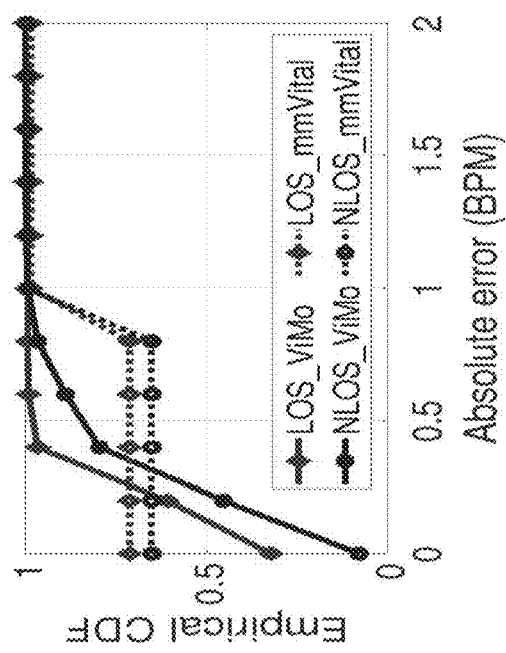
Figure 12A:
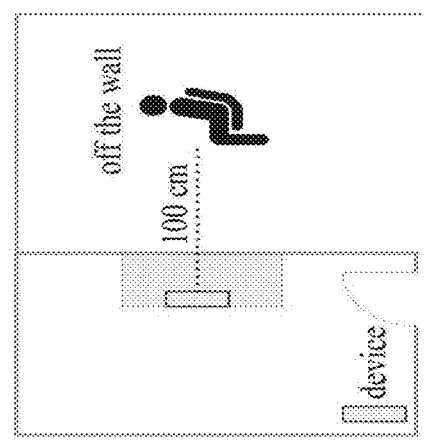

FIGS. 12A-12C illustrate an experiment setup and result for the impact of blockage, according to some embodiments of the present disclosure. FIG. 12A illustrates the experiment setup; FIG. 12B illustrates the CDF of absolute estimation error for respiration rate; FIG. 12C illustrates the CDF of absolute estimation error for heart rate.

The RR and HR estimation accuracy is evaluated for through-the-wall case, and the experiment setup is shown in FIG. 12A. Participants are asked to sit on the other side of a dry wall, and the distance between device and human subject is 1 m. The median error of RR estimation increases from 0.15 BPM to 0.25 BPM due to the penetration loss, and the median error of HR estimation increases from 0.6 BPM to 1.4 BPM, as shown in FIG. 12B and FIG. 12C respectively.

In order to further investigate the influence of blocking material (corresponding to different penetration loss), one can conduct a set of experiments, where different commonly used materials are used to block the LOS path. Since the penetration loss is distinct for different material, the performance drop is different. The mean absolute error (MAE) of RR and HR estimation is shown in Table 1 as follows.

| Blocking material | None (LOS) | Glass | Cotton pad | Wood panel | White board | Drywall |
|---|---|---|---|---|---|---|
| Mean RR error (BPM) | 0.14 | 0.23 | 0.24 | 0.26 | 0.28 | 0.29 |
| Mean HR error (BPM) | 1.29 | 2.66 | 3.45 | 4.82 | 4.85 | 5.95 |

Impact of Body Movement

We evaluate the performance of ViMo when users have different motion states. Participants are asked to shake head (1-3 cm) and move the body (4-5 cm) every 20 seconds. The distance from device to user is 1 m with incident angle 0°. One can also evaluate the performance when users answer phone with headset. The MAE of RR and HR are shown in Tab. 2 as follows.

| Body state | Stationary | Shaking head (left-right) | Moving body (left-right) | Speaking |
|---|---|---|---|---|
| Mean RR error (BPM) | 0.14 | 0.28 | 0.51 | 1.22 |
| Mean HR error (BPM) | 1.29 | 4.16 | 3.06 | 6.31 |

All the cases achieve more than 99.7% detection rate, where for the case of moving body, in 27% of the duration one can detect large body motion, and thus the vital signs estimation module will not be triggered. As for the time that body motion is within the detection threshold (as known as stationary period), the vital sign estimation module is triggered, and the mean HR error is 3.06 BPM for the case of moving body (the relative error is 4%). However, for the case when people are answering phone, the chest will involve RBM caused by speaking more frequently, resulting the worst performance for all the test cases.

Multi-User Case

In this part, one can study the impact of angle separation between users, where two users sit at a distance of 1 m away from the device with different separation angles. One can define the detection index (DI) of a separation angle as the ratio between the number of samples when the number of detected targets matches the ground truth and the total number of samples. One can also define the false-alarm index (FI) of a separation angle as the ratio between the number of samples when the number of detected targets is larger than the ground truth and the total number of samples. Tab. 3 below shows the median error of RR and HR estimation for both users.

| Separation angle | DI | FI | Med. error of breathing | Med. error of heart rate |
|---|---|---|---|---|
| 30° | 0.84 | 0 | (1.14;0.15) | (2;1) |
| 45° | 0.98 | 0 | (0.22;0.14) | (1;1) |
| 60° | 1 | 0 | (0.21;0.14) | (1;1) |
| 75° | 1 | 0 | (0.21;0.12) | (1;1) |

Compared to the single-user scenario, the performance degrades at small separation angles (i.e., 30°), but the performance is similar to the single-user scenario if the separation angels are large enough (i.e., larger than 45°). This is because that when the distance of two targets is small enough, the distance of the candidate cells with each user can be smaller than the predefined threshold. Thus, the two clusters will be merged together and there will be only one representative cell left, resulting in a mis-detection. Besides, the cells with high SNR signals of one user can be merged with the other user's, therefore, the SNR of the representative cell for vital signs estimation can drop, resulting in degradation of the performance.

Figure 13:
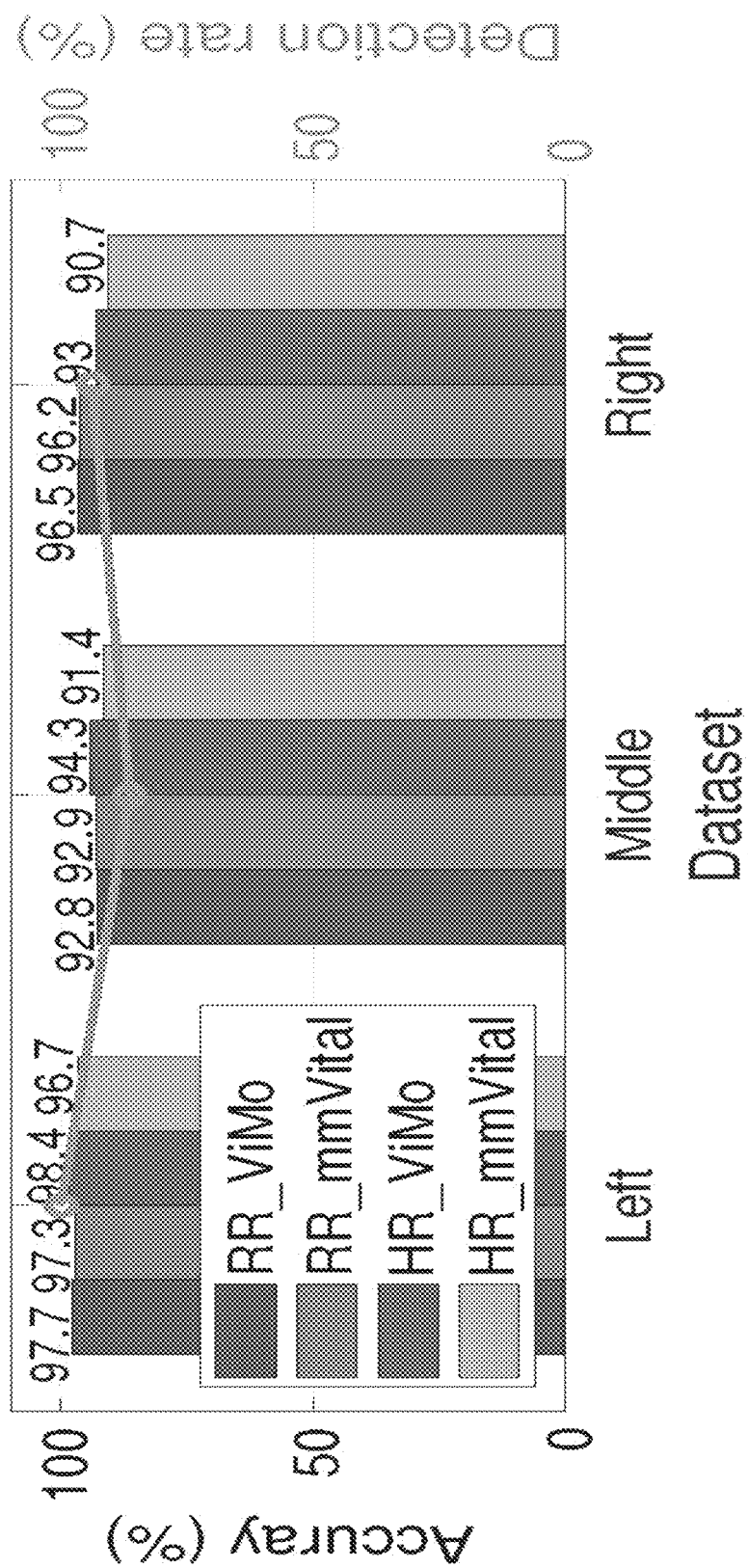
FIG. 13 illustrates an exemplary detection rate and estimation accuracy for a 3-user case, according to some embodiments of the present disclosure.

To further evaluate ViMo's accuracy for multi-user vital sign estimation, one can perform controlled experiments, where 3 users are asked to sit in parallel. ViMo detects the location of each targets and simultaneously estimate their vital signs. When mis-detection happens, one can define the relative error as 1 as before. FIG. 13 shows the mean relative accuracy of RR and HR as well as the detection rate at each location. One can see that for all the 3 locations, ViMo achieves the mean accuracy of both RR and HR over 92.8%. As for the detection rate, since the separations between the middle location and the other two locations are not large enough, and the middle location is more distant, the detection rate drops at middle location. However, the overall detection rate over time is still above 92.7% during the testing.

The present teaching discloses ViMo, a multi-person Vital sign Monitoring system using a single commercial 802.1 lad device. One can devise a multi-object stationary/non-stationary detection algorithm to locate and count human targets without any prior calibration. In addition to the instantaneous estimating breathing rates using ACF with high accuracy, one can further design a robust heart rate estimator, which eliminates the interference of the breathing signal and then estimates the heart rate leveraging both the time and frequency diversity. One can evaluate the performance of ViMo by various settings, including NLOS and motion artifacts, the most challenging scenarios for wireless vital signs monitoring. Experiment results show that ViMo can accurately monitor vital signs, with a median error of 0.19 BPM and 0.92 BPM, respectively, for RR and HR estimation.

In various embodiments of the present teaching, an algorithm for breathing and/or heartbeat detection may be performed as below.

s1: capture CSI using multiple transmit (Tx) antenna and multiple receive (Rx) antenna.

s2: apply beamforming to get directional CSI (e.g. CIR).

s3: determine direction-of-interest (DoI) by detecting object presence object in each direction. For each direction: s3a: compute power response; s3b: determine object is present in the direction (and thus the direction is DoI) if the power response is greater than threshold. The threshold may be adaptive with respect to a distance of the object; (e.g. the directional CSI may be a CIR with many taps. Each tap may be associated with a distance. Each tap may be tested with respective threshold. A threshold for a "near" tap may be larger than a threshold for a "far" tap). The threshold may be adaptively computed based on neighboring cells (e.g. each cell may be associated with a direction such that neighbor cells have neighboring directions) around cell under test (CUT) and a layer of guard cells (e.g. guard cells may be an immediate layer of cells around CUT; guard cells may not be used to compute threshold). Threshold may be adaptively computed based on CA-CFAR (cell-averaging constant false alarm rate).

s4: for each DoI (i.e. object presence is detected), compute characteristics (e.g. frequency, period, intensity, timing consistency, change/drift, etc.) of dominant periodic signal (e.g. breathing rate) by steps s4a to s4d.

s4a: determine a distance (e.g. associated with a tap of the directional CIR) associated with object presence. The DoI and the distance together define a point.

s4b: compute an auto-correlation function (ACF) (e.g. ACF of a phase of the tap of directional CIR) associated with the distance. Sometimes multiple taps/distances may be associated with object presence. ACF may be computed for each tap/distance. The multiple ACF may be combined, e.g. by weighted averaging. The respective weights may be determined based on some "importance measures" of the respective taps. Or an ACF may be computed jointly for multiple taps. Or, a dominant tap may be identified and the ACF is associated with the dominant tap.)

s4c: determine significant feature point(s) (e.g. local maximum/minimum, first local maximum, second local maximum, etc.) of the ACF. Sometimes multiple taps/distances may be associated with object presence. An ACF may be computed for each tap. The significant feature point may be computed for each ACF. The significant feature points of the ACFs of the multiple taps may be combined, e.g. by weighted average or median filtering, or maximum likelihood)

s4d: compute the characteristics (e.g. breathing rate) of the dominant periodic signal based on the significant feature point(s).

s5: for each DoI, compute characteristics of next dominant periodic signal (e.g. heart beat) by sub-steps s5a to s5b.

s5a: process the raw signal by removing/suppressing influence of the dominant periodic signal (e.g. filter the raw signal, or estimate the dominant periodic signal and subtract it from the raw signal). The raw signal may be the phase of the tap of the directional CIR. The raw signal may also be the ACF in step s4. The dominant periodic signal may be estimated by an operation on the raw signal (e.g. smoothing, low pass filtering, spline interpolation, cubic spline interpolation, polynomial fitting, polynomial fitting with order adaptively selected based on the distance/tap, etc.).

s5b: compute characteristics of the next dominant periodic signal based on the processed raw signal. The characteristics may be computed based on frequency transform, trigonometric transform, fast Fourier transform (FFT), wavelet transform, ACF, etc.

s6: determine a set of DoI associated with an object. For example, clustering may be applied to all the DoI. The set of DoI may correspond to a cluster of DoI. DoI in the set may have similar or correlated characteristics of dominant periodic signal and/or next dominant periodic signal. (e.g. breathing rate/heart rate of DoI associated with a person should be the same, and phase/intensity of breathing of different DoI may be different (e.g. due to phase lead/lag) but correlated). DoI in the set (and/or associated distance/ tag) may be adjacent/connected to a number of other DoI in the set. The set of DoI may reflect a shape/silhouette/ projection/size/area/volume/dimension/weight/body condition/view/action/activity/age/identity of the object.

s7: compute characteristics of dominant periodic signal (e.g. breathing rate) of the object (e.g. a person) by combining the characteristics of the dominant periodic signals associated with the set of DoI associated with the object.

s8: compute characteristics of next dominant periodic signal (e.g. heart rate) of the object by combining the characteristics of the next dominant periodic signal associated with the set of DoI associated with the object.

Steps s5 (and s8) can be recursively applied to determine characteristics of additional (e.g. third, fourth, etc.) dominant periodic signals. By computing the characteristics (e.g. breathing rate and/or heart rate) over time, one can track the characteristics (e.g. by compute a trajectory, or detecting regular activity/changes/deviation/anomaly/sign of danger/ sign of medical condition). Steps s3 and s4 may be swap—in that a set of distance-of-interest (each distance associated with some object presence) or a set of point-of-interest (PoI) may be computed. For each distance of interest (and its associated tag of directional CIR), all directions may be tested for object.

In various embodiments of the present teaching, another algorithm for breathing and/or heartbeat detection may be performed as below.

s1: capture CSI using multiple transmit (Tx) antenna and multiple receive (Rx) antenna.

s2: apply beamforming to get directional CSI (e.g. CIR).

s3: determine direction-of-interest (DoI) by detecting object presence in each direction. For each direction: s3a: compute magnitude of CSI (e.g. |h(theta, phi, distance)| of CIR), then time-averaged it over a time window, s3b: determine object is present in the direction (and thus the direction is DoI) if the time-averaged magnitude response is greater than a threshold T1 (e.g. maximum of a first threshold T2 and a second threshold T3). The first threshold T2 may be a 1-dimensional CFAR filtering of |h| in distance direction, and further scaled by beta in Eqn. (7). The second threshold T3 may be a 2-dimensional CFAR filtering of |h| in theta and phi direction, and further scaled by alpha in Eqn. (7).

s4: for each DoI (i.e. object presence is detected), perform motion detection by classifying object into: (a) static object (e.g. furniture), (b) stationary human (with breathing and heartbeat), (c) random body motion, by sub-steps s4a to s4e.

s4a: compute V, variance (over time in a time window) of phase of CSI (e.g. phase of h(theta, phi, distance), NOT |h| which is magnitude of h).

s4b: classify motion as "static object" if V is less than a threshold T4.

s4c: if V>T4, compute ACF and find significant feature point (e.g. first peak) P1.

s4d: classify motion as "random body motion (RBM)" if V>T6 (T6>T4) or P1 is less than a threshold T5.

s4e: classify motion as "stationary human" if V>T4 and P1>T5. Compute tentative characteristics of dominant periodic signal (e.g. breathing rate) corresponding to P1 using steps s4c1, s4c2 and s4c3.

s4e1: computing an auto-correlation function (ACF) (e.g. ACF over time of a phase of the tap of directional CIR) associated with the distance. Sometimes multiple taps/distances may be associated with object presence. They may be merged/clustered/fused (e.g. in step s6). ACF may be computed for each tap/distance. The multiple ACF may be combined, e.g. by weighted averaging. The respective weights may be determined based on some "importance measures" of the respective taps. Or an ACF may be computed jointly for multiple taps. Or, a dominant tap may be identified and the ACF is associated with the dominant tap.)

s4e2: determining significant feature point(s) (e.g. local maximum/minimum, first local maximum, second local maximum, etc.) of the ACF. Sometimes multiple taps/ distances may be associated with object presence. An ACF may be computed for each tap. The significant feature point may be computed for each ACF. The significant feature points of the ACFs of the multiple taps may be combined, e.g. by weighted average or median filtering, or maximum likelihood).

s4e3: compute the characteristics (e.g. breathing rate) of the dominant periodic signal based on the significant feature point(s).

s5: for each DoI, compute characteristics of next dominant periodic signal (e.g. heart beat) by s5a to s5b.

s5a: process the raw signal by removing/suppressing influence of the dominant periodic signal (e.g. filter the raw signal, or estimate the dominant periodic signal and subtract it from the raw signal). The raw signal may be the phase of the tap of the directional CIR. The raw signal may also be the ACF in step s4. The dominant periodic signal may be estimated by an operation on the raw signal (e.g. smoothing, low pass filtering, spline interpolation, B-spline, cubic spline interpolation, polynomial fitting, polynomial fitting with order adaptively selected based on the distance/tap, etc.). An estimation of the dominant periodic signal (e.g. breathing signal) may be computed by a constrained optimization (e.g. B-spline interpolation, minimization of a mean square error in a time window (e.g. of duration W) under a smoothness constraint). The estimate may be a linear combination of a set of pre-defined time functions (e.g. B-spline basis functions, other spline basis functions, other complete or incomplete basis functions). Coefficient of the linear combination may be computed based on a vector/matrix operation.

s5b: compute characteristics of the next dominant periodic signal based on the processed raw signal. The characteristics may be computed based on frequency transform, trigonometric transform, fast Fourier transform (FFT), wavelet transform, ACF, etc. The characteristics may also be computed by constrained optimization (e.g. minimization of an energy function subjected to a smoothness constraint). The energy function may be energy of frequency (e.g. energy of FFT of dominant-component-removed signal, the signal may be the fused/clustered signal). The smoothness constraint may be based on a logarithm of a likelihood. The heart rate may be modelled as a Markov chain with certain state transition probability. (e.g. Typically max state transition probability corresponds to no state change.) The likelihood of the Markov chain may be a product of initial probability and state transition probabilities. The logarithm of the likelihood may be a sum of individual terms.

s6: determine a set of DoI associated with an object. E.g. clustering may be applied to all the DoI. The set of DoI may correspond to a cluster of DoI. DoI in the set may have similar or correlated characteristics of dominant periodic signal and/or next dominant periodic signal. (e.g. breathing rate/heart rate of DoI associated with a person should be the same, and phase/intensity of breathing of different DoI may be different (e.g. due to phase lead/lag) but correlated). DoI in the set (and/or associated distance/tag) may be adjacent/ connected to a number of other DoI in the set. The set of DoI may reflect a shape/silhouette/projection/size/area/volume/dimension/weight/body condition/view/action/activity/age/identity of the object.

s7: compute characteristics of dominant periodic signal (e.g. breathing rate) of the object (e.g. a person) by combining the characteristics of the dominant periodic signals associated with the set of DoI associated with the object.

s8: compute characteristics of next dominant periodic signal (e.g. heart rate) of the object by combining the characteristics of the next dominant periodic signal associated with the set of DoI associated with the object.

Steps s5 (and s8) can be recursively applied to determine characteristics of additional (e.g. third, fourth, etc.) dominant periodic signals. By computing the characteristics (e.g. breathing rate and/or heart rate) over time, one can track the characteristics (e.g. by compute a trajectory, or detecting regular activity/changes/deviation/anomaly/sign of danger/sign of medical condition). Steps s3 and s4 may be swap—in that a set of distance-of-interest (each distance associated with some object presence) or a set of point-of-interest (PoI) may be computed. For each distance of interest (and its associated tag of directional CIR), all directions may be tested for object.

In various embodiments of the present teaching, breathing and/or heartbeat detection may be performed by a method as disclosed in the following clauses.

Clause 1: A method of a wireless monitoring system, comprising: transmitting a wireless probe signal from a Type 1 heterogeneous wireless device using N1 transmit (Tx) antennas of the Type 1 device through a wireless multipath channel of a venue, wherein a first object in the venue is undergoing a first repetitive motion; receiving the wireless probe signal by a Type 2 heterogeneous wireless device using N2 receive (Rx) antennas of the Type 2 device; obtaining a number of time series of channel information (CI) of the wireless multipath channel based on the received wireless probe signal using a processor, a memory communicatively coupled with the processor and a set of instructions stored in the memory, wherein each time series of CI (TSCI) is associated with a Tx antenna of the Type 1 device and a Rx antenna of the Type 2 device; computing a first information of the first repetitive motion based on the number of TSCI; monitoring the first repetitive motion of the first object based on the first information.

Clause 2: The method of the wireless monitoring system of clause 1, further comprising: wherein at least one of: the first object and a second object, is undergoing a second repetitive motion; computing a second information of the second repetitive motion based on at least one of: the number of TSCI and the first information; monitoring the second repetitive motion based on the second information.

Clause 3: The method of the wireless monitoring system of clause 2, further comprising: computing at least one analytics based on at least one of: the first information and the second information; storing at least one of: the first information, the second information, and the at least one analytics; communicating at least one of: the first information, the second information, and the at least one analytics, to at least one of: a server and a user device; generating a presentation based on at least one of: the first information, the second information, and the at least one analytics.

Clause 4: The method of the wireless monitoring system of clause 1, further comprising: wherein at least one of: the first object and a second object, is undergoing a second repetitive motion; monitoring the first repetitive motion and the second repetitive motion simultaneously based on the number of TSCI.

Clause 5: The method of the wireless monitoring system of clause 1, further comprising: wherein at least one of: the first object and a second object, is undergoing a second repetitive motion; monitoring the first repetitive motion and the second repetitive motion sequentially based on the number of TSCI.

Clause 6: The method of the wireless monitoring system of clause 1, further comprising: wherein at least one of: the first object and a second object, is undergoing a second repetitive motion; monitoring the second repetitive motion based on the monitoring of the first repetitive motion.

Clause 7: The method of the wireless monitoring system of clause 1, further comprising: wherein at least one of: the first object and a second object, is undergoing a second repetitive motion; monitoring the second repetitive motion based on a removal of an influence of the first repetitive motion.

Clause 8: The method of the wireless monitoring system of clause 7, further comprising: computing a second information of the second repetitive motion based on the number of TSCI and the removal of the influence of the first repetitive motion; monitoring the second repetitive motion based on the second information.

Clause 9: The method of the wireless monitoring system of clause 7, further comprising: removing the influence of the first repetitive motion by at least one of: estimating the influence of the first repetitive motion, eliminating the influence of the first repetitive motion, undoing the influence of the first repetitive motion, suppressing the influence of the first repetitive motion, subtracting an estimate of the first repetitive motion, dividing by the estimate of the first repetitive motion, filtering, pre-filtering, post-filtering, pre-processing, postprocessing, smoothing, lowpass filtering, bandpass filtering, highpass filtering, and another processing.

Clause 10: The method of the wireless monitoring system of clause 9, further comprising: estimating the influence of the first repetitive motion based on at least one of: merging, clustering, merging of estimates associated with more than one direction, clustering of more than one directions associated with the first repetitive motion, polynomial interpolation, piecewise polynomial interpolation, polynomial fitting, polynomial fitting with adaptive order, polynomial fitting with order adaptively selected based on at least one of: a probing rate of the wireless probing signal, a sampling rate of the received wireless probe signal, a distance of the first object, a bandwidth of the wireless multipath channel, a frequency of the first repetitive motion, and a frequency of the second repetitive motion, spline interpolation, cubic spline interpolation, B-spline, optimization, constrained optimization, minimizing a cost function subjected to smoothness constraint, minimizing an interpolation error energy term subjected to a bilinear form constraint, filtering, prefiltering, post-filtering, lowpass filtering, highpass filtering, bandpass filtering, and smoothing.

Clause 11: The method of the wireless monitoring system of clause 1, further comprising: computing a beamforming based on the number of TSCI; and computing at least one derived TSCI each associated with a direction based on the beamforming.

Clause 12: The method of the wireless monitoring system of clause 11: wherein each CI comprises a number of components each associated with a propagation delay; wherein the beamforming is computed component-wise.

Clause 13: The method of the wireless monitoring system of clause 11: wherein beamforming is applied at a particular time in a component-wise manner; wherein a derived CI at the particular time is computed on a beamforming applied to all respective CI of the number of TSCI at the particular time; wherein all CI has the same number of components; wherein each component of the derived CI at the particular time is computed based on the corresponding component of all the respective CI of the number of TSCI.

Clause 14: The method of the wireless monitoring system of clause 11, further comprising: wherein the beamforming is computed based on at least one of: analog beamforming, digital beamforming, non-adaptive beamforming, adaptive beamforming, parametric beamforming, non-parametric beamforming, compressive sensing based beamforming, minimum variance distortionless response (MVDR) beamformer, a solution to an inverse problem, direction-of-arrival estimation, tomographic reconstruction, a maximum likelihood method, a maximum entropy method, a covariance method, peak detection of discrete Fourier transform, a super-resolution method, a parameter-free super-resolution method, constrained minimization of a distortion in a target direction, constrained minimization of a power of interference and noise from directions other than the target direction, eigen-decomposition, singular value decomposition (SVD), another decomposition, a signal subspace determination, a noise subspace determination, a projection, an autoregressive (AR) model, an autoregressive-moving-average (ARMA) model, steering vector associated with the direction, an analysis of a matrix comprising a signal matrix, a correlation matrix, a covariance matrix, an autocorrelation matrix, an auto-covariance matrix, an inverse of a matrix, and another matrix, multiple signal classification (MUSIC), MUSIC-like method, time-reversal MUSIC (TR-MUSIC), Capon beamformer, Butler matrix, Pisarenko harmonic decomposition, iterative sparse asymptotic minimum variance (SAMV), spectral estimation, an Akaike Information Criterion (AIC), Bayesian information Criterion (BIC), Generalized Information Criterion (GIC), a criterion variant, a model order selection algorithm, and another beamforming method.

Clause 15: The method of the wireless monitoring system of clause 1, further comprising: computing a spatial spectrum associated with a set of propagation delay and for a set of directions based on the number of TSCI and a beamforming; and monitoring the at least one object based on the spatial spectrum, wherein each direction is associated with at least one of: an angle, an azimuth, an elevation angle, a coordinate, a steering vector, a link between a transmit antenna of the Type 1 device and a receive antenna of the Type 2 device, a path associated with an object in the direction, and another direction descriptor, wherein each propagation delay is associated with a time lag, a time delay, a time index, a propagation time, a time-of-flight, distance, a range, and another time descriptor.

Clause 16: The method of the wireless monitoring system of clause 1, further comprising: computing a set of time series of directional information (DI) based on the number of TSCI and a beamforming, each time series of DI (TSDI) associated with a direction; computing the first information of the first repetitive motion based on the TSDI, wherein the channel information (CI) comprises at least one of: channel state information (CSI), channel impulse response (CIR), and channel frequency response (CFR), wherein a directional information (DI) of the TSDI comprise at least one of: CI, channel state information (CSI), channel impulse response (CIR), channel frequency response (CFR), directional CI (DCI) associated with a direction, directional CSI (DCSI), directional CIR (DCIR), directional CFR (DCFR), a component of at least one of: the CI, CSI, CIR, CFR, DCI, DCSI, DCIR, and DCFR, associated with a distance, a magnitude of at least one of: the CI, CSI, CIR, CFR, DCI, DCSI, DCIR, DCFR and the component, a phase of at least one of the CI, CSI, CIR, CFR, DCI, DCSI, DCIR, DCFR and the component, directional weight, spatial spectrum, distribution of an information of reflected signals in the space of the venue, distribution of energy of reflected signals in the space of the venue, a heat map, and another directional information.

Clause 17: The method of the wireless monitoring system of clause 16, further comprising: testing each respective TSDI for object presence in respective direction; computing a set of direction-of-interest (DoI) comprising directions in which object presence is detected.

Clause 18: The method of the wireless monitoring system of clause 17, further comprising: computing respective test quantity based on at least one of: the respective TSDI associated with the respective direction, and a set of TSDI each associated with a respective neighboring direction, the respective test quantity associated with a particular point at a particular distance in a particular direction, the particular point associated with a particular component of a particular DI of a particular TSDI at a particular time; detecting object presence in the respective direction if the respective test quantity is greater than respective threshold. detecting object absence in the respective direction if the respective test quantity is less than the respective threshold.

Clause 19: The method of the wireless monitoring system of clause 17, further comprising: computing respective test quantity based on the respective TSDI for the respective direction and a distance; detecting object presence at the distance in the respective direction if the respective test quantity is greater than respective threshold.

Clause 20: The method of the wireless monitoring system of clause 19, further comprising: computing a point-of-interest (PoI) associated with object presence, wherein the PoI is a point corresponding to the respective direction and the distance at which object presence is detected.

Clause 21: The method of the wireless monitoring system of clause 19: wherein the respective threshold is a distance-adaptive threshold; wherein the respective threshold is based adaptively on the distance.

Clause 22: The method of the wireless monitoring system of clause 18 or clause 19: wherein the respective threshold is an direction-adaptive threshold; wherein the respective threshold is based on at least one of: constant false alarm rate (CFAR), weighted averaging of values of neighboring directions of the respective direction, weighted averaging of values of the neighboring directions excluding a guard region of immediately neighboring directions of the respective direction, cell-averaging constant false alarm rate (CA-CFAR), and another directional scheme.

Clause 23: The method of the wireless monitoring system of clause 1, further comprising: computing a time series of directional information (TSDI) associated with a direction based on the number of TSCI and a beamforming; determining a time window of the TSDI is associated with object presence; computing the first information of the first repetitive motion based on the time window of the TSDI.

Clause 24: The method of the wireless monitoring system of clause 1, further comprising: computing a time series of directional information (TSDI) based on the number of TSCI and a beamforming, wherein the TSDI is associated with a direction-of-interest (DoI) which is a direction associated with object presence, wherein each directional information (DI) of the TSDI comprises a number of components each associated with a propagation delay and a distance;

determining a first component of DI is associated with object presence in a time window; compute the first information of the first repetitive motion based on the first component of each DI in the time window of the TSDI.

Clause 25: The method of the wireless monitoring system of clause 24, further comprising: computing the first information of the first repetitive motion based on a feature of the first component of each DI in the time window of the TSDI, wherein the feature comprises at least one of: magnitude, phase, real component, imaginary component, a function of another feature, a square of magnitude, an exponential function of magnitude, and another feature.

Clause 26: The method of the wireless monitoring system of clause 25, further comprising: computing a statistical function of the feature of the first component of each DI in the time window of the TSDI, wherein the statistical function comprises at least one of: an auto-function, auto-correlation function (ACF), auto-covariance function, a function of the auto-function, a square of the auto-function, a polynomial of the auto function, a transform of the auto function, a frequency transform of the auto function, a Fourier transform of the auto function, a cross correlation, a cross covariance, a square of ACF, a polynomial of ACF, a transform of ACF, a Fourier transform of ACF, a power spectral density, a moving average, a sliding mean, a sliding variance, another statistical function, and a function of another statistical function.

Clause 27: The method of the wireless monitoring system of clause 26, further comprising: computing at least one characteristic point of the statistical function, wherein at least one the characteristic point comprises at least one of: a zero crossing, a zero crossing of a slope, a zero crossing of a high order derivative, a zero crossing of a function of the statistical function, a maximum, a maximum of slope, a maximum of high order derivative, a maximum of the function of the statistical function, a minimum, a minimum of slope, a minimum of high order derivative, a minimum of the function of the statistical function, an extremum, an extremum of slope, an extremum of high order derivative, an extremum of the function of the statistical function, a global maximum, a local maximum, a constrained maximum, a significant local maximum, a global minimum, a local minimum, a constrained minimum, a significant local minimum, a global extremum, a local extremum, a constrained extremum, a significant local extremum, a number of maxima, a number of maxima in succession, a number of minima, a number of minima in succession, a number of maxima and minima, a number of maxima and minima in succession, and another characteristic point; computing the first information of the first repetitive motion based on the at least one characteristic point.

Clause 28: The method of the wireless monitoring system of clause 25, further comprising: wherein at least one of: the first object and a second object, is undergoing a second repetitive motion; computing a second information of the second repetitive motion based on the feature of a second component of each DI in the time window of the TSDI; monitoring the second repetitive motion based on the second information.

Clause 29: The method of the wireless monitoring system of clause 28, further comprising: wherein the first object is undergoing the second repetitive motion; computing the second information of the second repetitive motion of the first object based on the feature of the first component of each DI in the time window of the TSDI; monitoring the second repetitive motion of the first object based on the second information.

Clause 30: The method of the wireless monitoring system of clause 29, further comprising: computing the second information of the second repetitive motion of the first object based on the first information.

Clause 31: The method of the wireless monitoring system of clause 29, further comprising: processing the feature of the first component of each DI in the time window of the TSDI by removing a first influence of the first repetitive motion on the feature; computing the second information of the second repetitive motion of the first object based on the processed feature.

Clause 32: The method of the wireless monitoring system of clause 31, further comprising: computing an estimate of the first influence of the first repetitive motion on the feature by suppressing a second influence of other repetitive motion on the feature; removing the first influence of the first repetitive motion on the feature by subtracting the estimate of the first influence from the feature of the first component of each DI in the time window of the TSDI.

Clause 33: The method of the wireless monitoring system of clause 16, further comprising: determining a number of direction-of-interest (DoI), each DoI being a direction associated with object presence of the first object; computing a number of TSDI, one TSDI for each DoI; computing a number of tentative first information of the first repetitive motion, each respective tentative first information based on a respective TSDI associated with a respective DoI; computing the first information based on the number of tentative first information.

Clause 34: The method of the wireless monitoring system of clause 16, further comprising: computing the first information by combining the number of tentative first information, wherein combining.

Clause 35: The method of the wireless monitoring system of clause 16, further comprising: wherein at least one of: the first object and a second object, is undergoing a second repetitive motion; determining a number of direction-of-interest (DoI), each DoI being a direction associated with object presence; computing a number of TSDI, one TSDI for each DoI; computing a number of tentative second information of the second repetitive motion, each respective tentative second information based on a respective TSDI and a removal of a respective influence of the first repetitive motion; computing a second information of the second repetitive motion based on the number of tentative second information.

Clause 36: The method of the wireless monitoring system of clause 1, further comprising: computing a set of point-of-interest (PoI) based on at least one of: the number of TSCI and a TSDI computed based on the number of TSCI and a beamforming, wherein each PoI is associated with an object presence, wherein each PoI is a point in the venue associated with a propagation delay and a direction; and monitoring the first object based on the set of PoI.

Clause 37: The method of the wireless monitoring system of clause 17, further comprising: computing a propagation-delay-of-interest (PDoI) based on the number of TSCI and the TSDI, wherein the PDoI comprises a set of selected propagation delay, each propagation delay associated with a respective distance, where each selected propagation delay is associated with the first object presence; and computing the set of PoI based on the PDoI.

Clause 38: The method of the wireless monitoring system of clause 18, further comprising: computing a variability measure of a TSDI associated with a propagation delay, wherein each directional information is computed based on the number of TSCI and a beamforming, wherein the variability measure comprises at least one of: standard deviation, variance, a measure of variation, a measure of spread, a measure of dispersion, a measure of deviation, a measure of divergence, range, interquartile range, total variation, absolute deviation, and total deviation; selecting the propagation delay and associating the propagation delay with the presence of the at least one object if the variability measure is greater than a threshold; and adding the selected propagation delay to the PDoI.

Clause 39: The method of the wireless monitoring system of clause 19, further comprising: computing a set of the variability measure associated with a set of propagation delay, each variability measure associated with a respective propagation delay; and computing the threshold as a function of the set of the variability measure, wherein the function comprises at least one of: mean, median, mode, percentile, weighted average, geometric mean, harmonic mean, trimmed mean, variance, scaling, offset, linear function, nonlinear function, monotonic non-decreasing function, monotonic non-increasing function, and a hybrid function.

Clause 40: The method of the wireless monitoring system of clause 18, further comprising: wherein the PDoI comprises at least two clusters of consecutive propagation delay values; computing a distance between two clusters of the PDoI; and expanding the PDoI by adding a missing propagation delay value between the two clusters to the PDoI if the distance is less than a threshold.

Clause 41: The method of the wireless monitoring system of clause 18, further comprising: wherein the PDoI comprises at least one disjoint cluster of consecutive propagation delay values; examining the directional quantities with associated propagation delay in the PDoI in a particular direction; identifying a cell of points in the particular direction, wherein propagation delay values associated with the cell of points are a subset of a cluster of the PDoI and each point in the cell has an associated directional information greater than a threshold; selecting in the cell of points a characteristic point associated with a propagation delay with at least one of the following characteristics of the cell: minimum, maximum, mid-point, mean, centroid with respect to (w.r.t.) the directional quantities, mean w.r.t. the directional quantities, weighted mean w.r.t. the directional quantities, median w.r.t. the directional quantities, mode w.r.t. the directional quantities, a percentile w.r.t. the directional quantities, minimum w.r.t. the directional quantities, maximum w.r.t. the directional quantities, local minimum w.r.t. the directional quantities, local maximum w.r.t. the directional quantities, minimum slope w.r.t. the directional quantities, maximum slope w.r.t. the directional quantities, local minimum slope w.r.t. the directional quantities, local maximum slope w.r.t. the directional quantities, and another characteristics; and adding the selected characteristic point as a PoI to the set of PoI.

Clause 42: The method of the wireless monitoring system of clause 18, further comprising: wherein the PDoI comprises at least one disjoint cluster of consecutive propagation delay values; examining the directional quantities with associated propagation delay in the PDoI; identifying a set of points in the venue, wherein propagation delay values associated with the set of points are a subset of a particular disjoint cluster of the PDoI and each point in the cell has an associated directional information satisfying a first criterion; and for each direction associated with the set of points: selecting at least one characteristic point based on at least one of: a subset of the set of points in the direction and the associated directional quantities, and adding the at least one selected characteristic point as a PoI to the set of PoI.

Clause 43: The method of the wireless monitoring system of clause 23, further comprising: refining the points in the PoI, wherein the refining comprises at least one of: smoothing, filtering, super-resolution, interpolation, 1-dimensional (1-D) interpolation, 2-D interpolation, 3-D interpolation, transformation, transformation from polar coordinate to rectangular coordinate, and another processing.

Clause 44: The method of the wireless monitoring system of clause 17, further comprising: cleaning the set of PoI based on the associated directional quantities by at least one of: resampling the set of PoI, weighted resampling based on the associated directional quantities, removing a PoI from the set of PoI, adding a PoI to the set of PoI, eliminating an insignificant PoI from the set of PoI, eliminating a PoI with insignificant associated directional information, eliminating a PoI with associated directional information less than a threshold, eliminating a PoI with associated directional information less than a dynamic threshold, eliminating a PoI with associated directional information less than an adaptive threshold, wherein the adaptive threshold that is monotonic non-decreasing with respect to propagation delay, eliminating a PoI with associated directional information less than an adaptive threshold, wherein the adaptive threshold is a piecewise linear function of the range associated with the propagation delay, filtering, linear filtering, nonlinear filtering, and another operation on the set of PoI.

Clause 45: The method of the wireless monitoring system of clause 17, further comprising: processing of the set of PoI and the associated directional quantities, and monitoring the at least one object based on the processing, wherein the processing comprises at least one of: clustering, identification of at least one cluster, associating the at least one cluster with the at least one object, k-mean clustering, resampling, weighted resampling, morphological operation, thresholding, silhouette analysis, computing a silhouette value associated with each PoI, computing a silhouette value based on at least one of: an average distance from a PoI to the other PoI in the same cluster of PoI, a minimum distance from the PoI to PoI in a different cluster, and a maximization of the two distance, maximizing a silhouette value, computing a similarity score between a PoI and a cluster, maximizing the similarity score, computing a characterization score regarding how similar a PoI is to its own cluster of PoI compared to a separation distance to it neighboring clusters of PoI, maximizing the characterization score, associating the set of PoI with a time stamp, processing the set of PoI jointly with a set of PoI associated with another time stamp, computing a global centroid of the set of PoI, iteratively expanding to all neighboring points that satisfy a density constraint, iteratively expanding to a set of neighboring points each with a density larger than a threshold, iteratively expanding to a set of neighboring points each with a density larger than a minimum number of points within a neighboring circle of a particular radius, projecting a set of points extended from the centroid to a plane, computing an area of the projected points from the set of points, computing the area in the plane, computing a medoid of each cluster, computing an intra-cluster medoid distance, computing a distance of every point in a cluster to its medoid, computing a distance between medoids of two clusters, and another processing.

Clause 46: The method of the wireless monitoring system of clause 17, further comprising: determining a number of clusters in the set of PoI by applying a clustering algorithm that optimizes a cost function; wherein the clustering algorithm comprises at least one of: connectivity-based clustering, hierarchical clustering, centroid-based clustering, k-means algorithm, vector quantization, distribution-based clustering, multivariate normal distribution based clustering, Gaussian-mixture based clustering, statistical distribution fitting, maximum likelihood, expectation-maximization algorithm, density-based clustering, DBSCAN, OPTICS, dense connected regions identification, subspace-based clustering, biclustering, co-clustering, two-mode-clustering, group-based clustering, model-less clustering, graph-based clustering, clique-based clustering, quasi-clique based clustering, HCS clustering, signed graph based clustering, balance theory based clustering, bifurcated graph based clustering, clustererability axiom based clustering, neural network (NN)-based clustering, self-organization map based clustering, unsupervised NN based clustering, principal component analysis, independent component analysis, hard clustering, soft clustering, fuzzy clustering, strict partition clustering, strict partition clustering with outliers, overlapping clustering, alternative clustering, multi-view clustering, and another clustering; wherein optimizing the cost function comprises at least one of: maximization, constrained maximization, global maximization, local maximization, maximization restricted to medoid, minimization, constrained minimization, global minimization, local minimization, minimization restricted to medoid, and another optimization; wherein the cost function is based on: a distance, an average distance, an intra-cluster distance, an inter-cluster distance, an average distance from a PoI in a cluster to other PoI in the same cluster, a minimum average distance from PoI in a cluster to PoI in another cluster, medoid distance, intra-cluster medoid distance, inter-cluster medoid distance, Euclidean distance, absolute distance, L-1 norm, L-2 norm, L-k norm, a silhouette value, an average silhouette value, an intra-cluster silhouette value, an inter-cluster silhouette value, a silhouette value based on a distance, a silhouette value based on an intra-cluster distance and an inter-cluster distance, a silhouette value based on an average distance from a PoI in a cluster to other PoI in the same cluster and a minimum average distance from PoI in a cluster to PoI in another cluster, a similarity score, an average similarity score, an intra-cluster similarity score, an inter-cluster similarity score, a similarity score based on a distance, a similarity score based on an intra-cluster distance and an inter-cluster distance, a similarity score based on an average distance from a PoI in a cluster to other PoI in the same cluster and a minimum average distance from PoI in a cluster to Pot in another cluster, an adaptive silhouette value based on a number of temporally neighboring silhouette values, an adaptive silhouette value based on a number of past silhouette values, an adaptive silhouette value based on application of a weighting function, wherein the weighting function is a function of clusterNum which is the number of clusters, an adaptive silhouette value based on application of a weighting function, wherein the weighting function has a maximum when clusterNum is equal to a majority value of a set of past clusterNum, and another cost function.

Clause 47: The method of the wireless monitoring system of clause 27, further comprising: validing the clusters in the set of PDoI based on a medoid distance; splitting a cluster if an intra-cluster medoid distance is greater than a threshold; and combining two clusters if the inter-cluster medoid distance is less than another threshold.

Clause 48: The method of the wireless monitoring system of clause 27, further comprising: associating the number of clusters with the at least one object; and computing at least one of: a count of the at least one objects, a location of an object based on a geometric medoid of all the points belonging to an associated cluster, and a height of the first object based on a maximum of height associated with all the points belonging to the associated cluster.

Clause 49: The method of the wireless monitoring system of clause 4, further comprising: computing a directional information for a direction based on at least one of: analog beamforming, digital beamforming, non-adaptive beamforming, adaptive beamforming, parametric beamforming, non-parametric beamforming, compressive sensing based beamforming, direction-of-arrival estimation, tomographic reconstruction, a solution to an inverse problem, a maximum likelihood method, a maximum entropy method, a covariance method, an eigen-analysis of a signal matrix or an autocorrelation matrix or a covariance matrix, eigen-decomposition, singular value decomposition (SVD), another decomposition, a projection, peak detection of discrete Fourier transform, a super-resolution method, a parameter-free superresolution method, an autoregressive (AR) model, an autoregressive-moving-average (ARMA) model, a correlation matrix, an inverse of a matrix, steering vector associated with the direction, minimum variance distortionless response (MVDR) beamformer, minimum power of interference and noise from other directions, distortionless response towards the looking direction, Capon beamformer, Butler matrix, multiple signal classification (MUSIC), MUSIC-like method, time-reversal MUSIC (TR-MUSIC), Pisarenko harmonic decomposition, iterative sparse asymptotic minimum variance (SAMV), spectral estimation, an Akaike Information Criterion (AIC), Bayesian information Criterion (BIC), Generalized Information Criterion (GIC), a criterion variant, a model order selection algorithm, a signal subspace determination, a noise subspace determination, a projection, and another digital beamforming method.

Clause 50: The method of the wireless monitoring system of clause 1: wherein the N1 antennas of the Type 1 device are arranged in a first lattice with at least one first characteristic spacing; wherein the N2 antennas of the Type 2 device are arranged in a second lattice with at least one second characteristic spacing.

wherein at least one of: the Type 1 device and the Type 2 device are placed at two different locations in the venue, the Type 1 device and the Type 2 device are collocated, being placed at the similar locations in the venue, and the Type 1 device and the Type 2 device are the same device comprising an integrated circuits (IC) that transmits and receives the probe signal and obtains the number of TSCI from the received probe signal.

Clause 51: The method of the wireless monitoring system of clause 1: wherein there are more than one pairs of Type 1 device and Type 2 device in the venue, each respective Type 2 device of a pair receiving a respective wireless signal asynchronously from the respective Type 1 device of the pair and obtaining asynchronously a respective TSCI; wherein the Type 1 device and the Type 2 device of a first pair are collocated; wherein the Type 1 device and the Type 2 device of a second pair are placed at two different locations in the venue.

Clause 52: The method of the wireless monitoring system of clause 1: wherein the first repetitive motion is at least one of: non-repetitive, repeated-once, repeated-twice, repeated-for-multiple-times, regular, irregular, periodic, pseudo-periodic, and temporarily periodic.

Clause 53: The method of the wireless monitoring system of clause 1 or clause 2: wherein at least one of: the first information (info) and the second info, comprising at least one of: a periodicity info, rhythm info, timing info, intensity info, regularity info, transient info, statistical info, normal info, deviation-from-normal info, state info, state-transition info, instantaneous info, local info, moving info, sliding info, weighted info, motion info, proximity info, presence info, movement info, gesture info, gait info, gait cycle info, action info, activity info, behavior info, daily routine info, location info, navigation info, locationing info, localization info, tracking info, coordinate info, spatial info, temporal info, trend info, history info, user info, identification info, recognition info, classification info, venue info, quantity, count info, event info, safety info, emergency info, breathing info, heartbeat info, sleep info, biometric info, cardiopulmonary info, daily activity info, chronic disease info, medical info, histogram, mean, average, moving average, weighted average, weighted mean, trimmed mean, variance, standard deviation, correlation, correlation coefficient, median, mode, weighted median, distribution, statistics, conditional analytics, conditional statistics, conditional mean, conditional variance, conditional median, conditional mode, short-term correlation, long-term correlation, auto-correlation, cross-correlation, correlation indicator, short-term covariance, long-term covariance, auto-covariance, cross-covariance, covariance indicator, measure of variation, variability, spread, dispersion, deviation, divergence, range, interquartile range, total variation, absolute deviation, total deviation, arithmetic mean, geometric mean, harmonic mean, trimmed mean, percentile, quartile, indicator, indication, early indication, instantaneous indication, contemporaneous indication, delayed indication, pattern, one-time pattern, repeating pattern, evolving pattern, time pattern, mutually exclusive pattern, related pattern, correlated pattern, typical pattern, atypical pattern, start, stop, pause, resume, presence, absence, proximity, event, normal event, suspicious event, dangerous event, alarming event, warning, belief, collision, amplitude, intensity, strength, frequency, rate, period, phase, phase lag, cycle, time, timing, starting time, ending time, duration, time lag, offset, shift, deviation, variation, change, alteration, adjustment, adaptation, orientation, direction, axis, location, distance, displacement, height, speed, acceleration, angle, angular distance, angular speed, angular acceleration, radial distance, angular displacement, change, abrupt change, gradual change, change in frequency, change in period, transition, biometric, breathing rate, breathing period, breathing timing, breathing rhythm, breathing pattern, breathing intensity, breathing amplitude, breathing depth, breathing variability, breathing rate variability, heart rate, heart period, heartbeat, heartbeat timing, heart rhythm, heartbeat intensity, heartbeat amplitude, heartbeat variability, heart rate variability (HRV), state, sleep state, rapid-eye-movement (REM) state, non-REM (NREM) state, awake state, security state, motion state, motion state, motion intensity, motion type, motion classification, static motion, non-static motion, stationary motion, non-stationary motion, statistical parameters, analytics, object type, object classification, static object, non-static object, active object, inactive object, active non-static object, inactive non-static object, at least one of: indication, suggestion, sign, indicator, verifier, detection and symptom, of at least one of: a disease, condition, situation, trend, cycle, behavior, pattern, tendency, inclination, cause-and-effect, and correlation, and another information.

Clause 54: The method of the wireless monitoring system of clause 18, wherein the respective test quantity comprise at least one of: at least one of: a quantity, vector, matrix, data, data structure, data set, feature, magnitude, phase, CI, CI component, directional information (DI) and DI component, that may be at least one of: dominant, representative, characteristic, indicative, archetypal, paradigmatic, exemplary, key, prominent, common, shared, typical, prototypical, averaged, regular, persistent, usual, normal, atypical, unusual, abnormal, and unrepresentative, similarity, similarity measure, similarity score, similarity between two CI, similarity between two CI, similarity between two vectors of CI, similarity between two windows of CI, similarity between two windows of CI with unequal window length, similarity between two DI, similarity between two DI, similarity between two vectors of DI, similarity between two windows of DI, similarity between two windows of DI with unequal window length, distance score, distance measure between two CI, distance measure between two vectors of CI, distance measure between two windows of CI, distance measure between two windows of CI aligned and mapped, distance measure between two windows of CI aligned using dynamic time warping (DTW), distance measure between two DI, distance measure between two vectors of DI, distance measure between two windows of DI, distance measure between two windows of DI aligned and mapped, distance measure between two windows of DI aligned using dynamic time warping (DTW), Euclidean distance, absolute distance, L-1 distance, L-2 distance, L-k distance, weighted distance, graph distance, distance metric, norm, L-1 norm, L-2 norm, L-k norm, pseudo metric, extended metric, quasi-metric, metametric, semimetric, premetric, pseudoquasimetric, metric tensor, bilinear form, correlation, correlation of two CI, correlation of two DI, correlation coefficient, correlation indicator, autocorrelation, a feature of autocorrelation function (ACF), cross correlation, inner product, dot product, outer product, covariance, auto-covariance, cross covariance, discrimination score, magnitude, phase, average, time average, spatial average, mean, weighted average, time average, spatial average, directional average, radial average, variance, standard deviation, variability measure, variability metric, total variation, absolute variation, measure of variation, spread, dispersion, deviation, total deviation, divergence, likelihood, probability distribution function, sample distribution, moment generating function, expected value, expected function, total variation, absolute variation, measure of variation, spread, dispersion, deviation, total deviation, divergence, range, interquartile range, weighted mean, trimmed mean, arithmetic mean, geometric mean, harmonic mean, conditional mean, median, mode, percentile, linear combination, transformation, location, localization, location coordinate, change in location, position, map position, height, horizontal location, vertical location, distance, displacement, speed, acceleration, rotational speed, rotational acceleration, direction, angle of motion, azimuth, direction of motion, rotation, path, deformation, transformation, shrinking, expanding, positional characteristics, gait, gait cycle, gesture, handwriting, head motion, mouth motion, hand motion, leg motion, body motion, heart motion, internal organ motion, tool motion, machine motion, complex motion, combination of multiple motions, motion trend, repeatedness, periodicity, pseudo-periodicity, impulsiveness, sudden-ness, fall-down occurrence, recurrence, transient event, behavior, transient behavior, period, time trend, temporal profile, temporal characteristics, occurrence, time, timing, starting time, initiating time, ending time, duration, history, motion classification, motion type, change, temporal change, frequency change, CI change, DI change, timing change, gait cycle change, frequency spectrum, frequency characteristics, frequency, presence, absence, proximity, approaching, receding, object identifier, object composition, mouth-related rate, eye-related rate, walking rate, breathing rate, heart rate, periodicity measure, periodicity metric, tidal volume, depth of breath, inhale time, exhale time, inhale time to exhale time ratio, airflow rate, heart heat-to-beat interval, heart rate variability, motion detection statistics, motion identification statistics, motion recognition statistics, signal statistics, signal dynamics, anomaly, parameter, motion magnitude, motion phase, motion signal transformation, motion feature, presence of object, absence of object, entrance of object, exit of object, change of object, motion cycle, motion count, gait cycle, motion rhythm, deformation motion, size, length, area, volume, capacity, shape, form, tag, starting/initiating location, ending location, starting/initiating quantity, ending quantity, event occurrence, event statistics, fall-down event, security event, accident event, home event, office event, factory event, warehouse event, manufacturing event, assembly line event, maintenance event, vehicle-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and another test quantity.

Clause 55: The method of the wireless monitoring system of clause 18, further comprising: computing the respective test quantity based on at least one of: a DI of a TSDI, a time associated with the DI, a component of the DI, at least one of: a time lag, a point in the venue, a direction, a distance, a geometric coordinate and a map coordinate, associated with the component of the DI, a quantity associated with at least one of: the DI and the component of the DI comprising at least one of: time, the DI, the DI component, magnitude, vector norm, DI magnitude, DI component magnitude, phase, DI phase, DI component phase, conjugate, real part, imaginary part, sign, square, cube, root, power, magnitude square, magnitude cube, magnitude to a power, absolute value, and collection of more than one quantities, a unitary function of the quantity comprising at least one of: linear function, nonlinear function, piecewise linear function, polynomial, trigonometric function, sine, cosine, tangent, elliptical function, parabolic function, hyperbolic function, logarithmic function, exponential function, algebraic function, special function, game function, zeta function, Bessel function, Beta function, Gamma function, Gaussian function, error function, complementary error function, Poisson function, inverse function, transcendental function, absolute function, logical function, derivative with respect to at least one of: time, direction, and distance, higher order derivative, thresholding, soft threshold, hard threshold, indicator function, clipping, soft clipping, quantization, mapping, shifting, scaling, zero crossing, group, set, collection, union, intersection, composite function, and function of function, a neighborhood of the DI, a neighboring DI, a temporal neighborhood of the time of the DI, a temporally neighboring DI in the temporal neighborhood, a spatial neighborhood of the point, a spatially neighboring DI in the spatial neighborhood, a directional neighborhood of the direction, a directionally neighboring DI, a radial neighborhood of the distance, a radially neighboring DI, a geometric neighborhood associated with at least one of: the geometric coordinate and the map coordinate, a geometrically neighboring DI, a set of at least one of: neighboring DI, temporally neighboring DI, spatially neighboring DI, directionally neighboring DI, a radially neighboring DI, and a geometric neighboring DI, a multivariate function of the quantity associated with a set of neighboring DI comprising at least one of: average, time average, spatial average, mean, variance, standard deviation, total variation, absolute variation, measure of variation, spread, dispersion, deviation, total deviation, divergence, range, interquartile range, weighted mean, trimmed mean, arithmetic mean, geometric mean, harmonic mean, conditional mean, median, mode, percentile, linear combination, transformation, short-term statistics, long term statistics, autocorrection function (ACF), power spectral density (PSD), cross correlation function, covariance function, moment generating function, filtering, convolution, linear filtering, piecewise linear filtering, nonlinear filtering, low pass filtering, bandpass filtering, highpass filtering, windowed filtering, constant-false-alarm-rate (CFAR) windowed filtering, ID-CFAR filtering, 2D-CFAR filtering, 3D-CFAR filtering, median filtering, rank filtering, matched filtering, particle filter, adaptive filtering, smoothing, first derivative, second derivative, high order derivative, frequency transform, discrete time transform, discrete transform, Fourier transform, DFT, FFT, cosine transform, DCT, sine transform, DST, Laplace transform, Hadamard transform, Hilbert transform, wavelet transform, trigonometric transform, sine transform, cosine transform, DCT, integer transform, sparse transform, graph-based transform, projection, orthogonal projection, non-orthogonal projection, overcomplete projection, eigen-decomposition, singular value decomposition (SVD), principle component analysis (PCA), independent component analysis (ICA), maximization, minimization, synchronization, time correction, phase correction, magnitude correction, normalization, vector quantization, clustering, matching pursuit, compressive sensing, neural network, machine learning, deep learning, training, discriminative training, detection, estimation, classification, identification, sliding function, moving function, stochastic function, deterministic function, periodic function, repeated function, sparse approximation, regression, smoothing, zero crossing, denoising, enhancement, coding, encryption, resampling, up-sampling, down-sampling, random sampling, importance sampling, interpolation, extrapolation, repetition, zero padding, preprocessing, postprocessing, group, set, collection, union, intersection, logical operation, composite function, and function of function, the multivariate function of the quantity of a set of neighboring DI, the multivariate function of the unitary function of the quantity of the set of neighboring DI, the multivariate function of the quantity of a set of temporally neighboring DI, the multivariate function of the unitary function of the quantity of the set of temporally neighboring DI, the multivariate function of the quantity of a set of spatially neighboring DI, the multivariate function of the unitary function of the quantity of the set of spatially neighboring DI, the multivariate function of the quantity of a set of directionally neighboring DI, the multivariate function of the unitary function of the quantity of the set of directionally neighboring DI, the multivariate function of the quantity of a set of radially neighboring DI, the multivariate function of the unitary function of the quantity of the set of radially neighboring DI, the multivariate function of the quantity of a set of geometrically neighboring DI, the multivariate function of the unitary function of the quantity of the set of geometrically neighboring DI, and another test quantity.

Clause 56: The method of the wireless monitoring system of clause 18, further comprising: computing the respective threshold based on at least one of: respective predefined threshold, respective fixed threshold, respective adaptive threshold, scaling of thresholds, maximum of thresholds, minimum of thresholds, weighted average of thresholds, a DI of a TSDI, a time associated with the DI, a component of the DI, at least one of: a time lag, a point in the venue, a direction, a distance, a geometric coordinate and a map coordinate, associated with the component of the DI, a neighborhood of the DI, a neighboring DI, a temporal neighborhood of the time of the DI, a temporally neighboring DI in the temporal neighborhood, a spatial neighborhood of the point, a spatially neighboring DI in the spatial neighborhood, a directional neighborhood of the direction, a directionally neighboring DI, a radial neighborhood of the distance, a radially neighboring DI, a geometric neighborhood associated with at least one of: the geometric coordinate and the map coordinate, a geometrically neighboring DI, a set of at least one of: neighboring DI, temporally neighboring DI, spatially neighboring DI, directionally neighboring DI, a radially neighboring DI, and a geometric neighboring DI, a quantity associated with at least one of: the DI and the component of the DI comprising at least one of: time, the DI, the DI component, magnitude, vector norm, DI magnitude, DI component magnitude, phase, DI phase, DI component phase, conjugate, real part, imaginary part, sign, square, cube, root, power, magnitude square, magnitude cube, magnitude to a power, absolute value, and collection of more than one quantities, processing of the quantity associated with the set of the neighboring DI, processing of the quantity associated with the set of temporally neighboring DI, processing of the quantity associated with the set of spatially neighboring DI, processing of the quantity associated with the set of directionally neighboring DI, processing of the quantity associated with the set of radially neighboring DI, weighted averaging of the quantity associated with neighboring DI excluding an immediate neighborhood of DI, statistics of the quantity associated with neighboring DI, function of a neighborhood of DI excluding an immediate neighborhood of DI, function of a neighboring cell of DI excluding an immediate neighborhood of DL filtering, convolution, linear filtering, piecewise linear filtering, nonlinear filtering, low pass filtering, averaging, bandpass filtering, highpass filtering, windowed filtering, constant-false-alarm-rate (CFAR) windowed filtering, 1D-CFAR filtering, 2D-CFAR filtering, 3D-CFAR filtering, mean filtering, median filtering, rank filtering, mode filtering, trimmed mean filtering, percentile filtering, matched filtering, particle filter, adaptive filtering, smoothing, first derivative, second derivative, high order derivative, average, time average, spatial average, mean, variance, standard deviation, total variation, absolute variation, measure of variation, spread, dispersion, deviation, total deviation, divergence, range, interquartile range, weighted mean, trimmed mean, arithmetic mean, geometric mean, harmonic mean, conditional mean, median, mode, percentile, linear combination, transformation, short-term statistics, long term statistics, autocorrection function (ACF), power spectral density (PSD), cross correlation function, covariance function, moment generating function, and another threshold.

Clause 57: The method of the wireless monitoring system of clause 18, further comprising: detecting a presence of the first object at a particular time at a particular point at a particular distance in a particular direction based on a determination that a test quantity associated with a particular component of a particular DI of a particular TSDI is greater than a respective threshold, wherein the particular TSDI is associated with the particular direction, wherein the particular DI is associated the particular time, wherein the particular component is associated with the particular distance time.

Clause 58: The method of the wireless monitoring system of clause 57, further comprising: computing at least one of: a second test quantity and a third test quantity, based on at least one of: the particular TSDI associated with the particular direction, a set of directionally neighboring TSDI associated with a set of neighboring directions of the particular direction, a set of directionally neighboring DI in the set of neighboring directions of the particular point, each directionally neighboring DI from one of the directionally neighboring TSDI, a set of directionally neighboring DI in a directional neighborhood of the particular point, a set of directionally neighboring DI associated with the particular time, the particular DI of the particular TSDI associated with the particular time, a set of neighboring DI of the particular TSDI associated with a set of neighboring time stamps of the particular DI, a time window of DI of the particular TSDI associated with the particular DI, a set of temporally neighboring DI in a temporal neighborhood of the particular time of the particular CI, a set of temporally neighboring DI in the particular TSDI, a set of temporally neighboring DI in directionally neighboring TSDI, the particular component of the particular DI of the particular TSDI, a set of neighboring components of the particular DI of the particular TSDI associated with the particular component, a set of radially neighboring DI components in the particular DI of the particular TSDI associated with a set of neighboring component index of the particular component, a section of components of the particular DI of the particular TSDI associated with the particular component, a set of radially neighboring DI in a radial neighborhood of the particular point, a set of radially neighboring DI a set of spatially neighboring DI in a spatial neighborhood of the particular point, a set of spatially neighboring DI in a set of neighboring distance of the particular point, and a set of neighboring DI in a neighborhood of the particular point; classifying the first object at the particular point, based on at least one of: the second test quantity and the third test quantity, to be at least one of: a static object, non-static object, active object, inactive object, active non-static object, inactive non-static object, object with static motion (no motion), object with non-static motion (non-zero motion), object with stationary motion (e.g. breathing, heartbeat, regular motion, periodic motion, regular random motion, periodic random motion), object with at least two stationary motions: one dominant and one next dominant, object with non-stationary motion (e.g. transient motion, irregular motion, irregular random motion, non-repeating motion, one-time motion), object with periodic motion (e.g. breathing, heartbeat, regular motion, stationary motion, periodic random motion), object with at least two periodic motions: one dominant and one next dominant, object with non-periodic motion, object with random motion (e.g. irregular random motion, random body motion), object with non-random motion (e.g. random body motion), object with regular motion (e.g. breathing, heartbeat, regular motion, stationary motion, periodic random motion), object with irregular motion (e.g. transient motion, random motion, random body motion, unpredictable motion, impulsive motion, irregular random motion, non-repeating motion, one-time motion), another class of object and object with another class of motion.

Clause 59: The method of the wireless monitoring system of clause 58, further comprising at least one of: classifying the first object at the particular point as a static object if the second test quantity is less than a second threshold T2; classifying the first object at the particular point as a non-static object if the second test quantity is greater than T2; classifying the first object as an active non-static object if the second test quantity is greater than a third threshold T3 greater than T2; classifying the first object as the active non-static object if the second test quantity is between T2 and T3 and a third test quantity is less than a fourth threshold T4; or classifying the first object as an inactive non-static object if the second test quantity is between T2 and T3 and the third test quantity is greater than a fourth threshold T4.

Clause 60: The method of the wireless monitoring system of clause 58, further comprising at least one of: classifying the first object at the particular point as a static object if the second test quantity is less than a second threshold T2; classifying the first object at the particular point as a non-static object if the second test quantity is greater than T2; classifying the first object as an inactive non-static object if the second test quantity is greater than T2 but less than a third threshold T3 and a third test quantity is greater than a fourth threshold T4; and classifying the first object as an active non-static object otherwise.

Clause 61: The method of the wireless monitoring system of clause 58, further comprising at least one of: classifying a motion of the first object at the particular point as static if the second test quantity is less than a second threshold T2; classifying the motion of the first object as non-static if the second test quantity is greater than T2; classifying the motion of the first object as non-static and at least one of: non-stationary, non-periodic, irregular, and random, if the second test quantity is greater than a third threshold T3 which is greater than T2; classifying the motion of the first object as non-static and at least one of: non-stationary, non-periodic, irregular, and random, if the second test quantity is between T2 and T3 and a third test quantity is less than a fourth threshold T4; and classifying the motion of the first object as non-static and at least one of: stationary, periodic, regular, and non-random, if the second test quantity is between T2 and T3 and the third test quantity is greater than a fourth threshold T4.

Clause 62: The method of the wireless monitoring system of clause 58, further comprising at least one of: classifying a motion of the first object at the particular point as static if the second test quantity is less than a second threshold T2; classifying a motion of the first object at the particular point as non-static if the second test quantity is greater than a second threshold T2; classifying the motion of the first object as non-static and at least one of: stationary, periodic, regular, and non-random, if the second test quantity is greater than T2 but less than a third threshold T3 and a third test quantity is greater than a fourth threshold T4; and classifying the motion of the first object as non-static and at least one of: non-stationary, non-periodic, irregular, and random, otherwise.

Clause 63: The method of the wireless monitoring system of clause 58, further comprising at least one of: classifying the first object as an inactive non-static object if the third test quantity is greater than a fourth threshold T4; classifying the first object as an active non-static object if the third test quantity is less than T4 and the second test quantity is greater than a second threshold T2; classifying the first object as a static object if the third test quantity is less than T4 and the second test quantity is less than T2; classifying the first object as a non-static object if the second test quantity is greater than T2.

Clause 64: The method of the wireless monitoring system of clause 58, further comprising at least one of: classifying a motion of the first object as non-static and at least one of: stationary, periodic, regular, and non-random, if the third test quantity is greater than a fourth threshold T4; classifying a motion of the first object as non-static and at least one of: non-stationary, non-periodic, irregular, and random, if the third test quantity is less than T4 and the second test quantity is greater than a second threshold T2; classifying a motion of the first object as a static object if the third test quantity is less than T4 and the second test quantity is less than T2; and classifying a motion of the first object as a non-static object if the third test quantity is greater than T4 or the second test quantity is greater than T2.

Clause 65: The method of the wireless monitoring system of clause 58, wherein at least one of: the second test quantity and the third test quantity, comprise at least one of: at least one of: a quantity, vector, matrix, data, data structure, data set, feature, magnitude, phase, CI, CI component, directional information (DI) and DI component, that may be at least one of: dominant, representative, characteristic, indicative, archetypal, paradigmatic, exemplary, key, prominent, common, shared, typical, prototypical, averaged, regular, persistent, usual, normal, atypical, unusual, abnormal, and unrepresentative, similarity, similarity measure, similarity score, similarity between two CI, similarity between two CI, similarity between two vectors of CI, similarity between two windows of CI, similarity between two windows of CI with unequal window length, similarity between two DI, similarity between two DI, similarity between two vectors of DI, similarity between two windows of DI, similarity between two windows of DI with unequal window length, distance score, distance measure between two CI, distance measure between two vectors of CI, distance measure between two windows of CI, distance measure between two windows of CI aligned and mapped, distance measure between two windows of CI aligned using dynamic time warping (DTW), distance measure between two DI, distance measure between two vectors of DI, distance measure between two windows of DI, distance measure between two windows of DI aligned and mapped, distance measure between two windows of DI aligned using dynamic time warping (DTW), Euclidean distance, absolute distance, L-1 distance, L-2 distance, L-k distance, weighted distance, graph distance, distance metric, norm, L-1 norm, L-2 norm, L-k norm, pseudo metric, extended metric, quasimetric, metametric, semimetric, premetric, pseudoquasimetric, metric tensor, bilinear form, correlation, correlation of two CI, correlation of two DI, correlation coefficient, correlation indicator, autocorrelation function (ACF), ACF of phase, ACF of phase of quantity, ACF of phase of component of DI (or CI), ACF of phase of a particular component of a particular DI of a particular TSDI (or a particular CI of a particular TSCI), a feature of ACF, local maximum of ACF, first peak of ACF, magnitude of local maximum, magnitude of first peak, cross correlation, inner product, dot product, outer product, covariance, auto-covariance, cross covariance, discrimination score, magnitude, phase, average, time average, spatial average, mean, weighted average, time average, spatial average, directional average, radial average, variance, variance of phase, variance of magnitude, standard deviation, variability measure, variability metric, total variation, absolute variation, mean square variation, measure of variation, spread, dispersion, deviation, total deviation, mean square deviation, divergence, spatial variability measure, spatial variability metric, spatial variance, temporal variance, temporal standard deviation, temporal variability measure, temporal variability metric, temporal total variation, temporal absolute variation, temporal mean square variation, temporal measure of variation, temporal spread, temporal dispersion, temporal deviation, temporal total deviation, temporal mean square deviation, temporal divergence, likelihood, probability distribution function, sample distribution, moment generating function, expected value, expected function, total variation, absolute variation, measure of variation, spread, dispersion, deviation, total deviation, divergence, range, interquartile range, weighted mean, trimmed mean, arithmetic mean, geometric mean, harmonic mean, conditional mean, median, mode, percentile, linear combination, transformation, location, localization, location coordinate, change in location, position, map position, height, horizontal location, vertical location, distance, displacement, speed, acceleration, rotational speed, rotational acceleration, direction, angle of motion, azimuth, direction of motion, rotation, path, deformation, transformation, shrinking, expanding, positional characteristics, gait, gait cycle, gesture, handwriting, head motion, mouth motion, hand motion, leg motion, body motion, heart motion, internal organ motion, tool motion, machine motion, complex motion, combination of multiple motions, motion trend, repeatedness, periodicity, pseudo-periodicity, impulsiveness, sudden-ness, fall-down occurrence, recurrence, transient event, behavior, transient behavior, period, frequency, time trend, temporal profile, temporal characteristics, occurrence, time, timing, starting time, initiating time, ending time, duration, history, motion classification, motion type, change, temporal change, frequency change, CI change, DI change, timing change, gait cycle change, frequency spectrum, frequency characteristics, frequency, presence, absence, proximity, approaching, receding, object identifier, object composition, mouth-related rate, eye-related rate, walking rate, breathing rate, heart rate, periodicity measure, periodicity metric, tidal volume, depth of breath, inhale time, exhale time, inhale time to exhale time ratio, airflow rate, heart heat-to-beat interval, heart rate variability, motion detection statistics, motion identification statistics, motion recognition statistics, signal statistics, signal dynamics, anomaly, parameter, motion magnitude, motion phase, motion signal transformation, motion feature, presence of object, absence of object, entrance of object, exit of object, change of object, motion cycle, motion count, gait cycle, motion rhythm, deformation motion, size, length, area, volume, capacity, shape, form, tag, starting/initiating location, ending location, starting/ initiating quantity, ending quantity, event occurrence, event statistics, fall-down event, security event, accident event, home event, office event, factory event, warehouse event, manufacturing event, assembly line event, maintenance event, vehicle-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and another test quantity.

Clause 66: The method of the wireless monitoring system of clause 18, further comprising: computing at least one of: the second test quantity and the third test quantity, based on at least one of: a DI of a TSDI, a time stamp associated with the DI, a component of the DI, at least one of: a time lag, a point in the venue, a direction, a distance, a geometric coordinate and a map coordinate, associated with the component of the DI, a quantity associated with at least one of: the DI and the component of the DI comprising at least one of: time, the DL the DI component, magnitude, vector norm, DI magnitude, DI component magnitude, phase, DI phase, DI component phase, conjugate, real part, imaginary part, sign, square, cube, root, power, magnitude square, magnitude cube, magnitude to a power, absolute value, and collection of more than one quantities, a unitary function of the quantity comprising at least one of: linear function, nonlinear function, piecewise linear function, polynomial, trigonometric function, sine, cosine, tangent, elliptical function, parabolic function, hyperbolic function, logarithmic function, exponential function, algebraic function, special function, game function, zeta function, Bessel function, Beta function, Gamma function, Gaussian function, error function, complementary error function, Poisson function, inverse function, transcendental function, absolute function, logical function, derivative with respect to at least one of: time, direction, and distance, higher order derivative, thresholding, soft threshold, hard threshold, indicator function, clipping, soft clipping, quantization, mapping, shifting, scaling, zero crossing, group, set, collection, union, intersection, composite function, and function of function, a neighborhood of the DI, a neighboring DI, a temporal neighborhood of the time of the DL a temporally neighboring DI in the temporal neighborhood, a spatial neighborhood of the point, a spatially neighboring DI in the spatial neighborhood, a directional neighborhood of the direction, a directionally neighboring DI, a radial neighborhood of the distance, a radially neighboring DI, a geometric neighborhood associated with at least one of: the geometric coordinate and the map coordinate, a geometrically neighboring DI, a set of at least one of: neighboring DI, temporally neighboring DI, spatially neighboring DI, directionally neighboring DI, a radially neighboring DI, and a geometric neighboring DI, a multivariate function of the quantity associated with a set of neighboring DI comprising at least one of: average, time average, spatial average, mean, variance, temporal variance, spatial variance, standard deviation, total variation, absolute variation, measure of variation, spread, dispersion, deviation, total deviation, divergence, range, interquartile range, weighted mean, trimmed mean, arithmetic mean, geometric mean, harmonic mean, conditional mean, median, mode, percentile, linear combination, transformation, short-term statistics, long term statistics, autocorrection function (ACF), power spectral density (PSD), cross correlation function, covariance function, moment generating function, filtering, convolution, linear filtering, piecewise linear filtering, nonlinear filtering, low pass filtering, bandpass filtering, highpass filtering, windowed filtering, constant-false-alarm-rate (CFAR) windowed filtering, 1 D-CFAR filtering, 2D-CFAR filtering, 3D-CFAR filtering, median filtering, rank filtering, matched filtering, particle filter, adaptive filtering, smoothing, first derivative, second derivative, high order derivative, frequency transform, discrete time transform, discrete transform, Fourier transform, DFT, FFT, cosine transform, DCT, sine transform, DST, Laplace transform, Hadamard transform, Hilbert transform, wavelet transform, trigonometric transform, sine transform, cosine transform, DCT, integer transform, sparse transform, graph-based transform, projection, orthogonal projection, non-orthogonal projection, over-complete projection, eigen-decomposition, singular value decomposition (SVD), principle component analysis (PCA), independent component analysis (ICA), maximization, minimization, synchronization, time correction, phase correction, magnitude correction, normalization, vector quantization, clustering, matching pursuit, compressive sensing, neural network, machine learning, deep learning, training, discriminative training, detection, estimation, classification, identification, sliding function, moving function, stochastic function, deterministic function, periodic function, repeated function, sparse approximation, regression, smoothing, zero crossing, denoising, enhancement, coding, encryption, resampling, up-sampling, down-sampling, random sampling, importance sampling, interpolation, extrapolation, repetition, zero padding, preprocessing, postprocessing, group, set, collection, union, intersection, logical operation, composite function, and function of function, the multivariate function of the quantity of a set of neighboring DI, the multivariate function of the unitary function of the quantity of the set of neighboring DI, the multivariate function of the quantity of a set of temporally neighboring DI, the multivariate function of the unitary function of the quantity of the set of temporally neighboring DI, the multivariate function of the quantity of a set of spatially neighboring DI, the multivariate function of the unitary function of the quantity of the set of spatially neighboring DI, the multivariate function of the quantity of a set of directionally neighboring DI, the multivariate function of the unitary function of the quantity of the set of directionally neighboring DI, the multivariate function of the quantity of a set of radially neighboring DI, the multivariate function of the unitary function of the quantity of the set of radially neighboring DI, the multivariate function of the quantity of a set of geometrically neighboring DI, the multivariate function of the unitary function of the quantity of the set of geometrically neighboring DI, and another test quantity.

Clause 67: The method of the wireless monitoring system of clause 18, further comprising: identifying a set of direction-of-interest (DoI) in which object presence is detected; identifying a set of points of interest (PoI), wherein each PoI is a point in the venue associated with a respective DoI and a respective distance in the DoI, wherein each PoI is associated with a respective component of a respective DI of a respective TSDI associated with the respective DoI, wherein object presence is detected at the Pot based on a respective test quantity associated with the respective component of the respective DI of the respective TSDI being greater than a respective threshold; computing at least one of: a cluster of PoI and a cluster of DoI, based on the set of PoI and DoI; and computing at least one of: a shape, surface, manifold, skeleton, silhouette, size, weight, health condition, well-being, center, centerline, cluster center, location, movement, motion, activity, gesture, gait, handwriting, of the first object based on at least one of: the PoI cluster, the DoI cluster, at least one of: spatial behavior, temporal behavior and spatio-temporal behavior of at least one of: the PoI cluster and the DoI cluster, a spatial behavior of at least one of: the PoI cluster and the DoI cluster, a set of DI associated with at least one of: the cluster of PoI and the cluster of DoI, a set of DI components associated with the set of DI associated with at least one of: the cluster of PoI and the cluster of DoI, a DI of a TSDI associated with at least one of: a respective PoI and a respective DoI, a DI component of the DI of the TSDI associated with at least one of: the respective PoI and the respective DoI, a CI associated with the DI, a CI component associated with the DI component, and at least one of: spatial behavior, temporal behavior and spatio-temporal behavior of at least one of: the DI, the DI component, the CI, the CI component, the set of DI and the set of DI components.

Clause 68: The method of the wireless monitoring system of clause 67, further comprising: combining two PoI into a PoI cluster if a distance between the two PoI is less than a threshold.

Clause 69: The method of the wireless monitoring system of clause 67, further comprising: combining two DoI into a DoI cluster if a distance between the two DoI is less than a threshold.

Clause 70: The method of the wireless monitoring system of clause 67, further comprising: computing at least one of: the PoI cluster and the DoI cluster, based on at least one of: connectivity-based clustering, connectivity model, hierarchical clustering, distance connectivity, single linkage clustering, complete linkage clustering, centroid-based clustering, centroid model, k-means algorithm, k-medoids, k-medians, fuzzy c-means, distribution-based clustering, distribution model, statistical distribution, normal distribution, multivariate Gaussian distribution expectation-maximization algorithm, density-based clustering, density model, DBSCAN, OPTICS, connected dense regions in data space, subspace-based clustering, subspace model, biclustering, co-clustering, two-mode-clustering, cluster members, relevant attributes, group-based clustering, group model, grouping information, graph-based clustering, graph-based model, clique, subset of nodes in a graph, nodes connected by an edge, relaxation of complete connectivity requirement, quasi-cliques, HCS clustering algorithm, signed-graph-based clustering, signed graph model, bifurcated graph, neural-network clustering, unsupervised neural network, self-organizing map, principal component analysis, independent component analysis, grid-based clustering, hard clustering, soft clustering, fuzzy clustering, overlapping clustering, alternative clustering, and another clustering algorithm.

Clause 71: The method of the wireless monitoring system of clause 67, further comprising: computing at least one of: the center, centerline, cluster center, and location as at least one of DoI and PoI associated with at least one of: largest periodicity measure, largest periodicity metric, largest dominant periodic signal, largest periodic intensity, largest autocorrelation function (ACF) peak, largest magnitude ACF peak, largest phase ACF peak, largest dominant frequency component, largest repeatedness, least impulsiveness, largest variability measure, largest variability metric, largest variability intensity, largest variation measure, largest variation metric, largest variation intensity, largest variance, largest standard deviation, largest magnitude variance, largest phase variance, largest spread, largest dispersion, largest deviation, largest divergence, largest range, largest total variation, largest absolute deviation, largest total deviation, centroid of the cluster, weighted centroid of the cluster, skeleton of the cluster, topological skeleton of the cluster, thinning of the cluster, topology-preserving thinning of the cluster, pruning of the cluster, topology-preserving pruning of the cluster, medial axis transform of the cluster, centers of all maximal disks in the cluster, centers of bi-tangent circles in the cluster, ridges of a distance function in the cluster, intersection of distances from boundary of the cluster, curve evolution of the cluster, level sets of the cluster, peeling of the cluster, symmetry set of the cluster, morphological skeletonization of the cluster, straight skeleton of the cluster, Grassfire transform of the cluster, and another characteristics.

Clause 72: The method of the wireless monitoring system of clause 67, further comprising: computing at least one of: the center, cluster center, and location, of at least one of: an inactive non-static object, an object with stationary motion, an object with periodic motion, an object with regular motion, an object with non-random motion and an object with non-chaotic motion, as at least one of DoI and PoI associated with at least one of: largest periodicity measure, largest periodicity metric, largest dominant periodic signal, largest autocorrelation function (ACF) peak, largest dominant frequency component, largest repeatedness, and least impulsiveness.

Clause 73: The method of the wireless monitoring system of clause 67, further comprising: computing at least one of: the center, cluster center, and location, of at least one of: an active non-static object, an object with non-stationary motion, an object with non-periodic motion, an object with irregular motion, an object with random motion, an object with random body motion (RBM) and an object with chaotic motion, as at least one of DoI and PoI associated with at least one of: largest variability measure, largest variability metric, largest variation measure, largest variation metric, largest variance, largest standard deviation, largest magnitude variance, largest phase variance, largest spread, largest dispersion, largest deviation, largest divergence, largest range, largest interquartile range, largest total variation, largest absolute deviation, and largest total deviation.

Clause 74: The method of the wireless monitoring system of clause 2, further comprising: computing a time series of observables based on at least one of: the number of TSCI, a set of TSDI computed based on the number of TSCI, and a subset of TSDI in which object presence is detected; removing an influence of the first repetitive motion from the time series of observables; computing a series of second instances of the second repetitive motion based on the series of observables after the influence of the first repetitive motion is removed, wherein each second instance is associated with a time stamp; computing the second information of the second repetitive motion based on the series of second instances.

Clause 75: The method of the wireless monitoring system of clause 74, further comprising: computing a series of first instances of the first repetitive motion based on the time series of observables before the influence of the first repetitive motion removed, wherein each first instance is associated with a time stamp; computing the first information of the first repetitive motion based on the series of first instances.

Clause 76: The method of the wireless monitoring system of clause 74, further comprising: at least one of: preprocessing, processing and postprocessing, the time series of observables based on at least one of: filtering, linear filtering, convolution, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, decision-feedback filtering, interpolation, extrapolation, decimation, subsampling, upsampling, resampling, transform, inverse transform, feature extraction, projection, decomposition, orthogonal projection, non-orthogonal projection, overcomplete projection, eigen-decomposition, singular value decomposition (SVD), principle component analysis (PCA), independent component analysis (ICA), time correction, time base correction, phase correction, magnitude correction, phase cleaning, magnitude cleaning, matched filtering, enhancement, restoration, denoising, smoothing, signal conditioning, sorting, thresholding, soft thresholding, hard thresholding, clipping, soft clipping, scaling, folding, grouping, energy computation, first derivative, second order derivative, high order derivative, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another time series, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and another operation.

Clause 77: The method of the wireless monitoring system of clause 1, further comprising: computing a time series of observables based on at least one of: the number of TSCI, a set of TSDI computed based on the number of TSCI, and a subset of TSDI in which object presence is detected; computing a series of first instances of the first repetitive motion based on the time series of observables, wherein each first instance is associated with a time stamp; computing the first information of the first repetitive motion based on the series of first instances.

Clause 78: The method of the wireless monitoring system of clause 74 or clause 75 or clause 77, further comprising: testing each instance of the series of instance; identifying an erroneous instance of the series of instance, wherein the erroneous instance is associated with an erroneous time stamp; correcting at least one of: the erroneous instance, and the erroneous time stamp.

Clause 79: The method of the wireless monitoring system of clause 78, further comprising: replacing the erroneous instance by a corrected instance.

Clause 80: The method of the wireless monitoring system of clause 78, further comprising: replacing the erroneous time stamp by a corrected time stamp.

Clause 81: The method of the wireless monitoring system of clause 78, further comprising: identifying a time window associated with the erroneous instance; computing an autocorrelation function of the time window; normalizing the autocorrelation function; replacing a section of the time window of the time series of observables by the autocorrelation function; recomputing the erroneous instance based on the time series of observables with the replaced section of the time window.

Clause 82: The method of the wireless monitoring system of clause 78, further comprising: testing each instance by computing at least one inter-instance period, each inter-instance period being a difference between time stamps associated with a pair of consecutive instances associated with the instance, computing a function of the at least one inter-instance period associated with the instance; identify the instance as an erroneous instance if the function is greater than a threshold.

Clause 83: The method of the wireless monitoring system of clause 78: wherein the function comprises at least one of: a sum, difference, ratio, division, multiplication, average, weighted average, transform, variability measure, variance, standard deviation, variation, spread, dispersion, deviation, of divergence, range, interquartile range, total variation, absolute deviation, total deviation, outlier measure, irregularity measure, change measure, derivative, first order derivative, second order derivative, high order derivative, lowpass filter, bandpass filter, highpass filter, and another function.

Clause 84: The method of the wireless monitoring system of clause 78, further comprising: computing a count of erroneous instance; computing at least one of: the first information and the second information, based on the count.

Clause 85: The method of the wireless monitoring system of clause 74 or clause 75 or clause 76, further comprising: computing an inter-instance period of a pair of consecutive instances, the inter-instance period being a different between the time stamps associated with the pair of consecutive instances; computing at least one of: the first information and the second information, based on the inter-instance period.

Clause 86: The method of the wireless monitoring system of clause 85, further comprising: computing a variability measure of a series of inter-instance periods each computed based on a pair of consecutive instances of the time series of instances.

In one example, the disclosed ViMo system can be used to monitor vital signs of a person, e.g. a patient who is not wearing or attached to any physical device. The ViMo is a wireless system that can accurately detect the patient's vital signs (e.g. breathing, heartbeat) by using purely the reflections of RF signals off the patient's body. The disclosed system can estimate a heart rate of the patient leveraging both the time and frequency diversity, after eliminating an interference of the breathing signal.

In another example, the disclosed system can monitor vital signs of multiple persons and/or animals at the same time (e.g. in a circus, a zoo, an apartment building, an office building, etc.), using a single commercial 802.1 lad device. The disclosed system can locate and count human/animal targets without any prior calibration. The disclosed system can work well in various scenarios, including NLOS and motion artifacts.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:
1. A wireless monitoring system, comprising:
a transmitter configured for transmitting, using N1 transmit antennas, a wireless signal through a wireless multipath channel of a venue, while a first object in the venue is having a first repetitive motion and an additional repetitive motion;
a receiver configured for:
receiving, using N2 receive antennas, the wireless signal through the wireless multipath channel, and
extracting a plurality of time series of channel information (TSCI) of the wireless multipath channel from the wireless signal, wherein:
N1 and N2 are positive integers, and
each of the plurality of TSCI is associated with a transmit antenna of the transmitter and a receive antenna of the receiver; and
a processor configured for:
computing a time series of directional information (TSDI) based on the plurality of TSCI and a beamforming, wherein:
the TSDI is associated with a direction-of-interest (DoI) which is a direction associated with object presence, and
each directional information (DI) of the TSDI comprises a number of components each associated with a propagation delay and a distance, determining that a first component of DI is associated with object presence in a time window, computing a first information of the first repetitive motion based on a feature of the first component of each DI in the time window of the TSDI, wherein the feature comprises at least one of: magnitude, phase, real component, imaginary component, a square of magnitude, or an exponential function of magnitude, computing an additional information of the additional repetitive motion in the time window of the TSDI based on: the feature of the first component of each DI in the time window of the TSDI and the feature of a second component of each DI in the time window of the TSDI, wherein the first information and the additional information comprise at least one of: heartbeat information of the first object or breathing information of the first object, monitoring the first repetitive motion of the first object based on the first information, and monitoring the additional repetitive motion of the first object based on the additional information.

2. The wireless monitoring system of claim 1, wherein:
at least one of the first object and a second object in the venue, is having a second repetitive motion; and
the processor is further configured for:
computing a second information of the second repetitive motion based on the plurality of TSCI,
monitoring the second repetitive motion based on the second information,
computing at least one analytics based on at least one of: the first information and the second information,
storing at least one of: the first information, the second information, and the at least one analytics,
communicating, to at least one of a server and a user device, at least one of: the first information, the second information and the at least one analytics, and
generating a presentation based on at least one of: the first information, the second information, and the at least one analytics.

3. The wireless monitoring system of claim 2, wherein:
the first repetitive motion and the second repetitive motion are monitored simultaneously based on the plurality of TSCI; or
the second repetitive motion is monitored based on the monitoring of the first repetitive motion.

4. The wireless monitoring system of claim 1, wherein:
at least one of the first object and a second object in the venue, is having a second repetitive motion; and
the processor is further configured for:
computing a second information of the second repetitive motion based on the plurality of TSCI and a removal of an influence of the first repetitive motion, and
monitoring the second repetitive motion based on the second information.

5. The wireless monitoring system of claim 1, wherein the processor is further configured for:
computing a beamforming based on the plurality of TSCI; and
computing at least one derived TSCI each associated with a direction based on the beamforming, wherein:
each channel information (CI) of the plurality of TSCI comprises a number of components each associated with a propagation delay,
all CI has a same number of components,
the beamforming is computed at a particular time in a component-wise manner,
a derived CI at the particular time is computed based on a beamforming applied to all respective CI of the plurality of TSCI at the particular time,
each component of the derived CI at the particular time is computed based on the corresponding component of all respective CI of the plurality of TSCI.

6. The wireless monitoring system of claim 1, wherein the processor is further configured for:
computing a spatial spectrum associated with a set of propagation delays for a set of directions based on the plurality of TSCI and a beamforming; and
monitoring the first object based on the spatial spectrum, wherein:
each direction is associated with at least one of: an angle, an azimuth, an elevation angle, a coordinate, a steering vector, a link between a transmit antenna of the transmitter and a receive antenna of the receiver, a path associated with an object in the direction, and another direction descriptor, and
each propagation delay is associated with at least one of: a time lag, a time delay, a time index, a propagation time, a time-of-flight, a distance, a range, and another time descriptor.

7. The wireless monitoring system of claim 1, wherein the processor is further configured for:
computing, based on the plurality of TSCI and a beamforming, a set of time series of directional information (TSDI), wherein each of the set of TSDI is associated with a direction; and
computing the first information of the first repetitive motion based on the set of TSDI, wherein:
a channel information (CI) of the plurality of TSCI comprises at least one of:
channel state information (CSI), channel impulse response (CIR), and channel frequency response (CFR), and
a directional information (DI) of the set of TSDI comprises at least one of: CI, CSI, CIR, CFR, a directional CI (DCI) associated with a direction, a directional CSI (DCSI) associated with a direction, a directional CIR (DCIR) associated with a direction, a directional CFR (DCFR) associated with a direction,
a component of at least one of: the CI, CSI, CIR, CFR, DCI, DCSI, DCIR, and DCFR, associated with a distance,
a magnitude of at least one of: the CI, CSI, CIR, CFR, DCI, DCSI, DCIR, DCFR and the component,
a phase of at least one of: the CI, CSI, CIR, CFR, DCI, DCSI, DCIR, DCFR and the component,
a directional weight, spatial spectrum, distribution of an information of reflected signals in the space of the venue, distribution of energy of reflected signals in the space of the venue, a heat map,
and another directional information.

8. The wireless monitoring system of claim 7, wherein the processor is further configured for:
for each respective TSDI in a respective direction,
computing a respective test quantity based on the respective TSDI for the respective direction and a distance, and
detecting object presence at the distance in the respective direction if the respective test quantity is greater than a respective threshold;

computing a set of direction-of-interest (DoI) comprising directions in which object presence is detected; and computing a point-of-interest (PoI) associated with object presence, wherein the PoI is a point corresponding to the respective direction and the distance at which object presence is detected, wherein:

the respective threshold is at least one of: a distance-adaptive threshold or a direction-adaptive threshold, the respective threshold is based adaptively on at least one of: the distance, a constant false alarm rate (CFAR), weighted averaging of values of neighboring directions of the respective direction, weighted averaging of values of the neighboring directions excluding a guard region of immediately neighboring directions of the respective direction, cell-averaging constant false alarm rate (CA-CFAR), and another directional scheme.

9. The wireless monitoring system of claim 1, wherein the processor is further configured for:

computing a statistical function of the feature of the first component of each DI in the time window of the TSDI;

computing at least one characteristic point of the statistical function; and computing the first information of the first repetitive motion based on the at least one characteristic point.

10. The wireless monitoring system of claim 1, wherein the processor is further configured for:

computing an estimate of a first influence of the first repetitive motion on the feature by suppressing a second influence of other repetitive motions on the feature;

removing the first influence of the first repetitive motion on the feature by subtracting the estimate of the first influence from the feature of the first component of each DI in the time window of the TSDI, to generate a processed feature; and computing the second information of the second repetitive motion of the first object based on the processed feature.

11. The wireless monitoring system of claim 1, wherein the processor is further configured for:

determining a number of direction-of-interest (DoI), wherein each of the number of DoI is a direction associated with object presence of the first object;

computing a number of time series of directional information (TSDI), wherein each of the number of TSDI is for a respective DoI;

computing a plurality of tentative first information of the first repetitive motion, wherein each respective tentative first information is computed based on a respective TSDI associated with a respective DoI; and computing the first information by combining the plurality of tentative first information.

12. The wireless monitoring system of claim 1, wherein the processor is further configured for:

computing a set of point-of-interest (PoI) based on at least one of: the number of TSCI and a time series of directional information (TSDI) computed based on the number of TSCI and a beamforming, wherein each of the set of PoI is associated with an object presence and is a point in the venue associated with a propagation delay and a direction; and monitoring the first object based on the set of PoI.

13. The wireless monitoring system of claim 12, wherein the processor is further configured for:

computing a propagation-delay-of-interest (PDoI) based on the plurality of TSCI and the TSDI, wherein the PDoI comprises a set of selected propagation delays, and each selected propagation delay is associated with a respective distance and a presence of the first object; and computing the set of PoI based on the PDoI.

14. The wireless monitoring system of claim 13, wherein computing the PDoI comprises:

computing a variability measure of a TSDI associated with a propagation delay, wherein each directional information of the TSDI is computed based on the plurality of TSCI and a beamforming, wherein the variability measure comprises at least one of: a standard deviation, variance, a measure of variation, a measure of spread, a measure of dispersion, a measure of deviation, a measure of divergence, range, inter-quartile range, total variation, absolute deviation, and total deviation;

selecting the propagation delay to be associated with the presence of the first object when the variability measure is greater than a threshold; and adding the selected propagation delay to the PDoI.

15. The wireless monitoring system of claim 14, wherein the processor is further configured for:

computing a set of variability measures associated with a set of propagation delays, wherein each of the set of variability measures is associated with a respective propagation delay; and determining the threshold based on a function of the set of variability measures, wherein the function comprises at least one of: mean, median, mode, percentile, weighted average, geometric mean, harmonic mean, trimmed mean, variance, scaling, offset, linear function, nonlinear function, monotonic non-decreasing function, monotonic non-increasing function, and a hybrid function.

16. The wireless monitoring system of claim 13, wherein:

the PDoI comprises at least two clusters of consecutive propagation delay values; and the processor is further configured for:

computing a distance between two clusters of the PDoI, and expanding the PDoI by adding a missing propagation delay value between the two clusters to the PDoI when the distance is less than a threshold.

17. The wireless monitoring system of claim 13, wherein:

the PDoI comprises at least one disjoint cluster of consecutive propagation delay values; and the processor is further configured for:

examining the TSDI with associated propagation delay in the PDoI in a particular direction, identifying a cell of points in the particular direction, wherein propagation delay values associated with the cell of points form a subset of a cluster of the PDoI and each point in the cell has an associated directional information greater than a threshold, selecting in the cell of points a characteristic point associated with a propagation delay with at least one of the following characteristics of the cell: minimum, maximum, mid-point, mean, centroid with respect to (w.r.t.) the TSDI, mean w.r.t. the TSDI, weighted mean w.r.t. the TSDI, median w.r.t. the TSDI, mode w.r.t. the TSDI, a percentile w.r.t. the TSDI, minimum w.r.t. the TSDI, maximum w.r.t. the TSDI, local minimum w.r.t. the TSDI, local maximum w.r.t. the TSDI, minimum slope w.r.t. the TSDI, maximum slope w.r.t. the TSDI, local minimum slope w.r.t. the TSDI, local maximum slope w.r.t. the TSDI, and another characteristics, adding the selected characteristic point as a PoI to the set of PoI, refining the points in the PoI, cleaning the set of PoI based on the associated directional information (DI), processing the set of PoI and the associated DI, and monitoring the first object based on the processing.

18. The wireless monitoring system of claim 13, wherein the processor is further configured for:

determining a number of clusters in the set of PoI by applying a clustering algorithm that optimizes a cost function;

validating the clusters in the set of PoI based on a medoid distance;

splitting a cluster when an intra-cluster medoid distance is greater than a first threshold;

combining two clusters when an inter-cluster medoid distance is less than a second threshold;

associating the number of clusters with at least one object in the venue; and computing at least one of:
a quantity of the at least one object,
a location of the first object based on a geometric medoid of all points belonging to an associated cluster, and
a height of the first object based on a maximum of heights associated with all points belonging to the associated cluster.

19. The wireless monitoring system of claim 1, wherein:
the N1 transmit antennas of the transmitter are arranged in a first lattice with at least one first characteristic spacing;
the N2 receive antennas of the receiver are arranged in a second lattice with at least one second characteristic spacing;
the transmitter and the receiver are at least one of the following:
two different devices placed at two different locations in the venue,
two collocated devices placed at similar locations in the venue, and
a same device comprising an integrated circuit (IC) that transmits and receives the wireless signal and obtains the plurality of TSCI from the wireless signal.

20. The wireless monitoring system of claim 7, wherein the processor is further configured for:
detecting a presence of the first object at a particular time at a particular point at a particular distance in a particular direction based on a determination that a first test quantity associated with a particular component of a particular DI of a particular TSDI is greater than a first threshold T1, wherein:
the particular TSDI is associated with the particular direction,
the particular DI is associated the particular time, and
the particular component is associated with the particular distance time;
computing at least one of: a second test quantity and a third test quantity;
classifying the first object at the particular point, based on at least one of: the second test quantity and the third test quantity, to be at least one of:
a static object when the second test quantity is less than a second threshold T2,
a non-static object when the second test quantity is greater than T2,
an active non-static object when the second test quantity is greater than a third threshold T3 that is greater than T2,
an active non-static object when: the second test quantity is between T2 and T3, and the third test quantity is less than a fourth threshold T4,
an inactive non-static object when: the second test quantity is between T2 and T3, and the third test quantity is greater than T4; and
classifying a motion of the first object at the particular point to be at least one of:
static when the second test quantity is less than a fifth threshold T5,
non-static if the second test quantity is greater than T5,
non-static and at least one of: non-stationary, non-periodic, irregular, and random, when the second test quantity is greater than a sixth threshold T6 that is greater than T5,
non-static and at least one of: non-stationary, non-periodic, irregular, and random, when: the second test quantity is between T5 and T6, and the third test quantity is less than a seventh threshold T7, and
non-static and at least one of: stationary, periodic, regular, and non-random, when:
the second test quantity is between T5 and T6, and the third test quantity is greater than T7.

21. The wireless monitoring system of claim 7, wherein the processor is further configured for:
identifying a set of direction-of-interest (DoI) in which object presence is detected;
identifying a set of points of interest (PoI), wherein:
each PoI is a point in the venue associated with a respective DoI and a respective distance in the DoI,
each PoI is associated with a respective component of a respective DI of a respective TSDI associated with the respective DoI,
object presence is detected at the PoI based on a respective test quantity associated with the respective component of the respective DI of the respective TSDI being greater than a respective threshold;
computing a cluster of PoI and/or a cluster of DoI, based on the set of PoI and DoI;
computing at least one of: a shape, surface, manifold, skeleton, silhouette, size, weight, health condition, well-being, center, centerline, cluster center, location, movement, motion, activity, gesture, gait, handwriting, of the first object;
combining two PoI into a PoI cluster when a distance between the two PoI is less than a threshold; and
combining two DoI into a DoI cluster when a distance between the two DoI is less than a threshold.

22. The wireless monitoring system of claim 2, wherein the processor is further configured for:
computing a time series of observables based on at least one of: the plurality of TSCI, a set of TSDI computed based on the plurality of TSCI, and a subset of TSDI in which object presence is detected;
removing an influence of the first repetitive motion from the time series of observables;
computing a series of first instances of the first repetitive motion based on the time series of observables before the influence of the first repetitive motion is removed, wherein each first instance is associated with a time stamp;

computing the first information of the first repetitive motion based on the series of first instances;
computing a series of second instances of the second repetitive motion based on the time series of observables after the influence of the first repetitive motion is removed, wherein each second instance is associated with a time stamp; and
computing the second information of the second repetitive motion based on the series of second instances.

23. The wireless monitoring system of claim 1, wherein the processor is further configured for:
computing a time series of observables based on at least one of: the plurality of TSCI, a set of TSDI computed based on the plurality of TSCI, and a subset of TSDI in which object presence is detected;
computing a series of instances of the first repetitive motion based on the time series of observables, wherein each first instance is associated with a time stamp;
computing the first information of the first repetitive motion based on the series of instances;
testing each instance of the series of instances to identify an erroneous instance of the series of instances, wherein the erroneous instance is associated with an erroneous time stamp; and
correcting at least one of: the erroneous instance and the erroneous time stamp.

24. The wireless monitoring system of claim 23, wherein the correcting comprises at least one of:
replacing the erroneous instance by a corrected instance;
replacing the erroneous time stamp by a corrected time stamp;
identifying a time window associated with the erroneous instance;
computing an autocorrelation function of the time window;
normalizing the autocorrelation function;
replacing a section of the time window of the time series of observables by the autocorrelation function; and
re-computing the erroneous instance based on the time series of observables with the replaced section of the time window.

25. The wireless monitoring system of claim 23, wherein the testing each instance comprises:
computing at least one inter-instance period, each inter-instance period being a difference between time stamps associated with a pair of consecutive instances associated with the instance;
computing a function of the at least one inter-instance period associated with the instance; and
identifying the instance as an erroneous instance when the function is greater than a threshold.

26. The wireless monitoring system of claim 22, wherein the processor is further configured for:
computing a first quantity of erroneous instances in the series of first instances;
computing a second quantity of erroneous instances in the series of second instances;
computing an inter-instance period of a pair of consecutive instances, the inter-instance period being a different between the time stamps associated with the pair of consecutive instances;
computing at least one of the first information and the second information, based on at least one of: the inter-instance period, the first quantity and the second quantity; and
computing a variability measure of a series of inter-instance periods each of which is computed based on a pair of consecutive instances.

27. A method, implemented by a processor, a memory communicatively coupled with the processor, and a set of instructions stored in the memory to be executed by the processor, comprising:
transmitting, using N1 transmit antennas of a first heterogeneous wireless device, a wireless signal through a wireless multipath channel of a venue, while an object in the venue is having a repetitive motion and an additional repetitive motion;
receiving, using N2 receive antennas of a second heterogeneous wireless device, the wireless signal through the wireless multipath channel;
obtaining a plurality of time series of channel information (TSCI) of the wireless multipath channel from the wireless signal, wherein:
N1 and N2 are positive integers, and
each of the plurality of TSCI is associated with a transmit antenna of the first heterogeneous wireless device and a receive antenna of the second heterogeneous wireless device;
computing a timing information of the repetitive motion based on the plurality of TSCI;
computing an additional timing information of the additional repetitive motion based on the plurality of TSCI and a removal of an influence of the repetitive motion, wherein the timing information comprises heartbeat information of the object, wherein the additional timing information comprises breathing information of the object;
monitoring the repetitive motion of the object based on the timing information;
monitoring the additional repetitive motion of the object based on the additional timing information;
computing a first test quantity and a second test quantity based on the timing information or the additional timing information; and
classifying the object, based on the first test quantity and the second test quantity, to be one of: a static object, an active non-static object, and an inactive non-static object, wherein:
the object is classified as the static object when the first test quantity is less than a first threshold T1,
the object is classified as the active non-static object when: the first test quantity is between T1 and a second threshold T2, and the second test quantity is less than a third threshold T3, and
the object is classified as the inactive non-static object when: the first test quantity is between T1 and T2, and the second test quantity is greater than T3.

28. A wireless monitoring system, comprising:
a plurality of pairs of transmitters and receivers in a venue, wherein for each pair:
a respective transmitter of the pair is configured for asynchronously transmitting a respective wireless signal through a wireless multipath channel, while a first object in the venue is having a first repetitive motion,
a respective receiver of the pair is configured for asynchronously receiving the respective wireless signal through the wireless multipath channel, and extracting a respective time series of channel information (TSCI) of the wireless multipath channel from the respective wireless signal, wherein:

the transmitter and the receiver of a first pair of the plurality of pairs are collocated at a same location in the venue, the transmitter and the receiver of a second pair of the plurality of pairs are positioned at two different locations in the venue, and a plurality of TSCI is obtained by the receivers of the plurality of pairs; and a processor configured for:

computing a first information of the first repetitive motion based on the plurality of TSCI, monitoring the first repetitive motion of the first object based on the first information, computing a first test quantity and a second test quantity based on the first information, and classifying the first object, based on the first test quantity and the second test quantity, to be one of: a static object, an active non-static object, and an inactive non-static object, wherein:

the first object is classified as the static object when the first test quantity is less than a first threshold T1, the first object is classified as the active non-static object when: the first test quantity is between T1 and a second threshold T2, and the second test quantity is less than a third threshold T3, and the first object is classified as the inactive non-static object when: the first test quantity is between T1 and T2, and the second test quantity is greater than T3.

* * * * *